United States Patent
Old et al.

(10) Patent No.: US 7,973,071 B2
(45) Date of Patent: *Jul. 5, 2011

(54) SUBSTITUTED GAMMA LACTAMS AS THERAPEUTIC AGENTS

(75) Inventors: David W. Old, Irvine, CA (US); Danny T. Dinh, Garden Grove, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/323,077

(22) Filed: Nov. 25, 2008

(65) Prior Publication Data

US 2009/0233980 A1   Sep. 17, 2009

Related U.S. Application Data

(63) Continuation of application No. 10/599,046, filed as application No. PCT/US2006/007797 on Mar. 6, 2006, now Pat. No. 7,476,747.

(60) Provisional application No. 60/660,748, filed on Mar. 10, 2005.

(51) Int. Cl.
*A61K 31/40* (2006.01)
*C07D 409/02* (2006.01)

(52) U.S. Cl. ........................ 514/422; 548/517
(58) Field of Classification Search ............. 514/422; 548/517
See application file for complete search history.

(56) References Cited

U.S. PATENT DOCUMENTS

| | | | |
|---|---|---|---|
| 6,437,146 B1 | 8/2002 | Hattori et al. | |
| 6,573,294 B1 | 6/2003 | Old et al. | |
| 6,710,072 B2 | 3/2004 | Burk et al. | |
| 7,473,702 B2 * | 1/2009 | Old et al. | 514/422 |
| 7,476,747 B2 * | 1/2009 | Old et al. | 548/545 |
| 7,592,364 B2 * | 9/2009 | Old et al. | 514/422 |
| 2003/0120079 A1 | 6/2003 | Elworthy et al. | |

FOREIGN PATENT DOCUMENTS

| | | |
|---|---|---|
| WO | 95/19964 | 7/1995 |
| WO | 03/103604 | 12/2003 |
| WO | 2004/037813 | 5/2004 |

OTHER PUBLICATIONS

Testa, Bernard, Biochemical Pharmacology, Prodrug Research: futile or fertile? 68 (2004) 2097-2106.*
Ettmayer, Peter, Medicinal Chemistry, Lessons Learned from Marketed and Investigational Prodrugs, 47(10) (2004) 2394-2404.*
Kwon, Younggil. Handbook of Essential Pharmacokinetics, Pharmacodynamics and Drug Metabolism for Industrial Scientists Jun. 24, 2001, Apr. 24, 2006.
Metabolomics [online]. Retrieved from the Internet Apr. 24, 2008, www.en.wikipedia.org/wiki/Metabolomics.
Stella, Valentino J, Expert Opinion of Therapeutic Patents, Prodrugs as therapeutics, 2004 14(3): 277-280.
Wolff et al. (Burger's Medicinal Chemistry, 5th Ed., vol. 1, pp. 975-977, 1994.

* cited by examiner

*Primary Examiner* — Rebecca L Anderson
*Assistant Examiner* — Samantha L Shterengarts
(74) *Attorney, Agent, or Firm* — Kevin J. Forrestal; John E. Wurst; Doina G. Ene

(57) ABSTRACT

A compound comprising

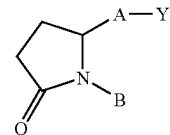

or a pharmaceutically acceptable salt, prodrug, or a metabolite thereof is disclosed herein. Y, A, and B are as described herein.

Figure 1:
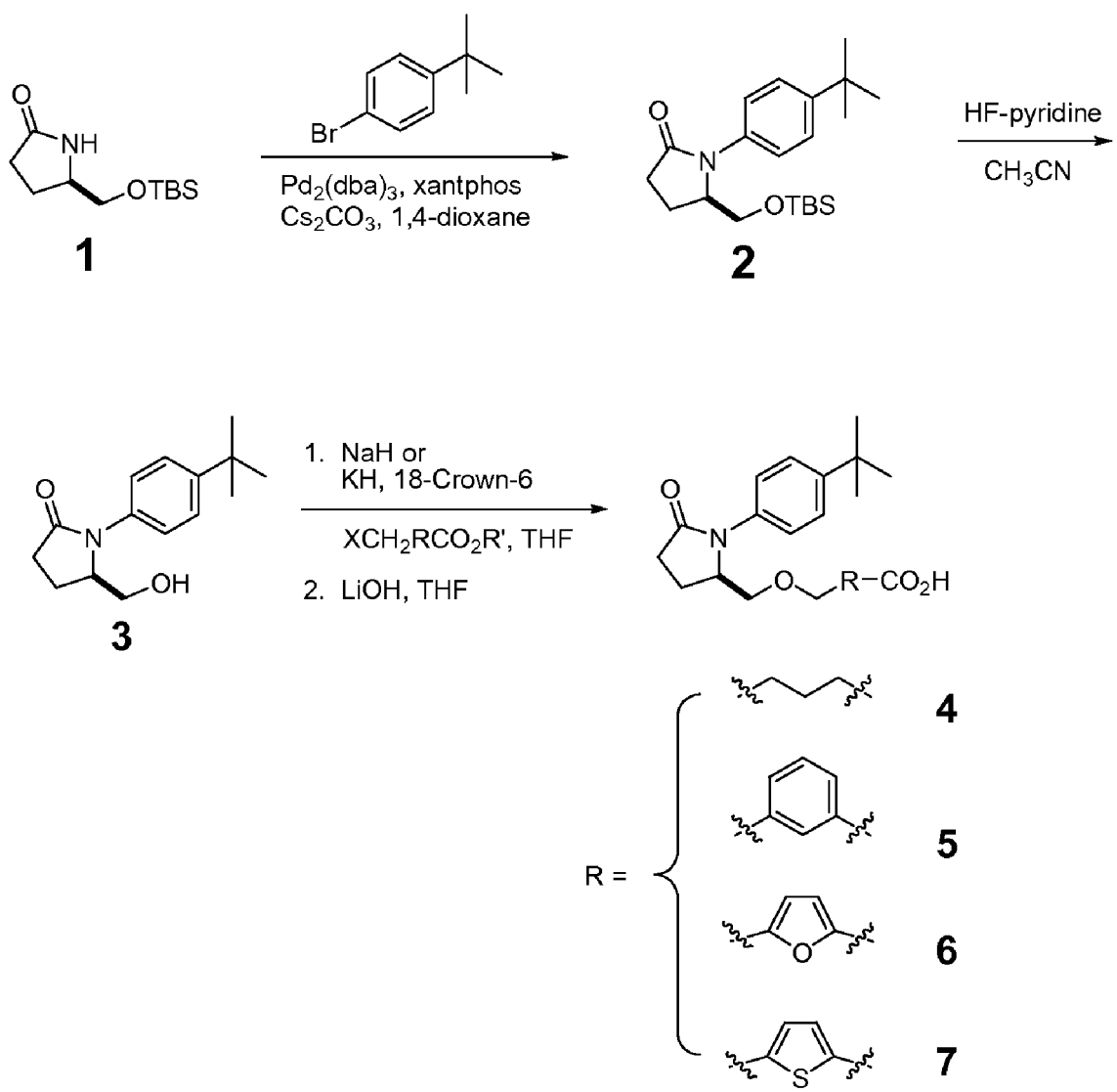

Methods, compositions, and medicaments related to these compounds are also disclosed.

20 Claims, 12 Drawing Sheets

SUBSTITUTED GAMMA LACTAMS AS THERAPEUTIC AGENTS

CROSS REFERENCE TO RELATED APPLICATIONS

This application is a Continuation of U.S. patent application Ser. No. 10/599,046, filed Jun. 29, 2007, now U.S. Pat. No. 7,476,747 which This is a National Stage Application under 35 U.S.C 371 of PCT application PCT/US/2006/007797, filed Mar. 6, 2006, which claims the benefit of Provisional Application No. 60/660,748, filed on Mar. 10, 2005, the contents of which are incorporated by reference in their entirety.

DESCRIPTION OF RELATED ART

Ocular hypotensive agents are useful in the treatment of a number of various ocular hypertensive conditions, such as post-surgical and post-laser trabeculectomy ocular hypertensive episodes, glaucoma, and as presurgical adjuncts.

Glaucoma is a disease of the eye characterized by increased intraocular pressure. On the basis of its etiology, glaucoma has been classified as primary or secondary. For example, primary glaucoma in adults (congenital glaucoma) may be either open-angle or acute or chronic angle-closure. Secondary glaucoma results from pre-existing ocular diseases such as uveitis, intraocular tumor or an enlarged cataract.

The underlying causes of primary glaucoma are not yet known. The increased intraocular tension is due to the obstruction of aqueous humor outflow. In chronic open-angle glaucoma, the anterior chamber and its anatomic structures appear normal, but drainage of the aqueous humor is impeded. In acute or chronic angle-closure glaucoma, the anterior chamber is shallow, the filtration angle is narrowed, and the iris may obstruct the trabecular meshwork at the entrance of the canal of Schlemm. Dilation of the pupil may push the root of the iris forward against the angle, and may produce pupilary block and thus precipitate an acute attack. Eyes with narrow anterior chamber angles are predisposed to acute angle-closure glaucoma attacks of various degrees of severity.

Secondary glaucoma is caused by any interference with the flow of aqueous humor from the posterior chamber into the anterior chamber and subsequently, into the canal of Schlemm. Inflammatory disease of the anterior segment may prevent aqueous escape by causing complete posterior synechia in iris bombe, and may plug the drainage channel with exudates. Other common causes are intraocular tumors, enlarged cataracts, central retinal vein occlusion, trauma to the eye, operative procedures and intraocular hemorrhage.

Considering all types together, glaucoma occurs in about 2% of all persons over the age of 40 and may be asymptotic for years before progressing to rapid loss of vision. In cases where surgery is not indicated, topical β-adrenoreceptor antagonists have traditionally been the drugs of choice for treating glaucoma.

Certain eicosanoids and their derivatives are currently commercially available for use in glaucoma management. Eicosanoids and derivatives include numerous biologically important compounds such as prostaglandins and their derivatives. Prostaglandins can be described as derivatives of prostanoic acid which have the following structural formula:

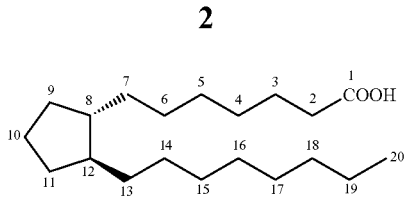

Various types of prostaglandins are known, depending on the structure and substituents carried on the alicyclic ring of the prostanoic acid skeleton. Further classification is based on the number of unsaturated bonds in the side chain indicated by numerical subscripts after the generic type of prostaglandin [e.g. prostaglandin $E_1$ ($PGE_1$), prostaglandin $E_2$ ($PGE_2$)], and on the configuration of the substituents on the alicyclic ring indicated by α or β [e.g. prostaglandin $F_{2\alpha}$ ($PGF_{2\beta}$)].

Prostaglandin $EP_2$ selective agonists are believed to have several medical uses. For example, U.S. Pat. No. 6,437,146 teaches the use of prostaglandin $EP_2$ selective agonists "for treating or preventing inflammation and pain in joint and muscle (e.g., rheumatoid arthritis, rheumatoid spondylitis, osteoarthritis, gouty arthritis, juvenile arthritis, etc.), inflammatory skin condition (e.g., sunburn, burns, eczema, dermatitis, etc.), inflammatory eye condition (e.g., conjunctivitis, etc.), lung disorder in which inflammation is involved (e.g., asthma, bronchitis, pigeon fancier's disease, farmer's lung, etc.), condition of the gastrointestinal tract associated with inflammation (e.g., aphthous ulcer, Chrohn's disease, atrophic gastritis, gastritis varialoforme, ulcerative colitis, coeliac disease, regional ileitis, irritable bowel syndrome, etc.), gingivitis, inflammation, pain and tumescence after operation or injury, pyrexia, pain and other conditions associated with inflammation, allergic disease, systemic lupus crythematosus, scleroderma, polymyositis, tendinitis, bursitis, periarteritis nodose, rheumatic fever, Sjgren's syndrome, Behcet disease, thyroiditis, type I diabetes, diabetic complication (diabetic microangiopathy, diabetic retinopathy, diabetic neohropathy, etc.), nephrotic syndrome, aplastic anemia, myasthenia gravis, uveitis contact dermatitis, psoriasis, Kawasaki disease, sarcoidosis, Hodgkin's disease, Alzheimers disease, kidney dysfunction (nephritis, nephritic syndrome, etc.), liver dysfunction (hepatitis, cirrhosis, etc.), gastrointestinal dysfunction (diarrhea, inflammatory bowel disease, etc.) shock, bone disease characterized by abnormal bone metabolism such as osteoporosis (especially, postmenopausal osteoporosis), hypercalcemia, hyperparathyroidism, Paget's bone diseases, osteolysis, hypercalcemia of malignancy with or without bone metastases, rheumatoid arthritis, periodonritis, osteoarthritis, ostealgia, osteopenia, cancer cachexia, calculosis, lithiasis (especially, urolithiasis), solid carcinoma, mesangial proliferative glomerulonephritis, edema (e.g. cardiac edema, cerebral edema, etc.), hypertension such as malignant hypertension or the like, premenstrual tension, urinary calculus, oliguria such as the one caused by acute or chronic failure, hyperphosphaturia, or the like."

U.S. Pat. No. 6,710,072 teaches the use of EP2 agonists for the treatment or prevention of "osteoporosis, constipation, renal disorders, sexual dysfunction, baldness, diabetes, cancer and in disorder of immune regulation . . . various pathophysiological diseases including acute myocardial infarction, vascular thrombosis, hypertension, pulmonary hypertension, ischemic heart disease, congestive heart failure, and angina pectoris."

BRIEF DESCRIPTION OF THE DRAWING FIGURES

Figure 2:
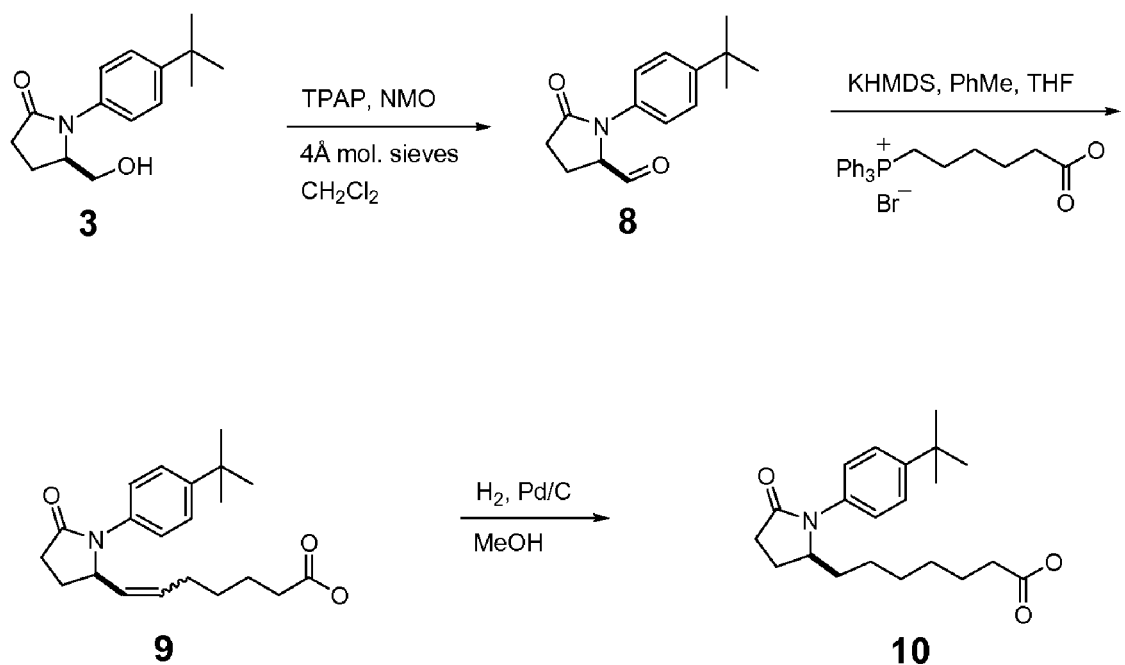
Figure 3:
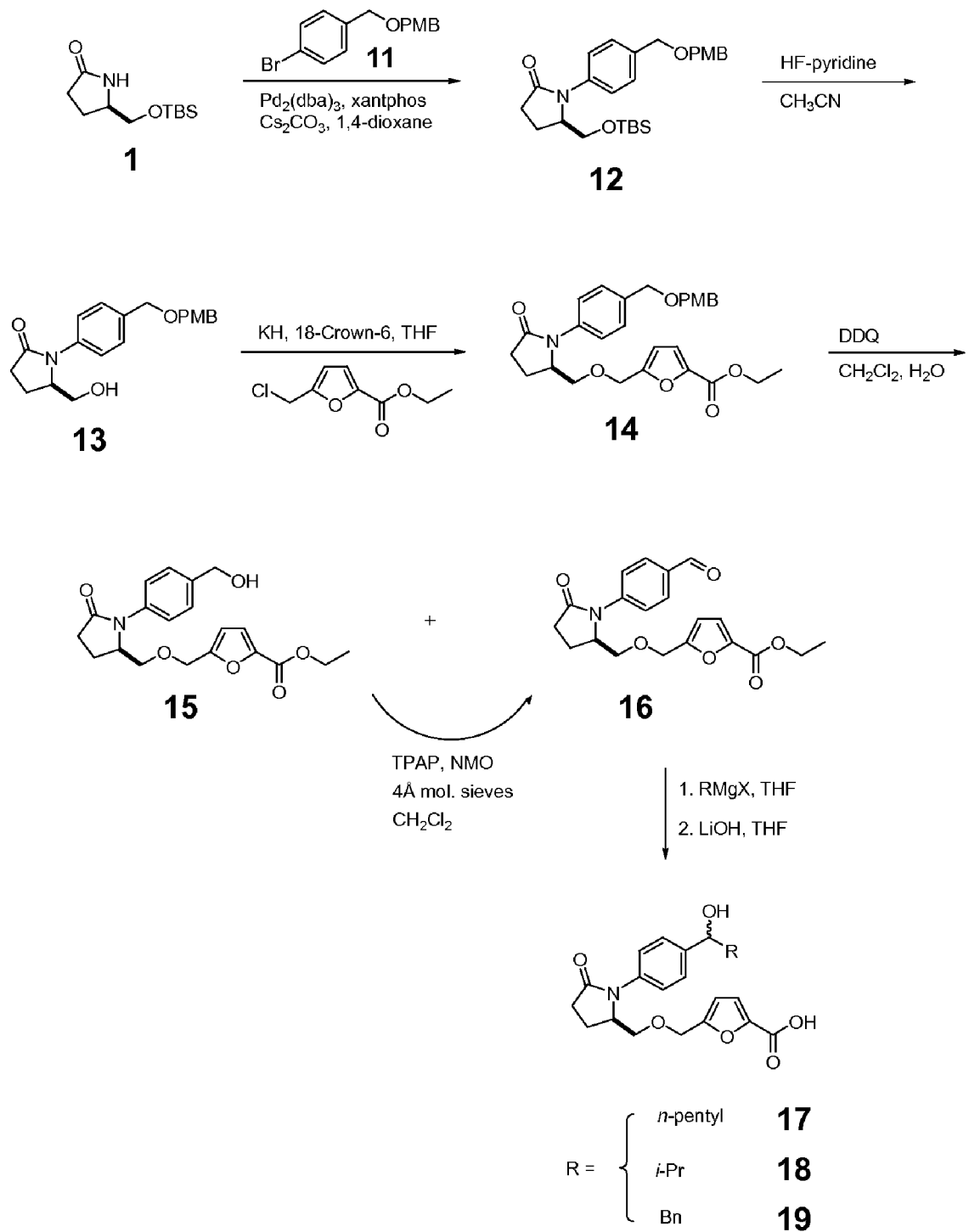
Figure 4:
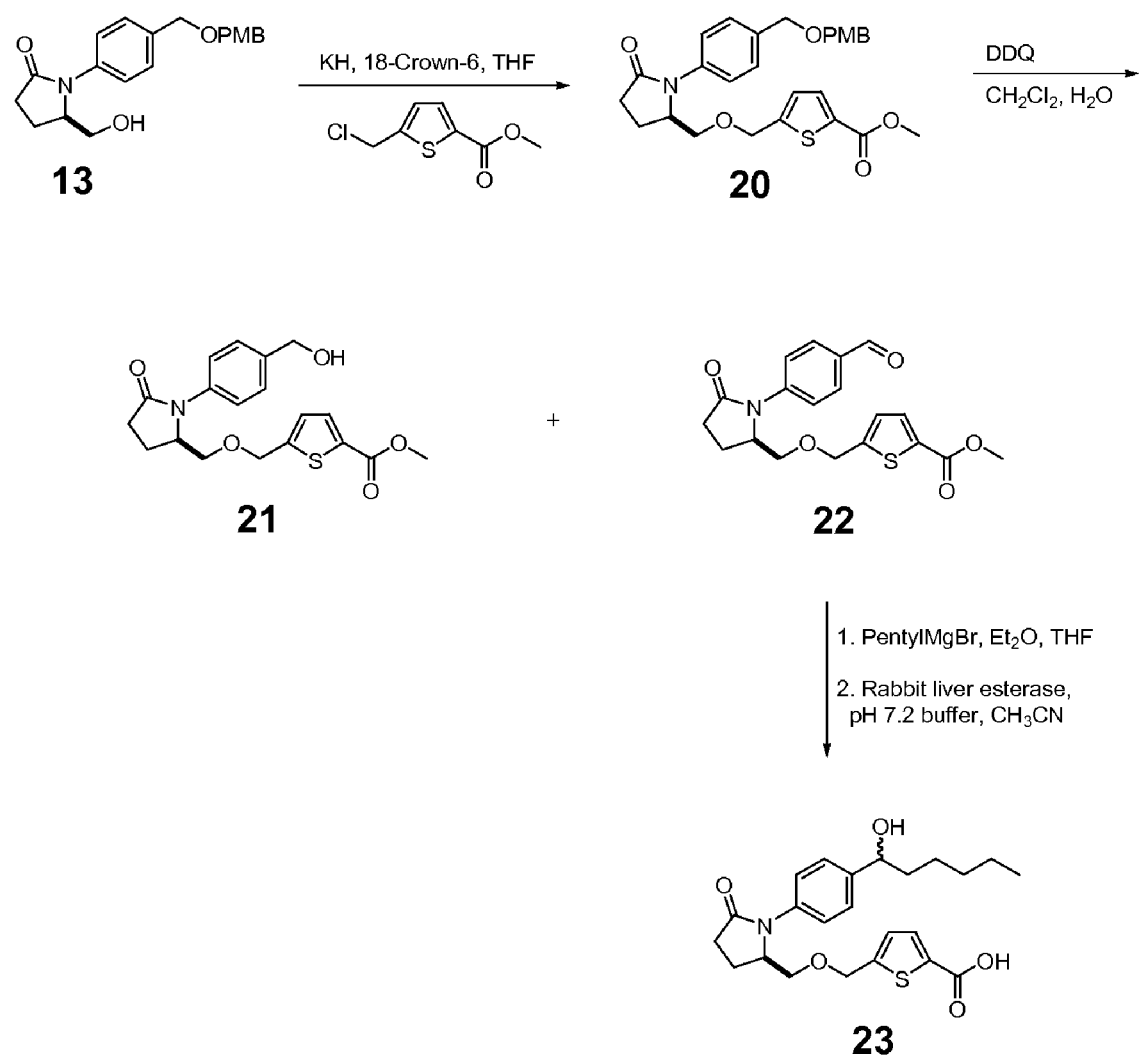
Figure 5:
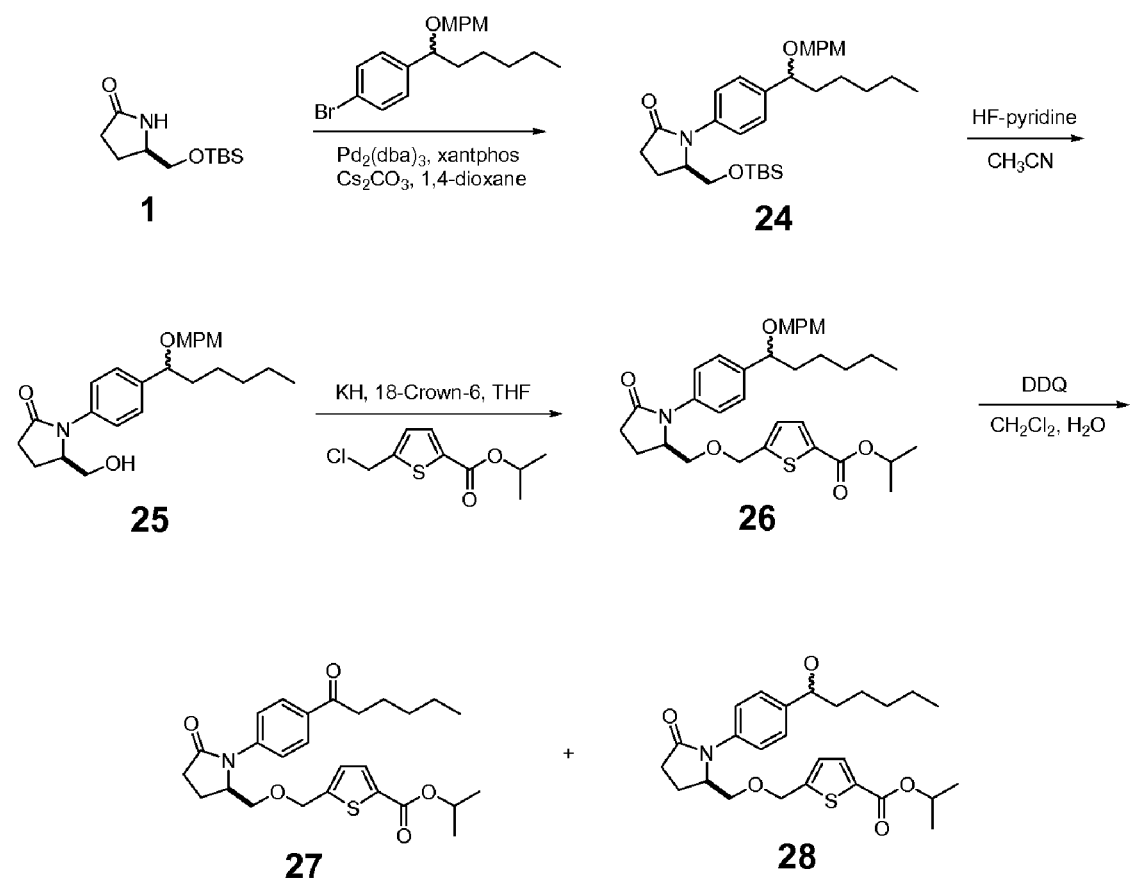
Figure 6:
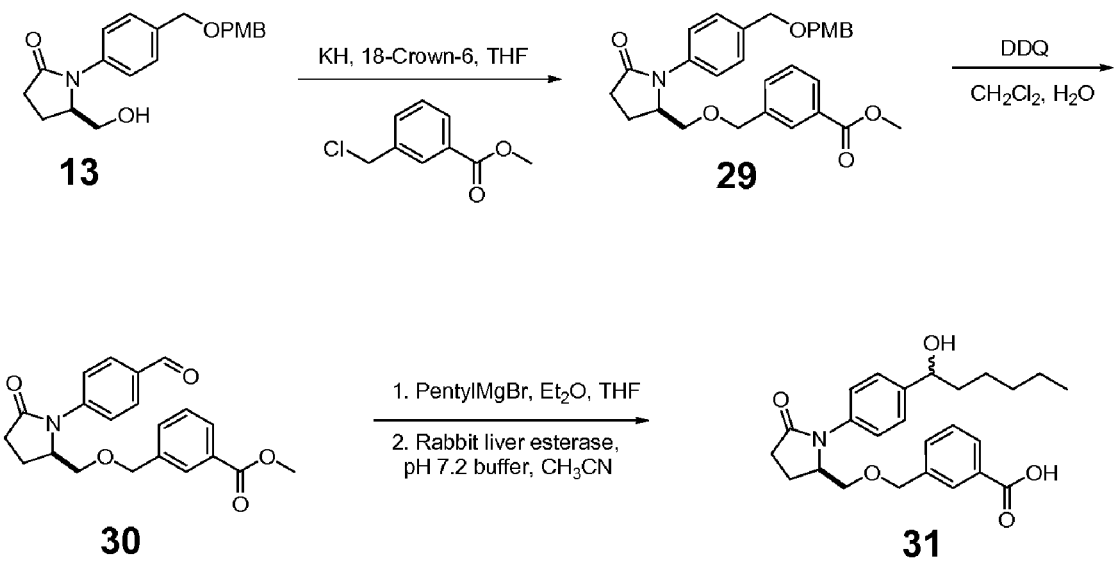
Figure 7:
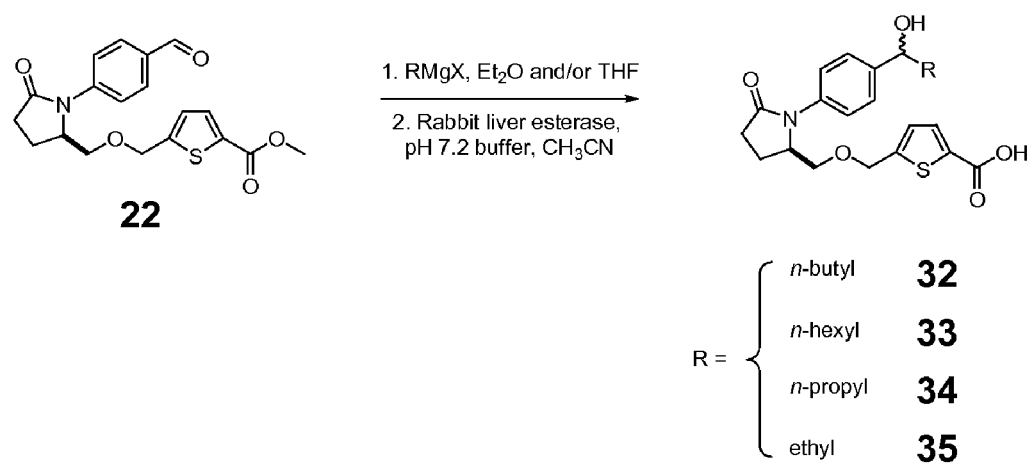
Figure 8:
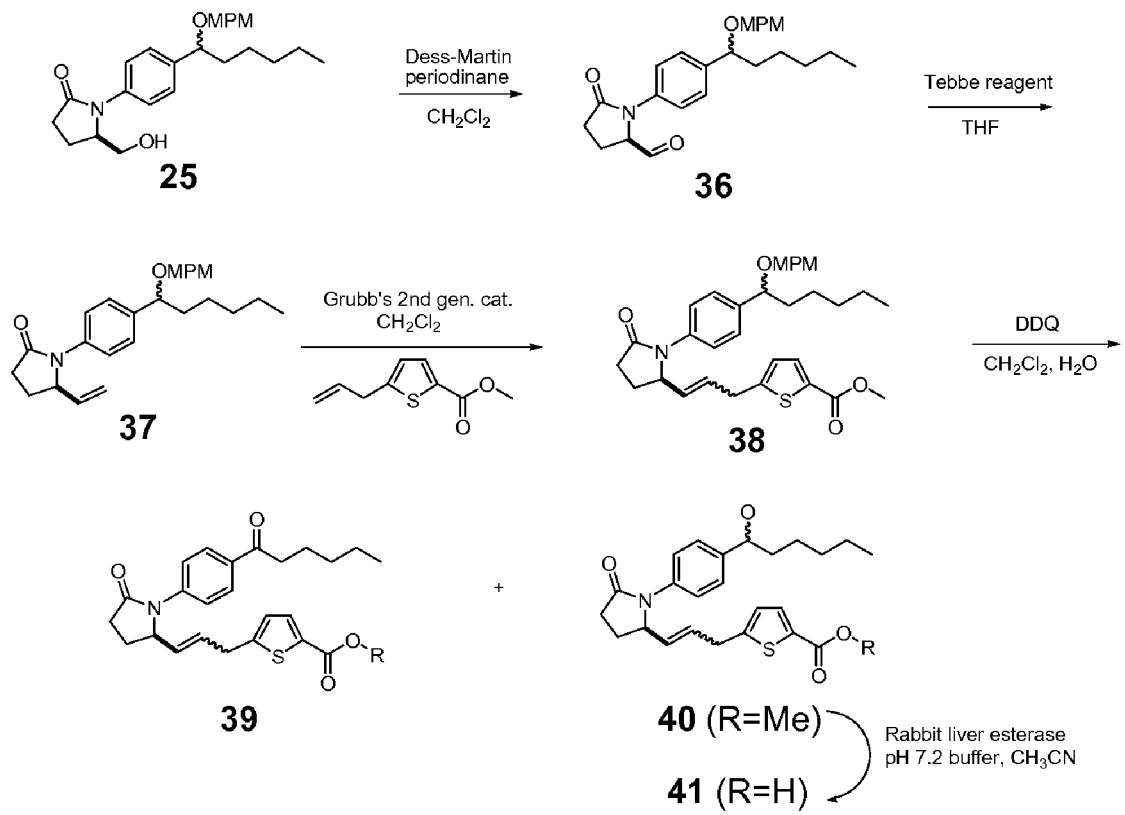
Figure 9:
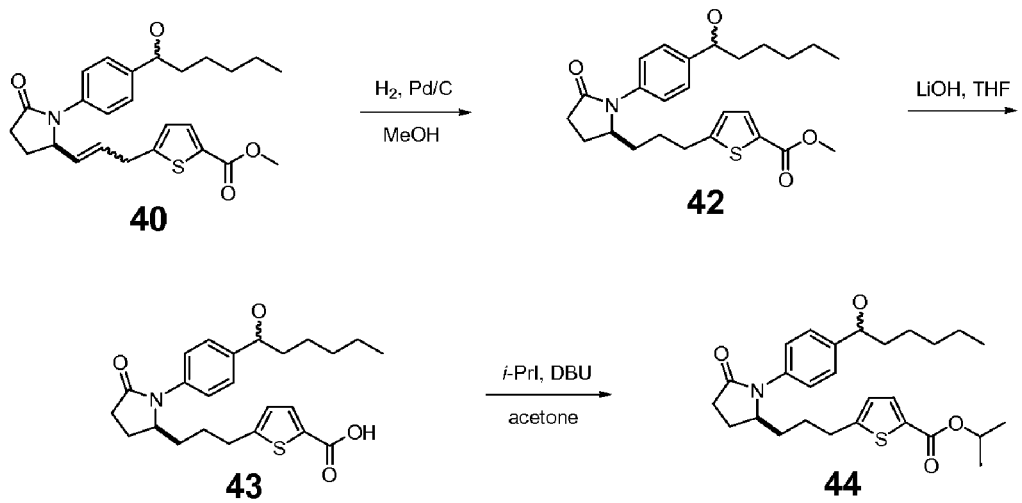
Figure 10:
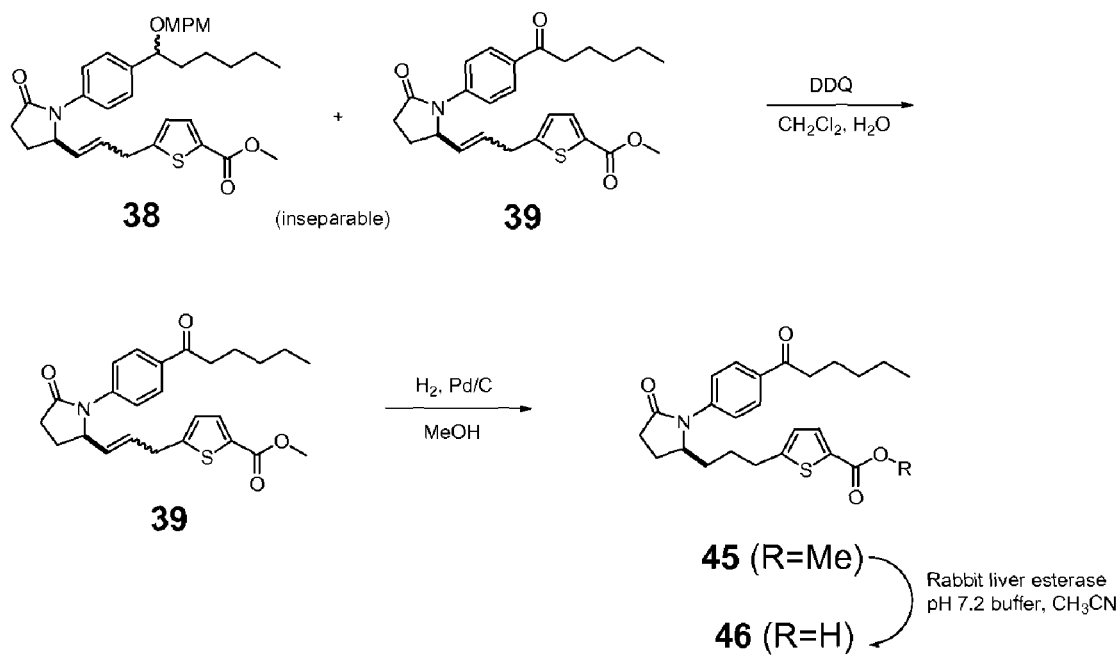
Figure 11:
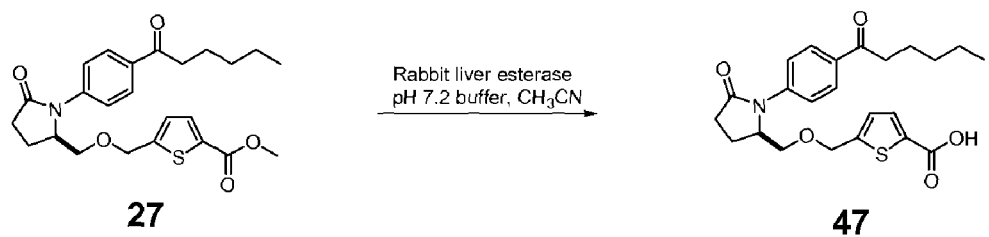
Figure 12:
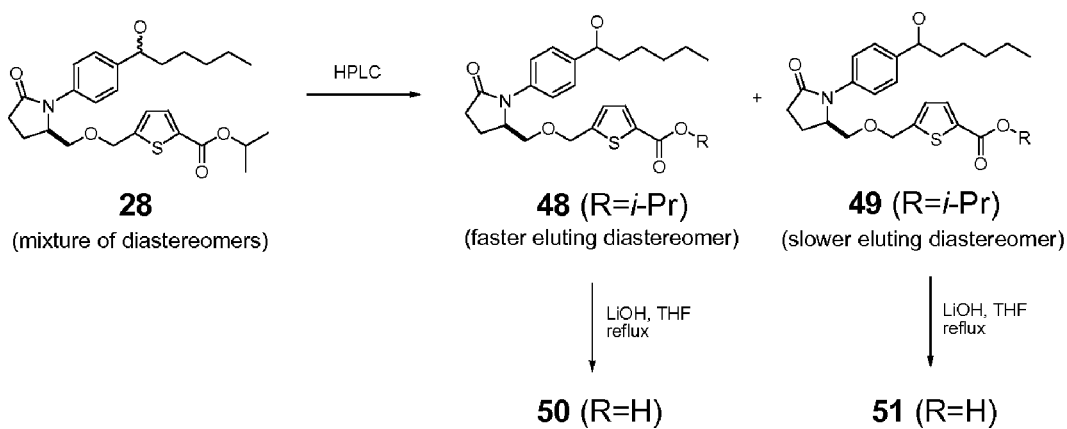
Figure 13:
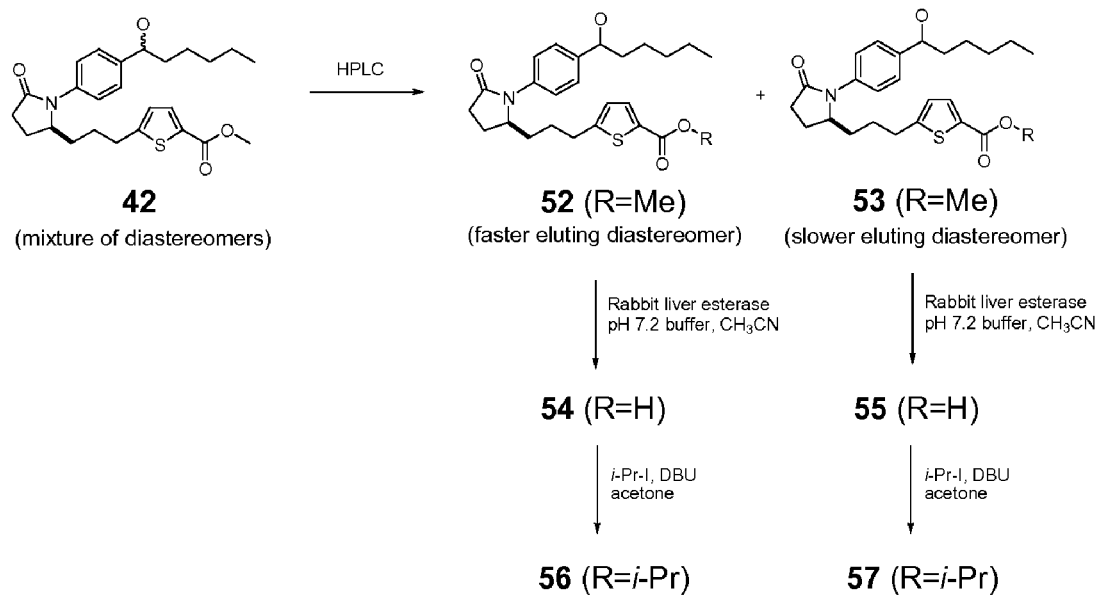
Figure 14:
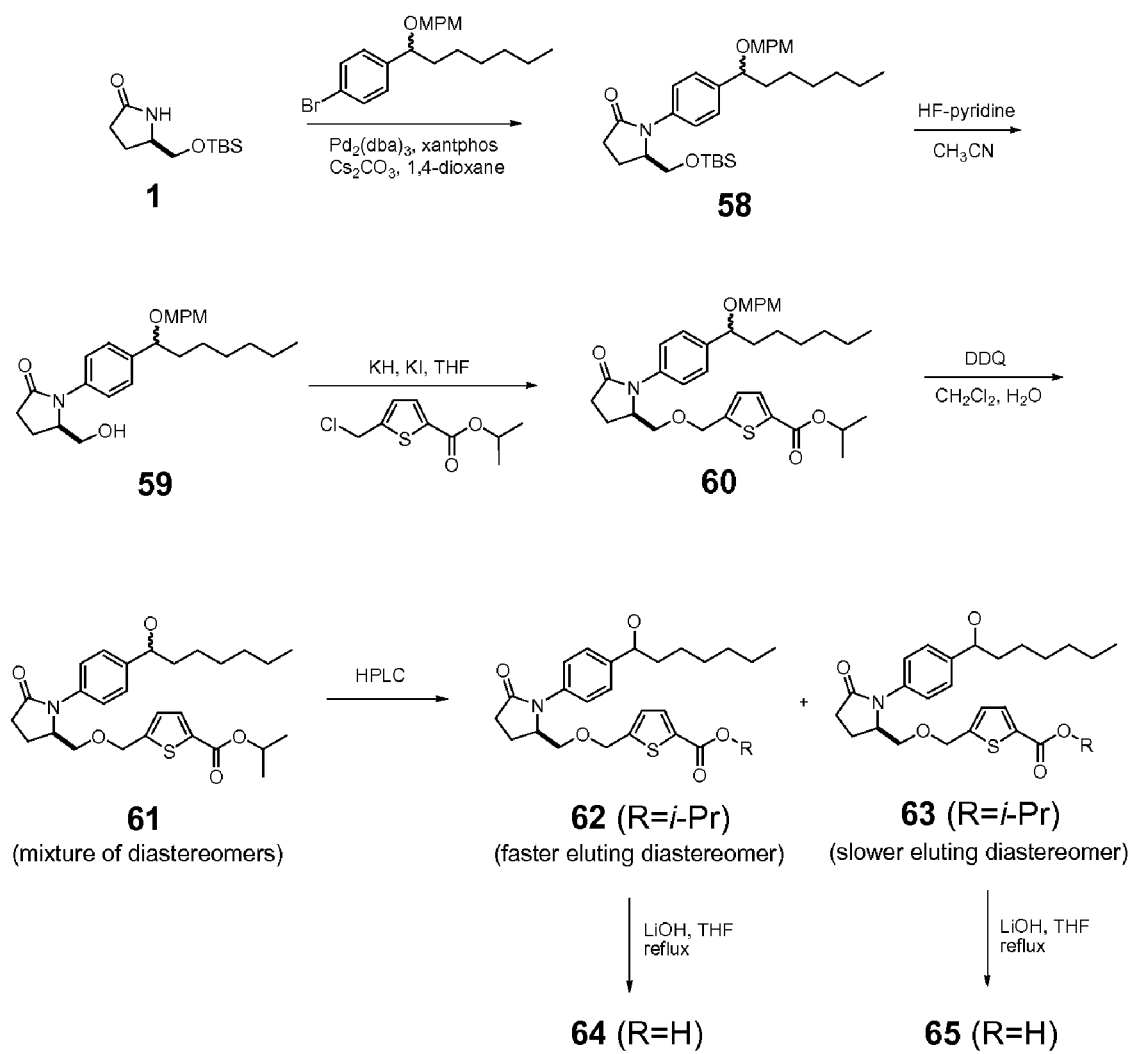
Figure 15:
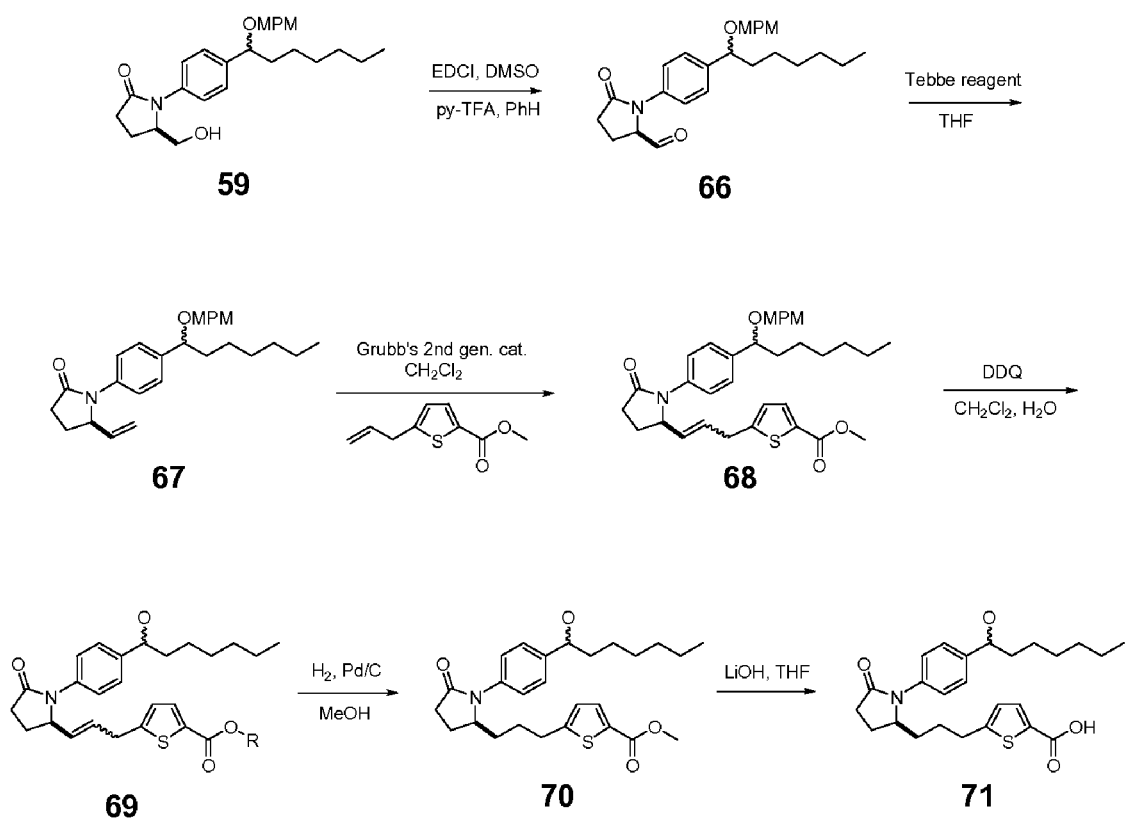
Figure 16:
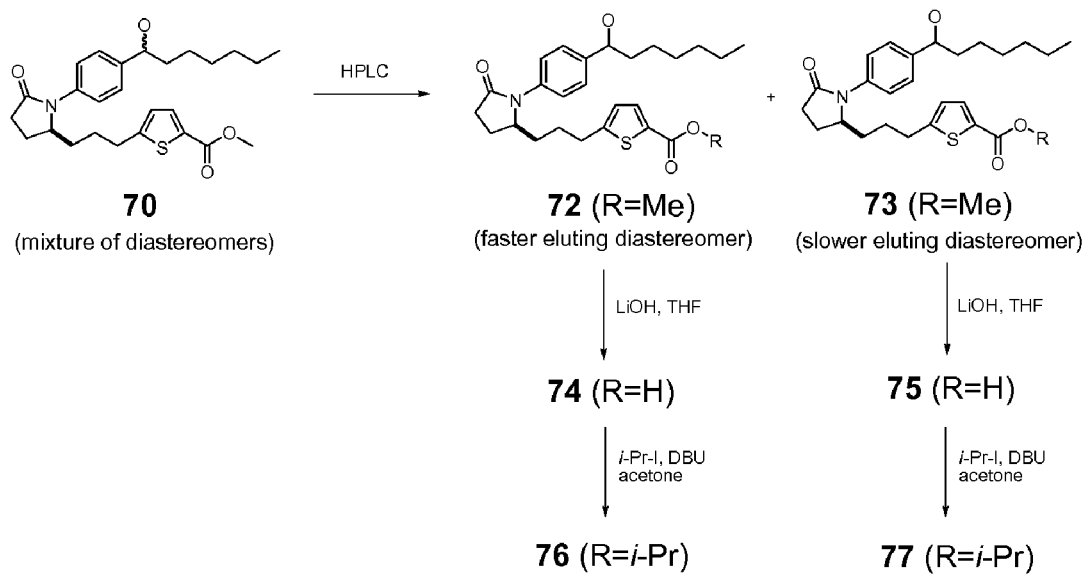
Figure 17:
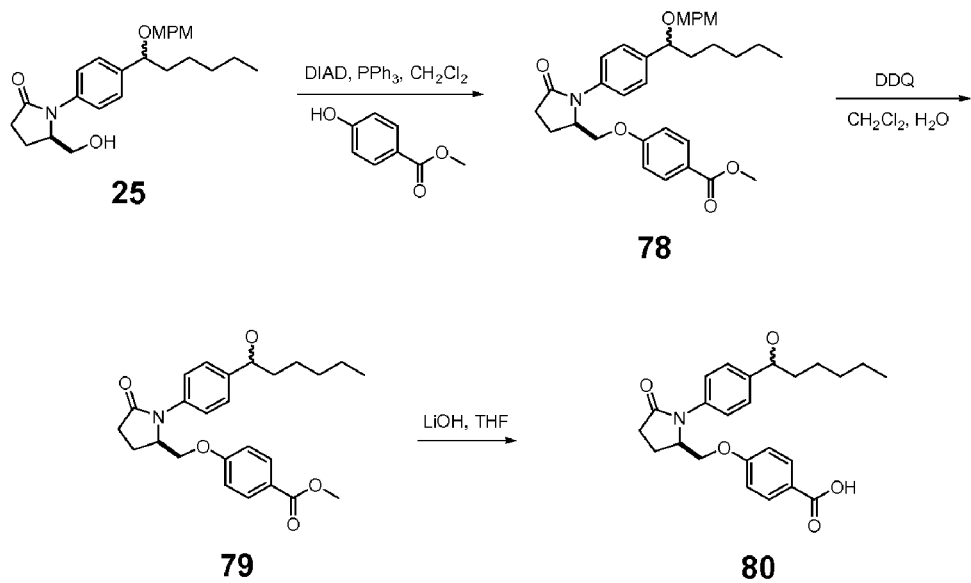

FIGS. 1-16 show examples of methods that can be used to prepare the compounds disclosed herein.

DESCRIPTION OF THE INVENTION

A compound is disclosed herein comprising

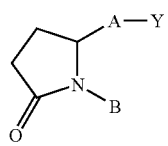

or a pharmaceutically acceptable salt, prodrug, or a metabolite thereof;
wherein Y is an organic acid functional group, or an amide or ester thereof comprising up to 12 carbon atoms; or Y is hydroxymethyl or an ether thereof comprising up to 12 carbon atoms; or
Y is a tetrazolyl functional group;
A is —$CH_2$)$_6$—, cis —$CH_2CH=CH$—($CH_2$)$_3$—, or —$CH_2C\equiv C$—($CH_2$)$_3$—, wherein 1 or 2 carbon atoms may be substituted with S or O; or A is —($CH_2$)$_m$—Ar—($CH_2$)$_o$— wherein Ar is interarylene or heterointerarylene, the sum of m and o is from 1 to 4, and wherein one $CH_2$ may be substituted with S or O; and
B is aryl or heteroaryl.

Y is an organic acid functional group, or an amide or ester thereof comprising up to 12 carbon atoms; or Y is hydroxymethyl or an ether thereof comprising up to 12 carbon atoms; or Y is a tetrazolyl functional group.

An organic acid functional group is an acidic functional group on an organic molecule. While not intending to be limiting, organic acid functional groups may comprise an oxide of carbon, sulfur, or phosphorous. Thus, while not intending to limit the scope of the invention in any way, in certain compounds Y is a carboxylic acid, sulfonic acid, or phosphonic acid functional group, i.e. one of the structures shown below.

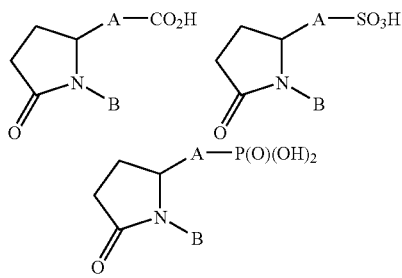

Salts of any of these acids of any pharmaceutically acceptable form are also contemplated.

In some embodiments, esters contemplated in the practice of the invention are $C_1$ to $C_6$ esters. In other embodiments, esters contemplated in the practice of the invention are $C_3$ esters. In certain embodiments, esters contemplated in the practice of the invention are isopropyl esters Additionally, an amide or ester of one of the organic acids shown above comprising up to 12 carbon atoms is also contemplated. In an ester, a hydrocarbyl moiety replaces a hydrogen atom of an acid such as in a carboxylic acid ester, e.g. $CO_2Me$, $CO_2Et$, etc.

In an amide, an amine group replaces an OH of the acid. Examples of amides include $CON(R^2)_2$, $CON(OR^2)R^2$, $CON(CH_2CH_2OH)_2$, and $CONH(CH_2CH_2OH)$ where $R^2$ is independently H, $C_1$-$C_6$ alkyl, phenyl, or biphenyl. Moieties such as $CONHSO_2R^2$ are also amides of the carboxylic acid notwithstanding the fact that they may also be considered to be amides of the sulfonic acid $R^2$—$SO_3H$.

While not intending to limit the scope of the invention in any way, Y may also be hydroxymethyl or an ether thereof comprising up to 12 carbon atoms. Thus, compounds having a structure shown below are possible.

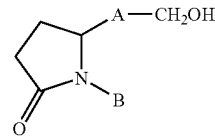

Additionally, ethers of these compounds are also possible. An ether is a functional group wherein a hydrogen of an hydroxyl is replaced by carbon, e.g., Y is $CH_2OCH_3$, $CH_2OCH_2CH_3$, etc.

Finally, while not intending to limit the scope of the invention in any way, Y may be a tetrazolyl functional group, such as compounds having a structure according to the formula below.

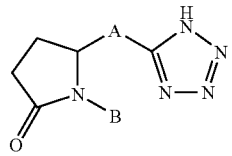

An unsubstituted tetrazolyl functional group has two tautomeric forms, which can rapidly interconvert in aqueous or biological media, and are thus equivalent to one another. These tautomers are shown below.

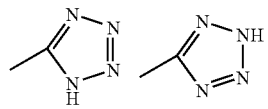

Additionally, if $R^2$ is $C_1$-$C_6$ alkyl, phenyl, or biphenyl, other isomeric forms of the tetrazolyl functional group such as the one shown below are also possible, unsubstituted and hydrocarbyl substituted tetrazolyl up to $C_{12}$ are considered to be within the scope of the term "tetrazolyl."

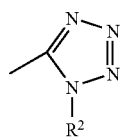

While not intending to limit the scope of the invention in any way, in one embodiment, Y is selected from the group consisting of $CO_2(R^2)$, $CON(R^2)_2$, $CON(OR^2)R^2$, $CON(CH_2CH_2OH)_2$, $CONH(CH_2CH_2OH)$, $CH_2OH$, $P(O)(OH)_2$, $CONHSO_2R^2$, $SO_2N(R^2)_2$, $SO_2NHR^2$, and tetrazolyl-$R^2$; wherein $R^2$ is independently H, $C_1$-$C_6$ alkyl, phenyl, or biphenyl.

In another embodiment Y is not CONH-phenyl or CONH-cyclohexyl.

In relation to the identity of A disclosed in the chemical structures presented herein, A is —$(CH_2)_6$—, cis —$CH_2CH$=$CH$—$(CH_2)_3$—, or —$CH_2C$≡$C$—$(CH_2)_3$—, wherein 1 or 2 carbon atoms may be substituted with S or O; or A is —$(CH_2)_m$—Ar—$(CH_2)_o$— wherein Ar is interarylene or heterointerarylene, the sum of m and o is from 1 to 4, and wherein one $CH_2$ may be substituted with S or O.

While not intending to be limiting, A may be —$(CH_2)_6$—, cis —$CH_2CH$=$CH$—$(CH_2)_3$—, or —$CH_2C$≡$C$—$(CH_2)_3$—.

Alternatively, A may be a group which is related to one of these three moieties in that any carbon is substituted with S and/or O. For example, while not intending to limit the scope of the invention in any way, A may be an S substituted moiety such as one of the following or the like.

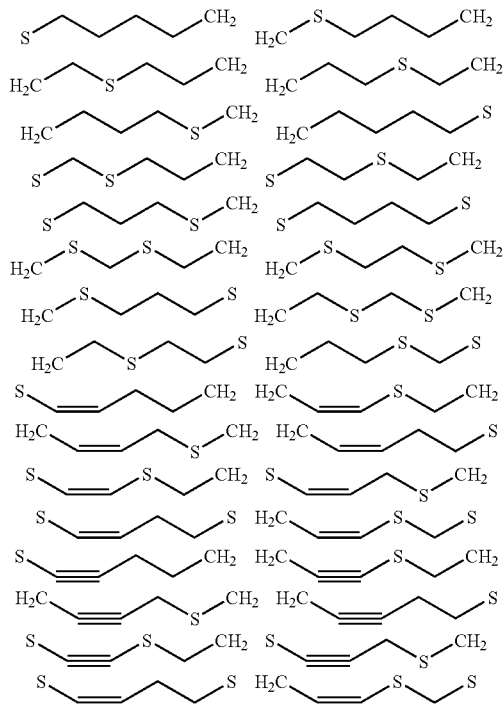

Alternatively, while not intending to limit the scope of the invention in any way, A may be an O substituted moiety such as one of the following or the like.

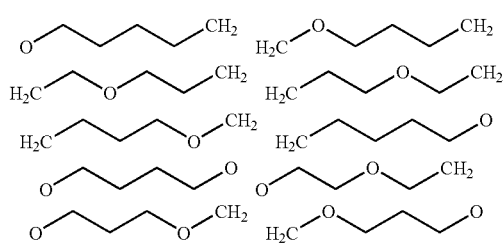

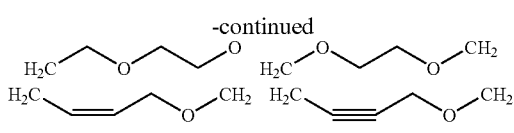

Alternatively, while not intending to limit the scope of the invention in any way, A may have both an O and an S substituted into the chain, such as one of the following or the like.

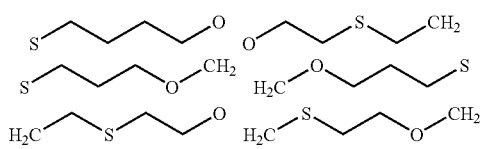

Alternatively, while not intending to limit the scope of the invention in any way, in certain embodiments A is —$(CH_2)_m$—Ar—$(CH_2)_o$— wherein Ar is interarylene or heterointerarylene, the sum of m and o is from 1 to 4, and wherein one $CH_2$ may be substituted with S or O. In other words, while not intending to limit the scope of the invention in any way, in one embodiment A comprises from 1 to 4 $CH_2$ moieties and Ar, e.g. —$CH_2$—Ar—, —$(CH_2)_2$—Ar—, —$CH_2$—Ar—$CH_2$—, —$CH_2$—Ar—$(CH_2)_2$—, —$(CH_2)_2$—Ar—$(CH_2)_2$—, and the like; or A comprises O, from 0 to 3 $CH_2$ moieties, and Ar, e.g., —O—Ar—, Ar—$CH_2$—O—, —O—Ar—$(CH_2)_2$—, —O—$CH_2$—Ar—, —O—$CH_2$—Ar—$(CH_2)_2$, and the like; or A comprises S, from 0 to 3 $CH_2$ moieties, and Ar, e.g., —S—Ar—, Ar—$CH_2$—S—, —S—Ar—$(CH_2)_2$—, —S—$CH_2$—Ar—, —S—$CH_2$—Ar—$(CH_2)_2$, —$(CH_2)_2$—S—Ar, and the like.

In another embodiment, the sum of m and o is from 2 to 4 wherein one $CH_2$ may be substituted with S or O.

In another embodiment, the sum of m and o is 3 wherein one $CH_2$ may be substituted with S or O.

In another embodiment, the sum of m and o is 2 wherein one $CH_2$ may be substituted with S or O.

In another embodiment, the sum of m and o is 4 wherein one $CH_2$ may be substituted with S or O.

Interarylene or heterointerarylene refers to an aryl ring or ring system or a heteroaryl ring or ring system which connects two other parts of a molecule, i.e. the two parts are bonded to the ring in two distinct ring positions. Interarylene or heterointerarylene may be substituted or unsubstituted. Unsubstituted interarylene or heterointerarylene has no substituents other than the two parts of the molecule it connects. Substituted interarylene or heterointerarylene has one or more substitutents in addition to the two parts of the molecule it connects.

In one embodiment, Ar is substituted or unsubstituted interphenylene, interthienylene, interfurylene, interpyridinylene, interoxazolylene, and interthiazolylene. In another embodiment Ar is interphenylene (Ph). In another embodiment A is —$(CH_2)_2$-Ph-. While not intending to limit scope of the invention in any way, substituents may have 4 or less heavy atoms, or in other words, non hydrogen atoms. Any number of hydrogen atoms required for a particular substituent will also be included. Thus, the substituent may be hydrocarbyl i.e. a moiety consisting of only carbon and hydrogen such as alkyl, having up to 4 carbon atoms, including alkyl up to $C_4$, alkenyl, alkynyl, and the like;

hydrocarbyloxy up to $C_3$;
CF$_3$;
halo, such as F, Cl, or Br;
hydroxyl;
NH$_2$ and alkylamine functional groups up to $C_3$;
other N or S containing substituents;
and the like.

Substituted interarylene or interheteroarylene may have one or more substituents, up to as many as the ring or ring system will bear, and the substituents may be the same or different. Thus, for example, an interarylene ring or interheteroarylene ring may be substituted with chloro and methyl; methyl, OH, and F; CN, NO$_2$, and ethyl; and the like including any conceivable substituent or combination of substituent possible in light of this disclosure.

In one embodiment A is —(CH$_2$)$_m$—Ar—(CH$_2$)$_o$— wherein Ar is interphenylene, the sum of m and o is from 1 to 3, and wherein one CH$_2$ may be substituted with S or O.

In another embodiment A is —CH$_2$—Ar—OCH$_2$—. In another embodiment A is —CH$_2$—Ar—OCH$_2$— and Ar is interphenylene. In another embodiment, Ar is 1,3 interaryl or interheteroaryl, where Ar attached at the 1 and 3 positions, such as when A has the structure shown below.

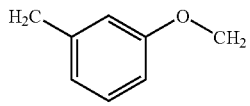

Other examples of 1,3 interaryl or interheteroaryl are exemplified in the following examples of A-Y.

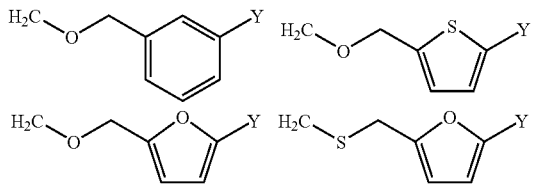

In another embodiment A is —(CH$_2$)$_6$—, cis —CH$_2$CH=CH—(CH$_2$)$_3$—, or —CH$_2$C≡C—(CH$_2$)$_3$—, wherein 1 or 2 carbon atoms may be substituted with S or O; or A is —(CH$_2$)$_2$-Ph- wherein one CH$_2$ may be substituted with S or O.

In another embodiment A is —(CH$_2$)$_6$—, cis —CH$_2$CH=CH—(CH$_2$)$_3$—, or —CH$_2$C≡C—(CH$_2$)$_3$—, wherein 1 or 2 carbon atoms may be substituted with S or O; or A is —(CH$_2$)$_2$-Ph-.

In another embodiment A is not —(CH$_2$)$_6$—.

In other embodiments, A has one of the following structures, where Y is attached to the oxazolyl or thiazolyl ring.

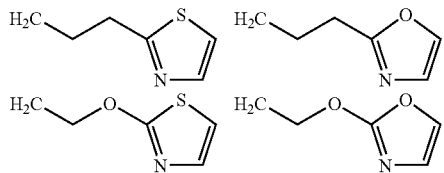

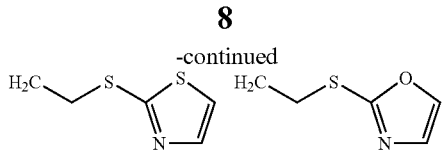

In other embodiments A is one of the structures shown below, where Y is attached to the phenyl or heteroaryl ring.

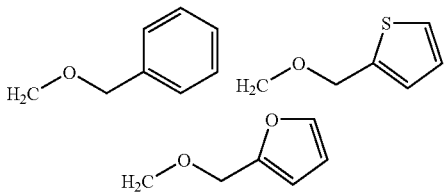

In another embodiment A is —CH$_2$OCH$_2$Ar.
In another embodiment A is —CH$_2$SCH$_2$Ar.
In another embodiment A is —(CH$_2$)$_3$Ar.
In another embodiment A is —CH$_2$O(CH$_2$)$_4$.
In another embodiment A is —CH$_2$S(CH$_2$)$_4$.
In another embodiment A is, —S(CH$_2$)$_3$S(CH$_2$)$_2$—.
In another embodiment A is, —(CH$_2$)$_4$OCH$_2$—.
In another embodiment A is, cis —CH$_2$CH=CH—CH$_2$OCH$_2$—.
In another embodiment A is, —CH$_2$CH≡CH—CH$_2$OCH$_2$—.
In another embodiment A is, —(CH$_2$)$_2$S(CH$_2$)$_3$—.
In another embodiment A is, —CH$_2$-Ph-OCH$_2$—, wherein Ph is interphenylene.
In another embodiment A is, —CH$_2$-mPh-OCH$_2$—, wherein mPh is m-interphenylene.
In another embodiment A is, —CH$_2$—O—(CH$_2$)$_4$—.
In another embodiment A is, —CH$_2$—O—CH$_2$—Ar—, wherein Ar is 2,5-interthienylene.
In another embodiment A is, —CH$_2$—O—CH$_2$—Ar—, wherein Ar is 2,5-interphenylene.

B is aryl or heteroaryl.
Aryl is an unsubstituted or substituted aromatic ring or ring system such as phenyl, naphthyl, biphenyl, and the like.
Heteroaryl is aryl having one or more N, O, or S atoms in the ring, i.e. a ring carbon is substituted by N, O, or S. While not intending to be limiting, examples of heteroaryl include unsubstituted or substituted thienyl, pyridinyl, furyl, benzothienyl, benzofuryl, imidizololyl, indolyl, and the like.

The substituents of aryl or heteroaryl may have up to 12 non-hydrogen atoms each and as many hydrogen atoms as necessary. Thus, while not intending to limit the scope of the invention in any way, the substituents may be:
hydrocarbyl, i.e. a moiety consisting of only carbon and hydrogen such as alkyl, alkenyl, alkynyl, and the like, including linear, branched or cyclic hydrocarbyl, and combinations thereof;
hydrocarbyloxy, meaning O-hydrocarbyl such as OCH$_3$, OCH$_2$CH$_3$, O-cyclohexyl, etc, up to 11 carbon atoms;
other ether substituents such as CH$_2$OCH$_3$, (CH$_2$)$_2$OCH(CH$_3$)$_2$, and the like;
thioether substituents including S-hydrocarbyl and other thioether substituents;
hydroxyhydrocarbyl, meaning hydrocarbyl-OH such as CH$_2$OH, C(CH$_3$)$_2$OH, etc, up to 11 carbon atoms;
nitrogen substituents such as NO$_2$, CN, and the like, including amino, such as NH$_2$, NH(CH$_2$CH$_3$OH), NHCH$_3$, and the like up to 11 carbon atoms;

carbonyl substituents, such as CO₂H, ester, amide, and the like;

halogen, such as chloro, fluoro, bromo, and the like fluorocarbyl, such as CF₃, CF₂CF₃, etc.;

phosphorous substituents, such as $PO_3^{2-}$, and the like;

sulfur substituents, including S-hydrocarbyl, SH, SO₃H, SO₂-hydrocarbyl, SO₃-hydrocarbyl, and the like.

In certain embodiments, the number of non-hydrogen atoms is 6 or less in a substituent. In other embodiments, the number of non-hydrogen atoms is 3 or less in a substituent. In other embodiments, the number of non-hydrogen atoms on a substituent is 1.

In certain embodiments, the substituents contain only hydrogen, carbon, oxygen, halogen, nitrogen, and sulfur. In other embodiments, the substituents contain only hydrogen, carbon, oxygen, and halogen.

Unless otherwise indicated, references to aryl, heteroaryl, phenyl, thienyl, benzothienyl, and the like are intended to mean both the substituted and the unsubstituted moiety.

Substituted aryl or heteroaryl may have one or more substituents, up to as many as the ring or ring system will bear, and the substituents may be the same or different. Thus, for example, an aryl ring or a heteroaryl ring may be substituted with chloro and methyl; methyl, OH, and F; CN, NO₂, and ethyl; and the like including any conceivable substituent or combination of substituent possible in light of this disclosure.

Thus, compounds wherein B is any of the above classes or species of aryl or heteroaryl are contemplated herein.

Further, while not intending to limit the scope of the invention in any way, in one embodiment B is phenyl. In another embodiment B is chlorophenyl, meaning phenyl with one or more chloro substituents. In another embodiment D is 3,5-dichlorophenyl. In another embodiment B is unsubstituted phenyl. In another embodiment B is alkylphenyl. In another embodiment B is t-butylphenyl.

In another embodiment B is not unsubstituted phenyl. In another embodiment B is not chlorophenyl. In another embodiment B is not fluorophenyl. In another embodiment B is not dimethylaminophenyl. In another embodiment B is not unsubstituted phenyl, chlorophenyl, fluorophenyl, or dimethylaminophenyl.

In another embodiment B is hydroxyalkylphenyl, meaning phenyl with a hydroxyalkyl substitutent such as Ph-CH(OH)C(CH₃)₃.

B can also be any of the groups shown below, where the remainder of the molecule attaches to the phenyl ring. The names of these moieties are shown to the right of the structure.

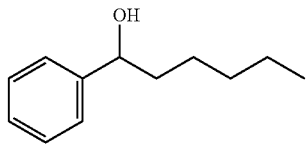
(1-hydroxyhexyl)phenyl

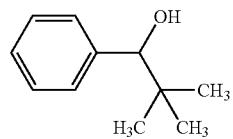
(1-hydroxy-2,2-dimethylpropyl)phenyl

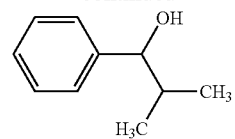
(1-hydroxy-2-methylpropyl)phenyl

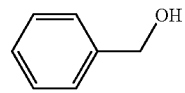
(hydroxymethyl)phenyl

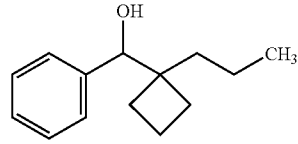
[(1-propylcyclobutyl)hydroxymethyl]phenyl

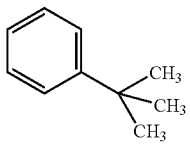
t-butylphenyl

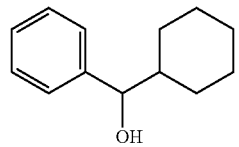
(cyclohexylhydroxymethyl)phenyl

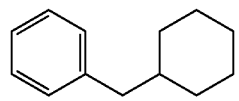
(cyclohexylmethyl)phenyl

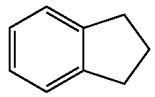
indanyl

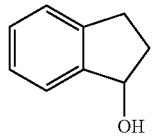
indanolyl

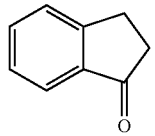
indanonyl

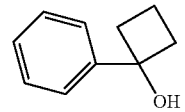
(1-hydroxycyclobutyl)phenyl

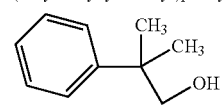
(2-methyl-3-hydroxypropyl)phenyl

-continued

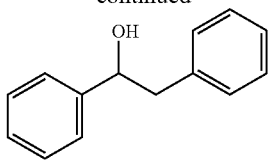

(1-hydroxy-2-phenylethyl)phenyl

One compound comprises

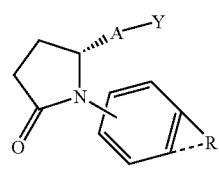

or a pharmaceutically acceptable salt, prodrug, or a metabolite thereof;
wherein a dashed line indicates the presence or absence of a bond
R is hydrocarbyl or hydroxyhydrocarbyl having from 1 to 12 carbon atoms.

Another embodiment comprises

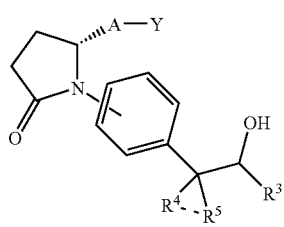

or a pharmaceutically acceptable salt, prodrug, or a metabolite thereof;
wherein a dashed line indicates the presence or absence of a bond;
$R^3$, $R^4$, and $R^5$ are independently H or $C_{1-6}$ alkyl.

As the dashed line indicates the presence or absence of a bond, $R^4$ and $R^5$ may be two separate moieties. For example, while not intending to be limiting, in one embodiment $R^4$ and $R^5$ is methyl, and no bond is present where indicated by the dashed line.

For example, a compound according to the formula below

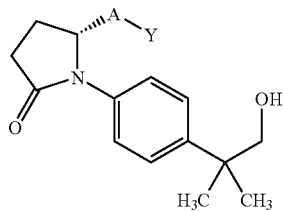

or a pharmaceutically acceptable salt, prodrug, or a metabolite thereof is contemplated. Alternatively, while not intending to limit the scope of the invention in any way, $R^4$ and $R^5$ may form a ring. In other words, a compound such as the one shown below is possible, wherein x is from 1 to 6.

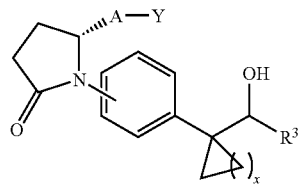

A pharmaceutically acceptable salt, prodrug, or a metabolite thereof is also contemplated.

Another embodiment comprises

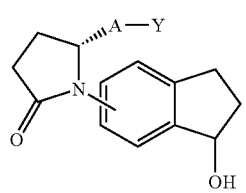

A pharmaceutically acceptable salt, prodrug, or a metabolite thereof is also contemplated.

Other useful compounds comprise

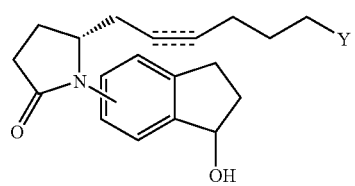

A pharmaceutically acceptable salt, prodrug, or a metabolite thereof is also contemplated.

Other useful examples of compounds comprise

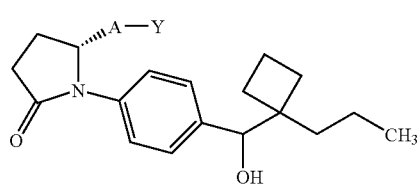

or a pharmaceutically acceptable salt, prodrug, or a metabolite thereof.

Other compounds comprise

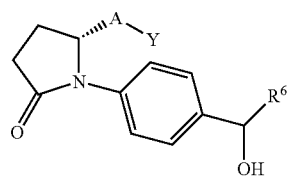

or a pharmaceutically acceptable salt, prodrug, or a metabolite thereof,
wherein $R^6$ is cycloalkyl comprising from 3 to 10 carbon atoms.

Other compounds comprise

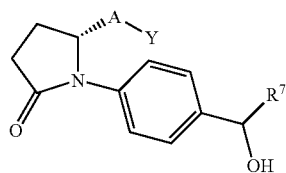

or a pharmaceutically acceptable salt, prodrug, or a metabolite thereof, wherein $R^7$ is linear alkyl comprising from 3 to 7 carbon atoms.

Other compounds comprise

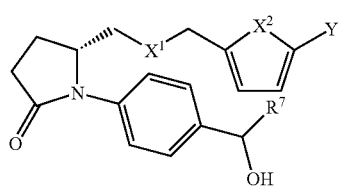

or a pharmaceutically acceptable salt, prodrug, or a metabolite thereof, wherein $X^1$ and $X^2$ are independently CH, O, or S; and $R^7$ is linear alkyl comprising from 3 to 7 carbon atoms.

Other compounds comprise

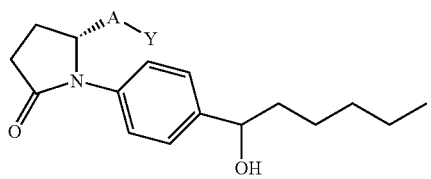

or a pharmaceutically acceptable salt, prodrug, or a metabolite thereof.

Other compounds comprise

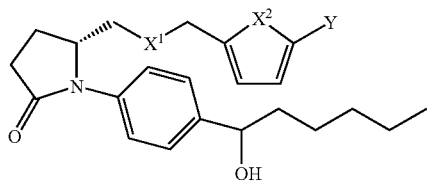

or a pharmaceutically acceptable salt, prodrug, or a metabolite thereof, wherein $X^1$ and $X^2$ are independently CH, O, or S.

Other compounds comprise

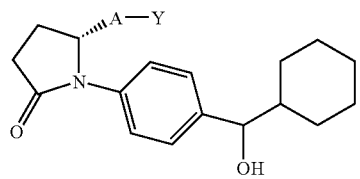

or a pharmaceutically acceptable salt, prodrug, or a metabolite thereof.

Other compounds comprise

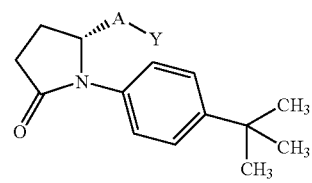

or a pharmaceutically acceptable salt, prodrug, or a metabolite thereof.

Another useful compound is

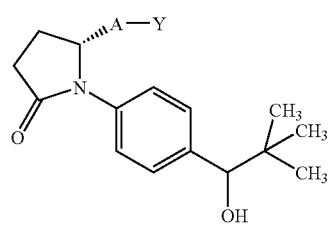

or a pharmaceutically acceptable salt, prodrug, or a metabolite thereof.

Another useful compound is

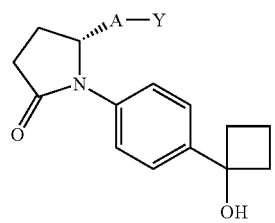

or a pharmaceutically acceptable salt, prodrug, or a metabolite thereof.

In one embodiment, a compound comprising

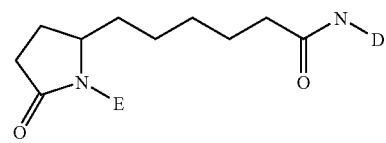

is not used, wherein

D is phenyl or cyclohexyl; and

E is unsubstituted phenyl, chlorophenyl, fluorophenyl, or dimethylaminophenyl.

Another compound comprises

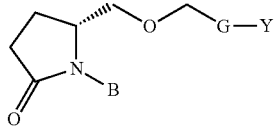

or a pharmaceutically acceptable salt, prodrug, or a metabolite thereof;
wherein G is 1,3-interaryl or interheteroaryl, or —$(CH_2)_3$—.

Another compound comprises

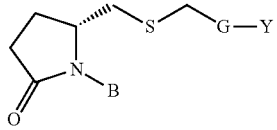

or a pharmaceutically acceptable salt, prodrug, or a metabolite thereof;
wherein G is 1,3-interaryl or interheteroaryl, or —$(CH_2)_3$—.

Another compound comprises

or a pharmaceutically acceptable salt, prodrug, or a metabolite thereof;
wherein a dashed line indicates the presence or absence of a bond;
R is hydrocarbyl or hydroxyhydrocarbyl having from 1 to 12 carbon atoms;
X is $CH_2$, O, or S; and
G is 1,3-interaryl or interheteroaryl, or —$(CH_2)_3$—.

Another compound is an N-aryl or N-heteroaryl gamma lactam which is active at a prostaglandin receptor. This compound may or may not incorporate any other structural limitation disclosed herein.

Another compound is an N-aryl or N-heteroaryl gamma lactam which is selectively active at a prostaglandin $EP_2$ receptor. This compound may or may not incorporate any other structural limitation disclosed herein.

Another compound is an N-aryl or N-heteroaryl gamma lactam which is effective at reducing intraocular pressure in a mammal. This compound may or may not incorporate any other structural limitation disclosed herein.

The determination of whether a compound is active at a prostaglandin receptor is well within the ability of a person of ordinary skill in the art. The determination of whether a compound is active at a prostaglandin $EP_2$ receptor is also well within the ability of a person of ordinary skill in the art. While not intending to limit the scope of the invention in any way, one method of making such determinations is also provided in the examples herein.

The determination of whether a compound is effective at reducing intraocular pressure in a mammal is well within the ability of a person of ordinary skill in the art. While not intending to limit the scope of the invention in any way, methods of determining whether a compound is effective in reducing intraocular pressure are given for a few exemplary mammals herein.

While not intending to limit the scope of the invention in any way, examples of useful compounds are depicted below, and pharmaceutically acceptable salts, prodrugs, or metabolites thereof.

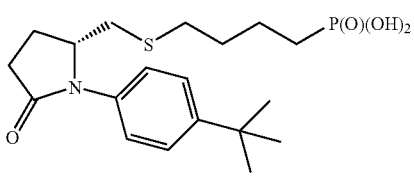

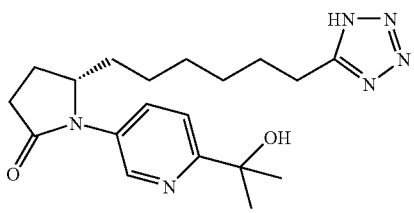

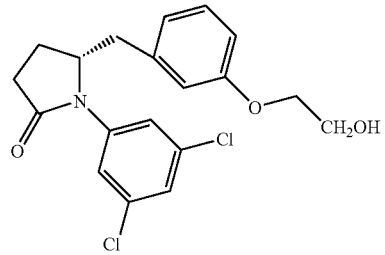

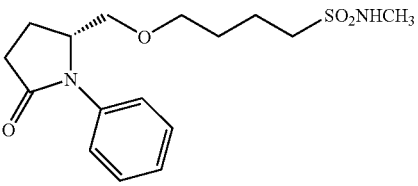

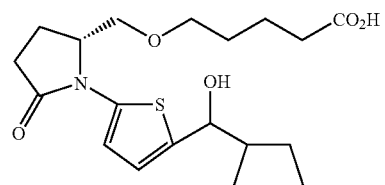

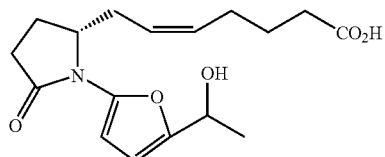

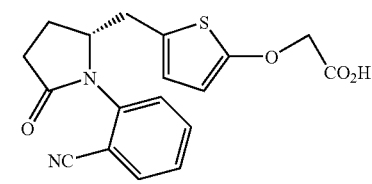

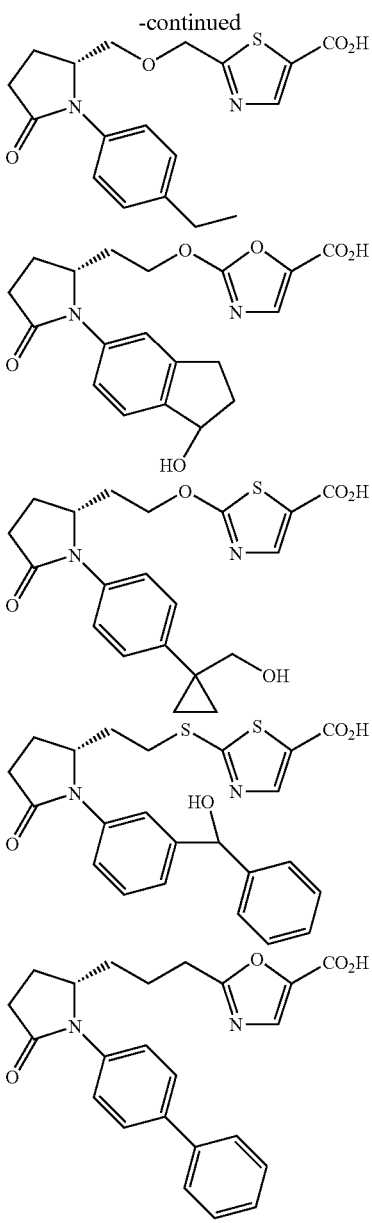

In one embodiment A is —S(CH$_2$)$_3$S(CH$_2$)$_2$— and B is phenyl.

In another embodiment A is —(CH$_2$)$_4$OCH$_2$— and B is phenyl.

In another embodiment A is cis —CH$_2$CH═CH—CH$_2$OCH$_2$— and B is phenyl.

In another embodiment A is —CH$_2$CH≡CH—CH$_2$OCH$_2$— and B is phenyl.

In another embodiment A is —(CH$_2$)$_2$S(CH$_2$)$_3$— and B is phenyl.

In another embodiment A is —CH$_2$-Ph-OCH$_2$—, wherein Ph is interphenylene, and B is phenyl.

In another embodiment A is —CH$_2$-mPh-OCH$_2$—, wherein mPh is m-interphenylene, and B is phenyl.

In another embodiment A is —CH$_2$—O—(CH$_2$)$_4$— and B is phenyl.

In another embodiment A is —CH$_2$—O—CH$_2$—Ar—, wherein Ar is 2,5-interthienylene, and B is phenyl.

In another embodiment A is —CH$_2$—O—CH$_2$—Ar—, wherein Ar is 2,5-interfurylene, and B is phenyl.

As mentioned before, phenyl in the above embodiments means substituted or unsubstituted phenyl unless indicated otherwise.

In one embodiment A is —S(CH$_2$)$_3$S(CH$_2$)$_2$— and B is (1-hydroxyhexyl)phenyl.

In another embodiment A is —(CH$_2$)$_4$OCH$_2$— and B is (1-hydroxyhexyl)phenyl.

In another embodiment A is cis —CH$_2$CH═CH—CH$_2$OCH$_2$— and B is (1-hydroxyhexyl)phenyl.

In another embodiment A is —CH$_2$CH≡CH—CH$_2$OCH$_2$— and B is (1-hydroxyhexyl)phenyl.

In another embodiment A is —(CH$_2$)$_2$S(CH$_2$)$_3$— and B is (1-hydroxyhexyl)phenyl.

In another embodiment A is —CH$_2$-Ph-OCH$_2$—, wherein Ph is interphenylene, and B is (1-hydroxyhexyl)phenyl.

In another embodiment A is —CH$_2$-mPh-OCH$_2$—, wherein mPh is m-interphenylene, and B is (1-hydroxyhexyl)phenyl.

In another embodiment A is —CH$_2$—O—(CH$_2$)$_4$— and B is (1-hydroxyhexyl)phenyl.

In another embodiment A is —CH$_2$—O—CH$_2$—Ar—, wherein Ar is 2,5-interthienylene, and B is (1-hydroxyhexyl)phenyl.

In another embodiment A is —CH$_2$—O—CH$_2$—Ar—, wherein Ar is 2,5-interfurylene, and B is (1-hydroxyhexyl)phenyl.

In another embodiment A is —S(CH$_2$)$_3$S(CH$_2$)$_2$— and B is (1-hydroxy-2,2-dimethylpropyl)phenyl.

In another embodiment A is —(CH$_2$)$_4$OCH$_2$— and B is (1-hydroxy-2,2-dimethylpropyl)phenyl.

In another embodiment A is cis —CH$_2$CH═CH—CH$_2$OCH$_2$— and B is (1-hydroxy-2,2-dimethylpropyl)phenyl.

In another embodiment A is —CH$_2$CH≡CH—CH$_2$OCH$_2$— and B is (1-hydroxy-2,2-dimethylpropyl)phenyl.

In another embodiment A is —(CH$_2$)$_2$S(CH$_2$)$_3$— and B is (1-hydroxy-2,2-dimethylpropyl)phenyl.

In another embodiment A is —CH$_2$-Ph-OCH$_2$—, wherein Ph is interphenylene, and B is (1-hydroxy-2,2-dimethylpropyl)phenyl.

In another embodiment A is —CH$_2$-mPh-OCH$_2$—, wherein mPh is m-interphenylene, and B is (1-hydroxy-2,2-dimethylpropyl)phenyl.

In another embodiment A is —CH$_2$—O—(CH$_2$)$_4$— and B is (1-hydroxy-2,2-dimethylpropyl)phenyl.

In another embodiment A is —CH$_2$—O—CH$_2$—Ar—, wherein Ar is 2,5-interthienylene, and B is (1-hydroxy-2,2-dimethylpropyl)phenyl.

In another embodiment A is —CH$_2$—O—CH$_2$—Ar—, wherein Ar is 2,5-interfurylene, and B is (1-hydroxy-2,2-dimethylpropyl)phenyl.

In another embodiment A is —S(CH$_2$)$_3$S(CH$_2$)$_2$— and B is (1-hydroxy-2-methylpropyl)phenyl.

In another embodiment A is —(CH$_2$)$_4$OCH$_2$— and B is (1-hydroxy-2-methylpropyl)phenyl.

In another embodiment A is cis —CH$_2$CH═CH—CH$_2$OCH$_2$— and B is (1-hydroxy-2-methylpropyl)phenyl.

In another embodiment A is —CH$_2$CH≡CH—CH$_2$OCH$_2$— and B is (1-hydroxy-2-methylpropyl)phenyl.

In another embodiment A is —(CH$_2$)$_2$S(CH$_2$)$_3$— and B is (1-hydroxy-2-methylpropyl)phenyl.

In another embodiment A is —CH$_2$-Ph-OCH$_2$—, wherein Ph is interphenylene, and B is (1-hydroxy-2-methylpropyl)phenyl.

In another embodiment A is —CH$_2$-mPh-OCH$_2$—, wherein mPh is m-interphenylene, and B is (1-hydroxy-2-methylpropyl)phenyl.

In another embodiment A is —CH$_2$—O—(CH$_2$)$_4$— and B is (1-hydroxy-2-methylpropyl)phenyl.

In another embodiment A is —CH$_2$—O—CH$_2$—Ar—, wherein Ar is 2,5-interthienylene, and B is (1-hydroxy-2-methylpropyl)phenyl.

In another embodiment A is —CH$_2$—O—CH$_2$—Ar—, wherein Ar is 2,5-interfurylene, and B is (1-hydroxy-2-methylpropyl)phenyl.

In another embodiment A is —S(CH$_2$)$_3$S(CH$_2$)$_2$— and B is (hydroxymethyl)phenyl.

In another embodiment A is —(CH$_2$)$_4$OCH$_2$— and B is (hydroxymethyl)phenyl.

In another embodiment A is cis —CH$_2$CH═CH—CH$_2$OCH$_2$— and B is (hydroxymethyl)phenyl.

In another embodiment A is —CH$_2$CH≡CH—CH$_2$OCH$_2$— and B is (hydroxymethyl)phenyl.

In another embodiment A is —(CH$_2$)$_2$S(CH$_2$)$_3$— and B is (hydroxymethyl)phenyl.

In another embodiment A is —CH$_2$-Ph-OCH$_2$—, wherein Ph is interphenylene, and B is (hydroxymethyl)phenyl.

In another embodiment A is —CH$_2$-mPh-OCH$_2$—, wherein mPh is m-interphenylene, and B is (hydroxymethyl)phenyl.

In another embodiment A is —CH$_2$—O—(CH$_2$)$_4$— and B is (hydroxymethyl)phenyl.

In another embodiment A is —CH$_2$—O—CH$_2$—Ar—, wherein Ar is 2,5-interthienylene, and B is (hydroxymethyl)phenyl.

In another embodiment A is —CH$_2$—O—CH$_2$—Ar—, wherein Ar is 2,5-interfurylene, and B is (hydroxymethyl)phenyl.

In another embodiment A is —S(CH$_2$)$_3$S(CH$_2$)$_2$— and B is [(1-propylcyclobutyl)hydroxymethyl]phenyl.

In another embodiment A is —(CH$_2$)$_4$OCH$_2$— and B is [(1-propylcyclobutyl)hydroxymethyl]phenyl.

In another embodiment A is cis —CH$_2$CH═CH—CH$_2$OCH$_2$— and B is [(1-propylcyclobutyl)hydroxymethyl]phenyl.

In another embodiment A is —CH$_2$CH≡CH—CH$_2$OCH$_2$— and B is [(1-propylcyclobutyl)hydroxymethyl]phenyl.

In another embodiment A is —(CH$_2$)$_2$S(CH$_2$)$_3$— and B is [(1-propylcyclobutyl)hydroxymethyl]phenyl.

In another embodiment A is —CH$_2$-Ph-OCH$_2$—, wherein Ph is interphenylene, and B is [(1-propylcyclobutyl)hydroxymethyl]phenyl.

In another embodiment A is —CH$_2$-mPh-OCH$_2$—, wherein mPh is m-interphenylene, and B is [(1-propylcyclobutyl)hydroxymethyl]phenyl.

In another embodiment A is —CH$_2$—O—(CH$_2$)$_4$— and B is [(1-propylcyclobutyl)hydroxymethyl]phenyl.

In another embodiment A is —CH$_2$—O—CH$_2$—Ar—, wherein Ar is 2,5-interthienylene, and B is [(1-propylcyclobutyl)hydroxymethyl]phenyl.

In another embodiment A is —CH$_2$—O—CH$_2$—Ar—, wherein Ar is 2,5-interfurylene, and B is [(1-propylcyclobutyl)hydroxymethyl]phenyl.

In another embodiment A is —S(CH$_2$)$_3$S(CH$_2$)$_2$— and B is t-butylphenyl.

In another embodiment A is —(CH$_2$)$_4$OCH$_2$— and B is t-butylphenyl.

In another embodiment A is cis —CH$_2$CH═CH—CH$_2$OCH$_2$— and B is t-butylphenyl.

In another embodiment A is —CH$_2$CH≡CH—CH$_2$OCH$_2$— and B is t-butylphenyl.

In another embodiment A is —(CH$_2$)$_2$S(CH$_2$)$_3$— and B is t-butylphenyl.

In another embodiment A is —CH$_2$-Ph-OCH$_2$—, wherein Ph is interphenylene, and B is t-butylphenyl.

In another embodiment A is —CH$_2$-mPh-OCH$_2$—, wherein mPh is m-interphenylene, and B is t-butylphenyl.

In another embodiment A is —CH$_2$—O—(CH$_2$)$_4$— and B is t-butylphenyl.

In another embodiment A is —CH$_2$—O—CH$_2$—Ar—, wherein Ar is 2,5-interthienylene, and B is t-butylphenyl.

In another embodiment A is —CH$_2$—O—CH$_2$—Ar—, wherein Ar is 2,5-interfurylene, and B is t-butylphenyl.

In another embodiment A is —S(CH$_2$)$_3$S(CH$_2$)$_2$— and B is (cyclohexylhydroxymethyl)phenyl.

In another embodiment A is —(CH$_2$)$_4$OCH$_2$— and B is (cyclohexylhydroxymethyl)phenyl.

In another embodiment A is cis —CH$_2$CH═CH—CH$_2$OCH$_2$— and B is (cyclohexylhydroxymethyl)phenyl.

In another embodiment A is —CH$_2$CH≡CH—CH$_2$OCH$_2$— and B is (cyclohexylhydroxymethyl)phenyl.

In another embodiment A is —(CH$_2$)$_2$S(CH$_2$)$_3$— and B is (cyclohexylhydroxymethyl)phenyl.

In another embodiment A is —CH$_2$-Ph-OCH$_2$—, wherein Ph is interphenylene, and B is (cyclohexylhydroxymethyl)phenyl.

In another embodiment A is —CH$_2$-mPh-OCH$_2$—, wherein mPh is m-interphenylene, and B is (cyclohexylhydroxymethyl)phenyl.

In another embodiment A is —CH$_2$—O—(CH$_2$)$_4$— and B is (cyclohexylhydroxymethyl)phenyl.

In another embodiment A is —CH$_2$—O—CH$_2$—Ar—, wherein Ar is 2,5-interthienylene, and B is (cyclohexylhydroxymethyl)phenyl.

In another embodiment A is —CH$_2$—O—CH$_2$—Ar—, wherein Ar is 2,5-interfurylene, and B is (cyclohexylhydroxymethyl)phenyl.

In another embodiment A is —S(CH$_2$)$_3$S(CH$_2$)$_2$— and B is (cyclohexylmethyl)phenyl.

In another embodiment A is —(CH$_2$)$_4$OCH$_2$— and B is (cyclohexylmethyl)phenyl.

In another embodiment A is cis —CH$_2$CH═CH—CH$_2$OCH$_2$— and B is (cyclohexylmethyl)phenyl.

In another embodiment A is —CH$_2$CH≡CH—CH$_2$OCH$_2$— and B is (cyclohexylmethyl)phenyl.

In another embodiment A is —(CH$_2$)$_2$S(CH$_2$)$_3$— and B is (cyclohexylmethyl)phenyl.

In another embodiment A is —CH$_2$-Ph-OCH$_2$—, wherein Ph is interphenylene, and B is (cyclohexylmethyl)phenyl.

In another embodiment A is —CH$_2$-mPh-OCH$_2$—, wherein mPh is m-interphenylene, and B is (cyclohexylmethyl)phenyl.

In another embodiment A is —CH$_2$—O—(CH$_2$)$_4$— and B is (cyclohexylmethyl)phenyl.

In another embodiment A is —CH$_2$—O—CH$_2$—Ar—, wherein Ar is 2,5-interthienylene, and B is (cyclohexylmethyl)phenyl.

In another embodiment A is —CH$_2$—O—CH$_2$—Ar—, wherein Ar is 2,5-interfurylene, and B is (cyclohexylmethyl)phenyl.

In another embodiment A is —S(CH$_2$)$_3$S(CH$_2$)$_2$— and B is indanyl.

In another embodiment A is —(CH$_2$)$_4$OCH$_2$— and B is indanyl.

In another embodiment A is cis —CH$_2$CH═CH—CH$_2$OCH$_2$— and B is indanyl.

In another embodiment A is —CH$_2$CH≡CH—CH$_2$OCH$_2$— and B is indanyl.

In another embodiment A is —(CH$_2$)$_2$S(CH$_2$)$_3$— and B is indanyl.

In another embodiment A is —CH$_2$-Ph-OCH$_2$—, wherein Ph is interphenylene, and B is indanyl.

In another embodiment A is —CH$_2$-mPh-OCH$_2$—, wherein mPh is m-interphenylene, and B is indanyl.

In another embodiment A is —CH$_2$—O—(CH$_2$)$_4$— and B is indanyl.

In another embodiment A is —CH$_2$—O—CH$_2$—Ar—, wherein Ar is 2,5-interthienylene, and B is indanyl.

In another embodiment A is —CH$_2$—O—CH$_2$—Ar—, wherein Ar is 2,5-interfurylene, and B is indanyl.

In another embodiment A is —S(CH$_2$)$_3$S(CH$_2$)$_2$— and B is indanolyl.

In another embodiment A is —(CH$_2$)$_4$OCH$_2$— and B is indanolyl.

In another embodiment A is cis —CH$_2$CH═CH—CH$_2$OCH$_2$— and B is indanolyl.

In another embodiment A is —CH$_2$CH≡CH—CH$_2$OCH$_2$— and B is indanolyl.

In another embodiment A is —(CH$_2$)$_2$S(CH$_2$)$_3$— and B is indanolyl.

In another embodiment A is —CH$_2$-Ph-OCH$_2$—, wherein Ph is interphenylene, and B is indanolyl.

In another embodiment A is —CH$_2$-mPh-OCH$_2$—, wherein mPh is m-interphenylene, and B is indanolyl.

In another embodiment A is —CH$_2$—O—(CH$_2$)$_4$— and B is indanolyl.

In another embodiment A is —CH$_2$—O—CH$_2$—Ar—, wherein Ar is 2,5-interthienylene, and B is indanolyl.

In another embodiment A is —CH$_2$—O—CH$_2$—Ar—, wherein Ar is 2,5-interfurylene, and B is indanolyl.

In another embodiment A is —S(CH$_2$)$_3$S(CH$_2$)$_2$— and B is indanonyl.

In another embodiment A is —(CH$_2$)$_4$OCH$_2$— and B is indanonyl.

In another embodiment A is cis —CH$_2$CH═CH—CH$_2$OCH$_2$— and B is indanonyl.

In another embodiment A is —CH$_2$CH≡CH—CH$_2$OCH$_2$— and B is indanonyl.

In another embodiment A is —(CH$_2$)$_2$S(CH$_2$)$_3$— and B is indanonyl.

In another embodiment A is —CH$_2$-Ph-OCH$_2$—, wherein Ph is interphenylene, and B is indanonyl.

In another embodiment A is —CH$_2$-mPh-OCH$_2$—, wherein mPh is m-interphenylene, and B is indanonyl.

In another embodiment A is —CH$_2$—O—(CH$_2$)$_4$— and B is indanonyl.

In another embodiment A is —CH$_2$—O—CH$_2$—Ar—, wherein Ar is 2,5-interthienylene, and B is indanonyl.

In another embodiment A is —CH$_2$—O—CH$_2$—Ar—, wherein Ar is 2,5-interfurylene, and B is indanonyl.

In another embodiment A is —S(CH$_2$)$_3$S(CH$_2$)$_2$— and B is (1-hydroxycyclobutyl)phenyl.

In another embodiment A is —(CH$_2$)$_4$OCH$_2$— and B is (1-hydroxycyclobutyl)phenyl.

In another embodiment A is cis —CH$_2$CH═CH—CH$_2$OCH$_2$— and B is (1-hydroxycyclobutyl)phenyl.

In another embodiment A is —CH$_2$CH≡CH—CH$_2$OCH$_2$— and B is (1-hydroxycyclobutyl)phenyl.

In another embodiment A is —(CH$_2$)$_2$S(CH$_2$)$_3$— and B is (1-hydroxycyclobutyl)phenyl.

In another embodiment A is —CH$_2$-Ph-OCH$_2$—, wherein Ph is interphenylene, and B is (1-hydroxycyclobutyl)phenyl.

In another embodiment A is —CH$_2$-mPh-OCH$_2$—, wherein mPh is m-interphenylene, and B is (1-hydroxycyclobutyl)phenyl.

In another embodiment A is —CH$_2$—O—(CH$_2$)$_4$— and B is (1-hydroxycyclobutyl)phenyl.

In another embodiment A is —CH$_2$—O—CH$_2$—Ar—, wherein Ar is 2,5-interthienylene, and B is (1-hydroxycyclobutyl)phenyl.

In another embodiment A is —CH$_2$—O—CH$_2$—Ar—, wherein Ar is 2,5-interfurylene, and B is (1-hydroxycyclobutyl)phenyl.

In another embodiment A is —S(CH$_2$)$_3$S(CH$_2$)$_2$— and B is (2-methyl-3-hydroxypropyl)phenyl.

In another embodiment A is —(CH$_2$)$_4$OCH$_2$— and B is (2-methyl-3-hydroxypropyl)phenyl.

In another embodiment A is cis —CH$_2$CH═CH—CH$_2$OCH$_2$— and B is (2-methyl-3-hydroxypropyl)phenyl.

In another embodiment A is —CH$_2$CH≡CH—CH$_2$OCH$_2$— and B is (2-methyl-3-hydroxypropyl)phenyl.

In another embodiment A is —(CH$_2$)$_2$S(CH$_2$)$_3$— and B is (2-methyl-3-hydroxypropyl)phenyl.

In another embodiment A is —CH$_2$-Ph-OCH$_2$—, wherein Ph is interphenylene, and B is (2-methyl-3-hydroxypropyl)phenyl.

In another embodiment A is —CH$_2$-mPh-OCH$_2$—, wherein mPh is m-interphenylene, and B is (2-methyl-3-hydroxypropyl)phenyl.

In another embodiment A is —CH$_2$—O—(CH$_2$)$_4$— and B is (2-methyl-3-hydroxypropyl)phenyl.

In another embodiment A is —CH$_2$—O—CH$_2$—Ar—, wherein Ar is 2,5-interthienylene, and B is (2-methyl-3-hydroxypropyl)phenyl.

In another embodiment A is —CH$_2$—O—CH$_2$—Ar—, wherein Ar is 2,5-interfurylene, and B is (2-methyl-3-hydroxypropyl)phenyl.

In another embodiment A is —S(CH$_2$)$_3$S(CH$_2$)$_2$— and B is (1-hydroxy-2-phenylethyl)phenyl.

In another embodiment A is —(CH$_2$)$_4$OCH$_2$— and B is (1-hydroxy-2-phenylethyl)phenyl.

In another embodiment A is cis —CH$_2$CH═CH—CH$_2$OCH$_2$— and B is (1-hydroxy-2-phenylethyl)phenyl.

In another embodiment A is —CH$_2$CH≡CH—CH$_2$OCH$_2$— and B is (1-hydroxy-2-phenylethyl)phenyl.

In another embodiment A is —(CH$_2$)$_2$S(CH$_2$)$_3$— and B is (1-hydroxy-2-phenylethyl)phenyl.

In another embodiment A is —CH$_2$-Ph-OCH$_2$—, wherein Ph is interphenylene, and B is (1-hydroxy-2-phenylethyl)phenyl.

In another embodiment A is —CH$_2$-mPh-OCH$_2$—, wherein mPh is m-interphenylene, and B is (1-hydroxy-2-phenylethyl)phenyl.

In another embodiment A is —CH$_2$—O—(CH$_2$)$_4$— and B is (1-hydroxy-2-phenylethyl)phenyl.

In another embodiment A is —CH$_2$—O—CH$_2$—Ar—, wherein Ar is 2,5-interthienylene, and B is (1-hydroxy-2-phenylethyl)phenyl.

In another embodiment A is —CH$_2$—O—CH$_2$—Ar—, wherein Ar is 2,5-interfurylene, and B is (1-hydroxy-2-phenylethyl)phenyl.

Another embodiment comprises a compound selected from the group consisting of

5-[(R)-1-(4-tert-Butyl-phenyl)-5-oxo-pyrrolidin-2-yl-methoxy]-pentanoic acid;

3-[(R)-1-(4-tert-Butyl-phenyl)-5-oxo-pyrrolidin-2-yl-methoxymethyl]-benzoic acid;

5-[(R)-1-(4-tert-Butyl-phenyl)-5-oxo-pyrrolidin-2-yl-methoxymethyl]-furan-2-carboxylic acid;

5-[(R)-1-(4-tert-Butyl-phenyl)-5-oxo-pyrrolidin-2-yl-methoxymethyl]-thiophene-2-carboxylic acid;

7-[(S)-1-(4-tert-Butyl-phenyl)-5-oxo-pyrrolidin-2-yl]-heptanoic acid;

5-{(R)-1-[4-(1-Hydroxy-hexyl)-phenyl]-5-oxo-pyrrolidin-2-ylmethoxymethyl}-furan-2-carboxylic acid;

5-{(R)-1-[4-(1-Hydroxy-2-methyl-propyl)-phenyl]-5-oxo-pyrrolidin-2-ylmethoxymethyl}-furan-2-carboxylic acid;

5-{(R)-1-[4-(1-Hydroxy-2-phenyl-ethyl)-phenyl]-5-oxo-pyrrolidin-2-ylmethoxymethyl}-furan-2-carboxylic acid; and 5-{(R)-1-[4-(1-Hydroxy-hexyl)-phenyl]-5-oxo-pyrrolidin-2-ylmethoxymethyl}-thiophene-2-carboxylic acid.

The compounds of disclosed herein are useful for the prevention or treatment of glaucoma or ocular hypertension in mammals, or for the manufacture of a medicament for the treatment of glaucoma or ocular hypertension. They are also useful for the treatment of those diseases disclosed in the art as being amenable to treatment by prostaglandin $EP_2$ agonist, such as the ones listed previously.

A "pharmaceutically acceptable salt" is any salt that retains the activity of the parent compound and does not impart any additional deleterious or untoward effects on the subject to which it is administered and in the context in which it is administered compared to the parent compound. A pharmaceutically acceptable salt also refers to any salt which may form in vivo as a result of administration of an acid, another salt, or a prodrug which is converted into an acid or salt.

Pharmaceutically acceptable salts of acidic functional groups may be derived from organic or inorganic bases. The salt may comprise a mono or polyvalent ion. Of particular interest are the inorganic ions, lithium, sodium, potassium, calcium, and magnesium. Organic salts may be made with amines, particularly ammonium salts such as mono-, di- and trialkyl amines or ethanol amines. Salts may also be formed with caffeine, tromethamine and similar molecules. Hydrochloric acid or some other pharmaceutically acceptable acid may form a salt with a compound that includes a basic group, such as an amine or a pyridine ring.

A "prodrug" is a compound which is converted to a therapeutically active compound after administration, and the term should be interpreted as broadly herein as is generally understood in the art. While not intending to limit the scope of the invention, conversion may occur by hydrolysis of an ester group or some other biologically labile group. Generally, but not necessarily, a prodrug is inactive or less active than the therapeutically active compound to which it is converted. Ester prodrugs of the compounds disclosed herein are specifically contemplated. An ester may be derived from a carboxylic acid of C1 (i.e. the terminal carboxylic acid of a natural prostaglandin), or an ester may be derived from a carboxylic acid functional group on another part of the molecule, such as on a phenyl ring. While not intending to be limiting, an ester may be an alkyl ester, an aryl ester, or a heteroaryl ester. The term alkyl has the meaning generally understood by those skilled in the art and refers to linear, branched, or cyclic alkyl moieties. $C_{1-6}$ alkyl esters are particularly useful, where alkyl part of the ester has from 1 to 6 carbon atoms and includes, but is not limited to, methyl, ethyl, propyl, isopropyl, n-butyl, sec-butyl, iso-butyl, t-butyl, pentyl isomers, hexyl isomers, cyclopropyl, cyclobutyl, cyclopentyl, cyclohexyl, and combinations thereof having from 1-6 carbon atoms, etc.

A metabolite is broadly defined as a compound which is formed in vivo from the disclosed compound.

Those skilled in the art will readily understand that for administration or the manufacture of medicaments the compounds disclosed herein can be admixed with pharmaceutically acceptable excipients which per se are well known in the art. Specifically, a drug to be administered systemically, it may be confected as a powder, pill, tablet or the like, or as a solution, emulsion, suspension, aerosol, syrup or elixir suitable for oral or parenteral administration or inhalation.

For solid dosage forms or medicaments, non-toxic solid carriers include, but are not limited to, pharmaceutical grades of mannitol, lactose, starch, magnesium stearate, sodium saccharin, the polyalkylene glycols, talcum, cellulose, glucose, sucrose and magnesium carbonate. The solid dosage forms may be uncoated or they may be coated by known techniques to delay disintegration and absorption in the gastrointestinal tract and thereby provide a sustained action over a longer period. For example, a time delay material such as glyceryl monostearate or glyceryl distcarate may be employed. They may also be coated by the technique described in the U.S. Pat. Nos. 4,256,108; 4,166,452; and 4,265,874 to form osmotic therapeutic tablets for control release. Liquid pharmaceutically administrable dosage forms can, for example, comprise a solution or suspension of one or more of the presently useful compounds and optional pharmaceutical adjutants in a carrier, such as for example, water, saline, aqueous dextrose, glycerol, ethanol and the like, to thereby form a solution or suspension. If desired, the pharmaceutical composition to be administered may also contain minor amounts of nontoxic auxiliary substances such as wetting or emulsifying agents, pH buffering agents and the like. Typical examples of such auxiliary agents are sodium acetate, sorbitan monolaurate, triethanolamine, sodium acetate, triethanolamine oleate, etc. Actual methods of preparing such dosage forms are known, or will be apparent, to those skilled in this art; for example, see Remington's Pharmaceutical Sciences, Mack Publishing Company, Easton, Pa., 16th Edition, 1980. The composition of the formulation to be administered, in any event, contains a quantity of one or more of the presently useful compounds in an amount effective to provide the desired therapeutic effect.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol and the like. In addition, if desired, the injectable pharmaceutical compositions to be administered may also contain minor amounts of non-toxic auxiliary substances such as wetting or emulsifying agents, pH buffering agents and the like.

The amount of the presently useful compound or compounds administered is, of course, dependent on the therapeutic effect or effects desired, on the specific mammal being treated, on the severity and nature of the mammal's condition, on the manner of administration, on the potency and pharmacodynamics of the particular compound or compounds employed, and on the judgment of the prescribing physician. The therapeutically effective dosage of the presently useful compound or compounds is preferably in the range of about 0.5 or about 1 to about 100 mg/kg/day.

A liquid which is ophthalmically acceptable is formulated such that it can be administered topically to the eye. The comfort should be maximized as much as possible, although sometimes formulation considerations (e.g. drug stability) may necessitate less than optimal comfort. In the case that comfort cannot be maximized, the liquid should be formulated such that the liquid is tolerable to the patient for topical ophthalmic use. Additionally, an ophthalmically acceptable liquid should either be packaged for single use, or contain a preservative to prevent contamination over multiple uses.

For ophthalmic application, solutions or medicaments are often prepared using a physiological saline solution as a major vehicle. Ophthalmic solutions should preferably be maintained at a comfortable pH with an appropriate buffer system. The formulations may also contain conventional, pharmaceutically acceptable preservatives, stabilizers and surfactants.

Preservatives that may be used in the pharmaceutical compositions of the present invention include, but are not limited to, benzalkonium chloride, chlorobutanol, thimerosal, phenylmercuric acetate and phenylmercuric nitrate. A useful surfactant is, for example, Tween 80. Likewise, various useful vehicles may be used in the ophthalmic preparations of the present invention. These vehicles include, but are not limited to, polyvinyl alcohol, povidone, hydroxypropyl methyl cellulose, poloxamers, carboxymethyl cellulose, hydroxyethyl cellulose and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. Accordingly, buffers include acetate buffers, citrate buffers, phosphate buffers and borate buffers. Acids or bases may be used to adjust the pH of these formulations as needed.

In a similar vein, an ophthalmically acceptable antioxidant for use in the present invention includes, but is not limited to, sodium metabisulfite, sodium thiossulfate, acetylcysteine, butylated hydroxyanisole and butylated hydroxytoluene.

Other excipient components which may be included in the ophthalmic preparations are chelating agents. A useful chelating agent is edetate disodium, although other chelating agents may also be used in place or in conjunction with it.

The ingredients are usually used in the following amounts:

| Ingredient | Amount (% w/v) |
| --- | --- |
| active ingredient | about 0.001-5 |
| preservative | 0-0.10 |
| vehicle | 0-40 |
| tonicity adjustor | 0-10 |
| buffer | 0.01-10 |
| pH adjustor | q.s. pH 4.5-7.5 |
| antioxidant | as needed |
| surfactant | as needed |
| purified water | as needed to make 100% |

For topical use, creams, ointments, gels, solutions or suspensions, etc., containing the compound disclosed herein are employed. Topical formulations may generally be comprised of a pharmaceutical carrier, cosolvent, emulsifier, penetration enhancer, preservative system, and emollient.

The actual dose of the active compounds of the present invention depends on the specific compound, and on the condition to be treated; the selection of the appropriate dose is well within the knowledge of the skilled artisan.

The compounds disclosed herein are also useful in combination with other drugs useful for the treatment of glaucoma or other conditions.

For the treatment of glaucoma, combination treatment with the following classes of drugs are contemplated:

β-Blockers (or β-adrenergic antagonists) including carteolol, levobunolol, metiparanolol, timolol hemihydrate, timolol maleate, β1-selective antagonists such as betaxolol, and the like, or pharmaceutically acceptable salts or prodrugs thereof;

Adrenergic Agonists including non-selective adrenergic agonists such as epinephrine borate, epinephrine hydrochloride, and dipivefrin, and the like, or pharmaceutically acceptable salts or prodrugs thereof; and $\alpha_2$-selective adrenergic agonists such as apraclonidine, brimonidine, and the like, or pharmaceutically acceptable salts or prodrugs thereof;

Carbonic Anhydrase Inhibitors including acetazolamide, dichlorphenamide, methazolamide, brinzolamide, dorzolamide, and the like, or pharmaceutically acceptable salts or prodrugs thereof;

Cholinergic Agonists including direct acting cholinergic agonists such as carbachol, pilocarpine hydrochloride, pilocarbine nitrate, pilocarpine, and the like, or pharmaceutically acceptable salts or prodrugs thereof;

chlolinesterase inhibitors such as demecarium, echothiophate, physostigmine, and the like, or pharmaceutically acceptable salts or prodrugs thereof;

Glutamate Antagonists and other neuroprotective agents such as $Ca^{2+}$ channel blockers such as memantine, amantadine, rimantadine, nitroglycerin, dextrophan, detromethorphan, CGS-19755, dihydropyridines, verapamil, emopamil, benzothiazepines, bepridil, diphenylbutylpiperidines, diphenylpiperazines, HOE 166 and related drugs, fluspirilene, eliprodil, ifenprodil, CP-101,606, tibalosine, 2309BT, and 840S, flunarizine, nicardipine, nifedimpine, nimodipine, barnidipine, verapamil, lidoflazine, prenylamine lactate, amiloride, and the like, or pharmaceutically acceptable salts or prodrugs thereof;

Prostamides such as bimatoprost, or pharmaceutically acceptable salts or prodrugs thereof; and Prostaglandins including travoprost, UFO-21, chloprostenol, fluprostenol, 13,14-dihydro-chloprostenol, isopropyl unoprostone, latanoprost and the like.

Cannabinoids including CB1 agonists such as WIN-55212-2 and CP-55940 and the like, or pharmaceutically acceptable salts or prodrugs thereof.

For treatment of diseases affecting the eye including glaucoma, these compounds can be administered topically, periocularly, intraocularly, or by any other effective means known in the art.

Treatment of inflammatory bowel disease may be accomplished by the administration of the compounds described herein to the suffering mammal. Inflammatory bowel disease describes a variety of diseases characterized by inflammation of the bowels including, but not limited to, ulcerative colitis and Crohn's disease. Treatment may be accomplished by oral administration, by suppository, or parenteral administration, or some other suitable method.

While not intending to limit the scope of the invention in any way, delivery of the compounds disclosed herein to the colon via oral dosage forms may be accomplished by any of a number of methods known in the art. For example, reviews by Chourasia and Jain in J Pharm Pharmaceut Sci 6 (1): 33-66, 2003 and Shareef et. al (AAPS PharmSci 2003; 5 (2) Article 17) describe a number of useful methods. While not intending to limit the scope of the invention in any way these methods include 1) administration of a prodrug, including an azo or a carbohydrate based prodrug; 2) coating the drug with, or encapsulating or impregnating the drug into a polymer designed for delivery to the colon, 3) time released delivery of the drug, 4) use of a bioadhesive system; and the like.

While not intending to be bound in any way by theory, it is believed that intestinal microflora are capable of reductive cleavage of an azo bond leaving the two nitrogen atoms as amine functional groups. While not intending to limit the scope of the invention in any way, the azo prodrug approach has been used to deliver to 5-aminosalicylic acid to the colons of humans in clinical trials for the treatment of inflammatory bowel disease. It is also believed that bacteria of the lower GI also have enzymes which can digest glycosides, glucuronides, cyclodextrins, dextrans, and other carbohydrates, and ester prodrugs formed from these carbohydrates have been shown to deliver the parent active drugs selectively to the colon. For example, in vivo and in vitro studies on rats and guinea pigs with prodrugs of dexamethasone, prednisolone, hydrocortisone, and fludrocortisone, suggest that glycoside conjugates may be useful for the delivery of steroids to the human colon. Other in vivo studies have suggested that glucouronide, cyclodextrin, and dextran prodrugs of steroids or non-steroidal anti-inflammatory drugs are useful for delivery of these drugs to the lower GI tract. An amide of salicylic acid and glutamic acid has been shown to be useful for the delivery of salicylic acid to the colon of rabbit and dog.

While not intending to limit the scope of the invention in any way, carbohydrate polymers such as amylase, arabinogalactan, chitosan, chondroiton sulfate, dextran, guar gum, pectin, xylin, and the like, or azo-group containing polymers can be used to coat a drug compound, or a drug may be impregnated or encapsulated in the polymer. It is believed that after oral administration, the polymers remain stable in the upper GI tract, but are digested by the microflora of the lower GI thus releasing the drug for treatment.

Polymers which are sensitive to pH may also be used since the colon has a higher pH than the upper GI tract. Such polymers are commercially available. For example, Rohm Pharmaceuticals, Darmstadt, Germany, markets pH dependent methacrylate based polymers and copolymers which have varying solubilities over different pH ranges based upon the number of free carboxylate groups in the polymer under the tradename Eudragit®. Several Eudragit® dosage forms are currently used to deliver salsalazine for the treatment of ulcerative colitis and Crohn's disease. Time release systems, bioadhesive systems, and other delivery systems have also been studied.

One embodiment is use of a compound in the manufacture of a medicament for the treatment of inflammatory bowel disease, said compound comprising

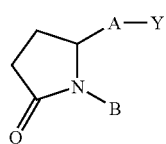

or a pharmaceutically acceptable salt, prodrug, or a metabolite thereof;
wherein
Y is an organic acid functional group, or an amide or ester thereof comprising up to 12 carbon atoms; or Y is hydroxymethyl or an ether thereof comprising up to 12 carbon atoms; or Y is a tetrazolyl functional group;
A is $-(CH_2)_6-$, cis $-CH_2CH=CH-(CH_2)_3-$, or $-CH_2C\equiv C-(CH_2)_3-$, wherein 1 or 2 carbon atoms may be substituted with S or O; or A is $-(CH_2)_m-Ar-(CH_2)_o-$ wherein Ar is interarylene or heterointerarylene, the sum of m and o is from 1 to 4, and wherein one $CH_2$ may be substituted with S or O; and
B is aryl or heteroaryl.

Another embodiment is use of a compound in the manufacture of a medicament for the treatment of inflammatory bowel disease, said compound comprising

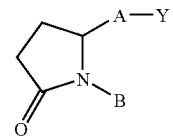

or a pharmaceutically acceptable salt, prodrug, or a metabolite thereof;
wherein
Y is an organic acid functional group, or an amide or ester thereof comprising up to 12 carbon atoms; or Y is hydroxymethyl or an ether thereof comprising up to 12 carbon atoms; or Y is a tetrazolyl functional group;
A is $-(CH_2)_6-$, cis $-CH_2CH=CH-(CH_2)_3-$, or $-CH_2C\equiv C-(CH_2)_3-$, wherein 1 or 2 carbon atoms may be substituted with S or O; or A is $-(CH_2)_m-Ar-(CH_2)_o-$ wherein Ar is interarylene or heterointerarylene, the sum of m and o is from 1 to 4, and wherein one $CH_2$ may be substituted with S or O; and
B is phenyl.

Another embodiment is use of a compound in the manufacture of a medicament for the treatment of inflammatory bowel disease, said compound comprising

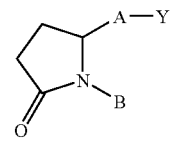

or a pharmaceutically acceptable salt, prodrug, or a metabolite thereof;
wherein
Y is an organic acid functional group, or an amide or ester thereof comprising up to 12 carbon atoms; or Y is hydroxymethyl or an ether thereof comprising up to 12 carbon atoms; or Y is a tetrazolyl functional group;
A is $-(CH_2)_6-$, cis $-CH_2CH=CH-(CH_2)_3-$, or $-CH_2C\equiv C-(CH_2)_3-$, wherein 1 or 2 carbon atoms may be substituted with S or O; or A is $-(CH_2)_m-Ar-(CH_2)_o-$ wherein Ar is interarylene or heterointerarylene, the sum of m and o is from 1 to 4, and wherein one $CH_2$ may be substituted with S or O; and
B is alkylphenyl.

Another embodiment is use of a compound in the manufacture of a medicament for the treatment of inflammatory bowel disease, said compound comprising

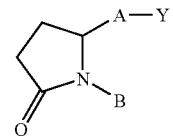

or a pharmaceutically acceptable salt, prodrug, or a metabolite thereof;
wherein
Y is an organic acid functional group, or an amide or ester thereof comprising up to 12 carbon atoms; or Y is hydroxymethyl or an ether thereof comprising up to 12 carbon atoms; or Y is a tetrazolyl functional group;
A is —(CH$_2$)$_6$—, cis —CH$_2$CH=CH—(CH$_2$)$_3$—, or —CH$_2$C≡C—(CH$_2$)$_3$—, wherein 1 or 2 carbon atoms may be substituted with S or O; or A is —(CH$_2$)$_m$—Ar—(CH$_2$)$_o$— wherein Ar is interarylene or heterointerarylene, the sum of m and o is from 1 to 4, and wherein one CH$_2$ may be substituted with S or O; and
B is p-t-butylphenyl.

Another embodiment is use of a compound in the manufacture of a medicament for the treatment of inflammatory bowel disease, said compound of claim selected from the group consisting of
5-[(R)-1-(4-tert-Butyl-phenyl)-5-oxo-pyrrolidin-2-yl-methoxy]-pentanoic acid;
3-[(R)-1-(4-tert-Butyl-phenyl)-5-oxo-pyrrolidin-2-yl-methoxymethyl]-benzoic acid;
5-[(R)-1-(4-tert-Butyl-phenyl)-5-oxo-pyrrolidin-2-yl-methoxymethyl]-furan-2-carboxylic acid;
5-[(R)-1-(4-tert-Butyl-phenyl)-5-oxo-pyrrolidin-2-yl-methoxymethyl]-thiophene-2-carboxylic acid;
7-[(S)-1-(4-tert-Butyl-phenyl)-5-oxo-pyrrolidin-2-yl]-heptanoic acid;
5-{(R)-1-[4-(1-Hydroxy-hexyl)-phenyl]-5-oxo-pyrrolidin-2-ylmethoxymethyl}-furan-2-carboxylic acid;
5-{(R)-1-[4-(1-Hydroxy-2-methyl-propyl)-phenyl]-5-oxo-pyrrolidin-2-ylmethoxymethyl}-furan-2-carboxylic acid;
5-{(R)-1-[4-(1-Hydroxy-2-phenyl-ethyl)-phenyl]-5-oxo-pyrrolidin-2-ylmethoxymethyl}-furan-2-carboxylic acid;
5-{(R)-1-[4-(1-Hydroxy-hexyl)-phenyl]-5-oxo-pyrrolidin-2-ylmethoxymethyl}-thiophene-2-carboxylic acid;
5-{(R)-1-[4-(1-Hydroxy-hexyl)-phenyl]-5-oxo-pyrrolidin-2-ylmethoxymethyl}-thiophene-2-carboxylic acid isopropyl ester;
3-{(R)-1-[4-(1-Hydroxy-hexyl)-phenyl]-5-oxo-pyrrolidin-2-ylmethoxymethyl}-benzoic acid;
5-{(R)-1-[4-(1-Hydroxy-pentyl)-phenyl]-5-oxo-pyrrolidin-2-ylmethoxymethyl}-thiophene-2-carboxylic acid;
5-{(R)-1-[4-(1-Hydroxy-heptyl)-phenyl]-5-oxo-pyrrolidin-2-ylmethoxymethyl}-thiophene-2-carboxylic acid;
5-{(R)-1-[4-(1-Hydroxy-butyl)-phenyl]-5-oxo-pyrrolidin-2-ylmethoxymethyl}-thiophene-2-carboxylic acid;
5-{(R)-1-[4-(1-Hydroxy-propyl)-phenyl]-5-oxo-pyrrolidin-2-ylmethoxymethyl}-thiophene-2-carboxylic acid;
5-((E and Z)-3-{(R)-1-[4-(1-Hydroxy-hexyl)-phenyl]-5-oxo-pyrrolidin-2-yl}-allyl)-thiophene-2-carboxylic acid;
5-(3-{(S)-1-[4-(1-Hydroxy-hexyl)-phenyl]-5-oxo-pyrrolidin-2-yl}-propyl)-thiophene-2-carboxylic acid;
5-(3-{(S)-1-[4-(1-Hydroxy-hexyl)-phenyl]-5-oxo-pyrrolidin-2-yl}-propyl)-thiophene-2-carboxylic acid isopropyl ester (mixture of diastereomers);
5-{3-[(S)-1-(4-Hexanoyl-phenyl)-5-oxo-pyrrolidin-2-yl]-propyl}-thiophene-2-carboxylic acid;
5-[(R)-1-(4-Hexanoyl-phenyl)-5-oxo-pyrrolidin-2-yl-methoxymethyl]-thiophene-2-carboxylic acid;
5-{(R)-1-[4-(1-Hydroxy-hexyl)-phenyl]-5-oxo-pyrrolidin-2-ylmethoxymethyl}-thiophene-2-carboxylic acid isopropyl ester (faster eluting diastereomer);
5-{(R)-1-[4-(1-Hydroxy-hexyl)-phenyl]-5-oxo-pyrrolidin-2-ylmethoxymethyl}-thiophene-2-carboxylic acid isopropyl ester (slower eluting diastereomer);
5-{(R)-1-[4-(1-Hydroxy-hexyl)-phenyl]-5-oxo-pyrrolidin-2-ylmethoxymethyl}-thiophene-2-carboxylic acid (from faster eluting diastereomer);
5-{(R)-1-[4-(1-Hydroxy-hexyl)-phenyl]-5-oxo-pyrrolidin-2-ylmethoxymethyl}-thiophene-2-carboxylic acid (from slower eluting diastereomer);
5-(3-{(S)-1-[4-(1-Hydroxy-hexyl)-phenyl]-5-oxo-pyrrolidin-2-yl}-propyl)-thiophene-2-carboxylic acid methyl ester (faster eluting diastereomer);
5-(3-{(S)-1-[4-(1-hydroxy-hexyl)-phenyl]-5-oxo-pyrrolidin-2-yl}-propyl)-thiophene-2-carboxylic acid methyl ester (slower eluting diastereomer);
5-(3-{(S)-1-[4-(1-Hydroxy-hexyl)-phenyl]-5-oxo-pyrrolidin-2-yl}-propyl)-thiophene-2-carboxylic acid (from faster eluting diastereomer);
5-(3-{(S)-1-[4-(1-Hydroxy-hexyl)-phenyl]-5-oxo-pyrrolidin-2-yl}-propyl)-thiophene-2-carboxylic acid (from slower eluting diastereomer);
5-(3-{(S)-1-[4-(1-Hydroxy-hexyl)-phenyl]-5-oxo-pyrrolidin-2-yl}-propyl)-thiophene-2-carboxylic acid isopropyl ester (from faster eluting diastereomer);
5-(3-{(S)-1-[4-(1-Hydroxy-hexyl)-phenyl]-5-oxo-pyrrolidin-2-yl}-propyl)-thiophene-2-carboxylic acid isopropyl ester (from slower eluting diastereomer);
5-{(R)-1-[4-(1-Hydroxy-heptyl)-phenyl]-5-oxo-pyrrolidin-2-ylmethoxymethyl}-thiophene-2-carboxylic acid isopropyl ester (mixture of diastereomers);
5-{(R)-1-[4-(1-Hydroxy-heptyl)-phenyl]-5-oxo-pyrrolidin-2-ylmethoxymethyl}-thiophene-2-carboxylic acid isopropyl ester (faster eluting diastereomer);
5-{(R)-1-[4-(1-hydroxy-heptyl)-phenyl]-5-oxo-pyrrolidin-2-ylmethoxymethyl}-thiophene-2-carboxylic acid isopropyl ester (slower eluting diastereomer);
5-{(R)-1-[4-(1-Hydroxy-heptyl)-phenyl]-5-oxo-pyrrolidin-2-ylmethoxymethyl}-thiophene-2-carboxylic acid (from faster eluting diastereomer);
5-{(R)-1-[4-(1-Hydroxy-heptyl)-phenyl]-5-oxo-pyrrolidin-2-ylmethoxymethyl}-thiophene-2-carboxylic acid (from slower eluting diastereomer);
5-(3-{(S)-1-[4-(1-Hydroxy-heptyl)-phenyl]-5-oxo-pyrrolidin-2-yl}-propyl)-thiophene-2-carboxylic acid;
5-(3-{(S)-1-[4-(1-Hydroxy-heptyl)-phenyl]-5-oxo-pyrrolidin-2-yl}-propyl)-thiophene-2-carboxylic acid methyl ester (faster eluting diastereomer);
5-(3-{(S)-1-[4-(1-hydroxy-heptyl)-phenyl]-5-oxo-pyrrolidin-2-yl}-propyl)-thiophene-2-carboxylic acid methyl ester (slower eluting diastereomer);
5-(3-{(S)-1-[4-(1-Hydroxy-heptyl)-phenyl]-5-oxo-pyrrolidin-2-yl}-propyl)-thiophene-2-carboxylic acid (from faster eluting diastereomer);
5-(3-{(S)-1-[4-(1-Hydroxy-heptyl)-phenyl]-5-oxo-pyrrolidin-2-yl}-propyl)-thiophene-2-carboxylic acid (from slower eluting diastereomer);
5-(3-{(S)-1-[4-(1-Hydroxy-heptyl)-phenyl]-5-oxo-pyrrolidin-2-yl}-propyl)-thiophene-2-carboxylic acid isopropyl ester (from faster eluting diastereomer);
5-(3-{(S)-1-[4-(1-Hydroxy-heptyl)-phenyl]-5-oxo-pyrrolidin-2-yl}-propyl)-thiophene-2-carboxylic acid isopropyl ester (from slower eluting diastereomer); and
4-{(R)-1-[4-(1-Hydroxy-hexyl)-phenyl]-5-oxo-pyrrolidin-2-ylmethoxy}-benzoic acid.

Another embodiment is use of a compound in the manufacture of a medicament for the treatment of inflammatory bowel disease, said compound of comprising

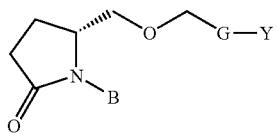

or a pharmaceutically acceptable salt, prodrug, or a metabolite thereof;

wherein

Y is an organic acid functional group, or an amide or ester thereof comprising up to 12 carbon atoms; or Y is hydroxymethyl or an ether thereof comprising up to 12 carbon atoms; or Y is a tetrazolyl functional group;

G is 1,3-interaryl or interheteroaryl, or —(CH$_2$)$_3$—; and

B is aryl or heteroaryl.

Another embodiment is use of a compound in the manufacture of a medicament for the treatment of inflammatory bowel disease, said compound of comprising

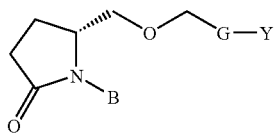

or a pharmaceutically acceptable salt, prodrug, or a metabolite thereof;

wherein

Y is an organic acid functional group, or an amide or ester thereof comprising up to 12 carbon atoms; or Y is hydroxymethyl or an ether thereof comprising up to 12 carbon atoms; or Y is a tetrazolyl functional group;

G is 1,3-interaryl or interheteroaryl, or —(CH$_2$)$_3$—; and

B is phenyl.

Another embodiment is use of a compound in the manufacture of a medicament for the treatment of inflammatory bowel disease, said compound of comprising

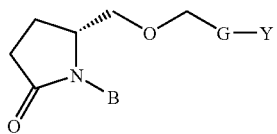

or a pharmaceutically acceptable salt, prodrug, or a metabolite thereof;

wherein

Y is an organic acid functional group, or an amide or ester thereof comprising up to 12 carbon atoms; or Y is hydroxymethyl or an ether thereof comprising up to 12 carbon atoms; or Y is a tetrazolyl functional group;

G is 1,3-interaryl or interheteroaryl, or —(CH$_2$)$_3$—; and

B is hydroxyalkylphenyl.

Another embodiment is use of a compound in the manufacture of a medicament for the treatment of inflammatory bowel disease, said compound comprising

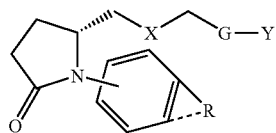

or a pharmaceutically acceptable salt, prodrug, or a metabolite thereof;

wherein a dashed line indicates the presence or absence of a bond;

Y is an organic acid functional group, or an amide or ester thereof comprising up to 12 carbon atoms; or Y is hydroxymethyl or an ether thereof comprising up to 12 carbon atoms; or Y is a tetrazolyl functional group;

R is hydrocarbyl or hydroxyhydrocarbyl having from 1 to 12 carbon atoms;

X is CH$_2$, O, or S; and

G is 1,3-interaryl or interheteroaryl, or —(CH$_2$)$_3$—.

Another embodiment is use of a compound in the manufacture of a medicament for the treatment of inflammatory bowel disease, said compound comprising an N-aryl or N-heteroaryl gamma lactam which is effective at reducing intraocular pressure in a mammal.

One embodiment is a compound comprising

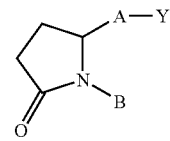

or a pharmaceutically acceptable salt, prodrug, or a metabolite thereof;

wherein

Y is an organic acid functional group, or an amide or ester thereof comprising up to 12 carbon atoms; or Y is hydroxymethyl or an ether thereof comprising up to 12 carbon atoms; or Y is a tetrazolyl functional group;

A is —(CH$_2$)$_6$—, cis —CH$_2$CH═CH—(CH$_2$)$_3$—, or —CH$_2$C≡C—(CH$_2$)$_3$—, wherein 1 or 2 carbon atoms may be substituted with S or O; or A is —(CH$_2$)$_m$—Ar—(CH$_2$)$_o$— wherein Ar is interarylene or heterointerarylene, the sum of m and o is from 1 to 4, and wherein one CH$_2$ may be substituted with S or O; and B is aryl or heteroaryl.

Another embodiment is a compound comprising

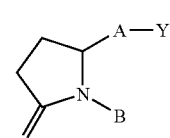

or a pharmaceutically acceptable salt, prodrug, or a metabolite thereof;

wherein

Y is an organic acid functional group, or an amide or ester thereof comprising up to 12 carbon atoms; or Y is hydroxymethyl or an ether thereof comprising up to 12 carbon atoms; or Y is a tetrazolyl functional group;

A is —(CH$_2$)$_6$—, cis —CH$_2$CH═CH—(CH$_2$)$_3$—, or —CH$_2$C≡C—(CH$_2$)$_3$—, wherein 1 or 2 carbon atoms may be substituted with S or O; or A is —(CH$_2$)$_m$—Ar—(CH$_2$)$_o$— wherein Ar is interarylene or heterointerarylene, the sum of m and o is from 1 to 4, and wherein one CH$_2$ may be substituted with S or O; and B is phenyl.

Another embodiment is a compound comprising

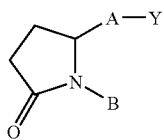

or a pharmaceutically acceptable salt, prodrug, or a metabolite thereof;
wherein
Y is an organic acid functional group, or an amide or ester thereof comprising up to 12 carbon atoms; or Y is hydroxymethyl or an ether thereof comprising up to 12 carbon atoms; or Y is a tetrazolyl functional group;
A is —(CH$_2$)$_6$—, cis —CH$_2$CH═CH—(CH$_2$)$_3$—, or —CH$_2$C≡C—(CH$_2$)$_3$—, wherein 1 or 2 carbon atoms may be substituted with S or O; or A is —(CH$_2$)$_m$—Ar—(CH$_2$)$_o$— wherein Ar is interarylene or heterointerarylene, the sum of m and o is from 1 to 4, and wherein one CH$_2$ may be substituted with S or O; and B is alkylphenyl.

Another embodiment is a compound comprising

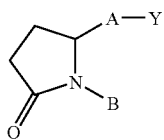

or a pharmaceutically acceptable salt, prodrug, or a metabolite thereof; wherein
Y is an organic acid functional group, or an amide or ester thereof comprising up to 12 carbon atoms; or Y is hydroxymethyl or an ether thereof comprising up to 12 carbon atoms; or Y is a tetrazolyl functional group;
A is —(CH$_2$)$_6$—, cis —CH$_2$CH═CH—(CH$_2$)$_3$—, or —CH$_2$C≡C—(CH$_2$)$_3$—, wherein 1 or 2 carbon atoms may be substituted with S or O; or A is —(CH$_2$)$_m$—Ar—(CH$_2$)$_o$— wherein Ar is interarylene or heterointerarylene, the sum of m and o is from 1 to 4, and wherein one CH$_2$ may be substituted with S or O; and B is p-t-butylphenyl.

Another embodiment is a compound of claim selected from the group consisting of

5-[(R)-1-(4-tert-Butyl-phenyl)-5-oxo-pyrrolidin-2-ylmethoxy]-pentanoic acid;

3-[(R)-1-(4-tert-Butyl-phenyl)-5-oxo-pyrrolidin-2-ylmethoxymethyl]-benzoic acid;

5-[(R)-1-(4-tert-Butyl-phenyl)-5-oxo-pyrrolidin-2-ylmethoxymethyl]-furan-2-carboxylic acid;

5-[(R)-1-(4-tert-Butyl-phenyl)-5-oxo-pyrrolidin-2-ylmethoxymethyl]-thiophene-2-carboxylic acid;

7-[(S)-1-(4-tert-Butyl-phenyl)-5-oxo-pyrrolidin-2-yl]-heptanoic acid;

5-{(R)-1-[4-(1-Hydroxy-hexyl)-phenyl]-5-oxo-pyrrolidin-2-ylmethoxymethyl}-furan-2-carboxylic acid;

5-{(R)-1-[4-(1-Hydroxy-2-methyl-propyl)-phenyl]-5-oxo-pyrrolidin-2-ylmethoxymethyl}-furan-2-carboxylic acid;

5-{(R)-1-[4-(1-Hydroxy-2-phenyl-ethyl)-phenyl]-5-oxo-pyrrolidin-2-ylmethoxymethyl}-furan-2-carboxylic acid;

5-{(R)-1-[4-(1-Hydroxy-hexyl)-phenyl]-5-oxo-pyrrolidin-2-ylmethoxymethyl}-thiophene-2-carboxylic acid;

5-{(R)-1-[4-(1-Hydroxy-hexyl)-phenyl]-5-oxo-pyrrolidin-2-ylmethoxymethyl}-thiophene-2-carboxylic acid isopropyl ester;

3-{(R)-1-[4-(1-Hydroxy-hexyl)-phenyl]-5-oxo-pyrrolidin-2-ylmethoxymethyl}-benzoic acid;

5-{(R)-1-[4-(1-Hydroxy-pentyl)-phenyl]-5-oxo-pyrrolidin-2-ylmethoxymethyl}-thiophene-2-carboxylic acid;

5-{(R)-1-[4-(1-Hydroxy-heptyl)-phenyl]-5-oxo-pyrrolidin-2-ylmethoxymethyl}-thiophene-2-carboxylic acid;

5-{(R)-1-[4-(1-Hydroxy-butyl)-phenyl]-5-oxo-pyrrolidin-2-ylmethoxymethyl}-thiophene-2-carboxylic acid;

5-{(R)-1-[4-(1-Hydroxy-propyl)-phenyl]-5-oxo-pyrrolidin-2-ylmethoxymethyl}-thiophene-2-carboxylic acid;

5-((E and Z)-3-{(R)-1-[4-(1-Hydroxy-hexyl)-phenyl]-5-oxo-pyrrolidin-2-yl}-allyl)-thiophene-2-carboxylic acid;

5-(3-{(S)-1-[4-(1-Hydroxy-hexyl)-phenyl]-5-oxo-pyrrolidin-2-yl}-propyl)-thiophene-2-carboxylic acid;

5-(3-{(S)-1-[4-(1-Hydroxy-hexyl)-phenyl]-5-oxo-pyrrolidin-2-yl}-propyl)-thiophene-2-carboxylic acid isopropyl ester (mixture of diastereomers);

5-{3-[(S)-1-(4-Hexanoyl-phenyl)-5-oxo-pyrrolidin-2-yl]-propyl}-thiophene-2-carboxylic acid;

5-[(R)-1-(4-Hexanoyl-phenyl)-5-oxo-pyrrolidin-2-ylmethoxymethyl]-thiophene-2-carboxylic acid;

5-{(R)-1-[4-(1-Hydroxy-hexyl)-phenyl]-5-oxo-pyrrolidin-2-ylmethoxymethyl}-thiophene-2-carboxylic acid isopropyl ester (faster eluting diastereomer);

5-{(R)-1-[4-(1-Hydroxy-hexyl)-phenyl]-5-oxo-pyrrolidin-2-ylmethoxymethyl}-thiophene-2-carboxylic acid isopropyl ester (slower eluting diastereomer);

5-{(R)-1-[4-(1-Hydroxy-hexyl)-phenyl]-5-oxo-pyrrolidin-2-ylmethoxymethyl}-thiophene-2-carboxylic acid (from faster eluting diastereomer);

5-{(R)-1-[4-(1-Hydroxy-hexyl)-phenyl]-5-oxo-pyrrolidin-2-ylmethoxymethyl}-thiophene-2-carboxylic acid (from slower eluting diastereomer);

5-(3-{(S)-1-[4-(1-Hydroxy-hexyl)-phenyl]-5-oxo-pyrrolidin-2-yl}-propyl)-thiophene-2-carboxylic acid methyl ester (faster eluting diastereomer);

5-(3-{(S)-1-[4-(1-hydroxy-hexyl)-phenyl]-5-oxo-pyrrolidin-2-yl}-propyl)-thiophene-2-carboxylic acid methyl ester (slower eluting diastereomer);

5-(3-{(S)-1-[4-(1-Hydroxy-hexyl)-phenyl]-5-oxo-pyrrolidin-2-yl}-propyl)-thiophene-2-carboxylic acid (from faster eluting diastereomer);

5-(3-{(S)-1-[4-(1-Hydroxy-hexyl)-phenyl]-5-oxo-pyrrolidin-2-yl}-propyl)-thiophene-2-carboxylic acid (from slower eluting diastereomer);

5-(3-{(S)-1-[4-(1-Hydroxy-hexyl)-phenyl]-5-oxo-pyrrolidin-2-yl}-propyl)-thiophene-2-carboxylic acid isopropyl ester (from faster eluting diastereomer);

5-(3-{(S)-1-[4-(1-Hydroxy-hexyl)-phenyl]-5-oxo-pyrrolidin-2-yl}-propyl)-thiophene-2-carboxylic acid isopropyl ester (from slower eluting diastereomer);

5-{(R)-1-[4-(1-Hydroxy-heptyl)-phenyl]-5-oxo-pyrrolidin-2-ylmethoxymethyl}-thiophene-2-carboxylic acid isopropyl ester (mixture of diastereomers);

5-{(R)-1-[4-(1-Hydroxy-heptyl)-phenyl]-5-oxo-pyrrolidin-2-ylmethoxymethyl}-thiophene-2-carboxylic acid isopropyl ester (faster eluting diastereomer);

5-{(R)-1-[4-(1-hydroxy-heptyl)-phenyl]-5-oxo-pyrrolidin-2-ylmethoxymethyl}-thiophene-2-carboxylic acid isopropyl ester (slower eluting diastereomer);

5-{(R)-1-[4-(1-Hydroxy-heptyl)-phenyl]-5-oxo-pyrrolidin-2-ylmethoxymethyl}-thiophene-2-carboxylic acid (from faster eluting diastereomer);

5-{(R)-1-[4-(1-Hydroxy-heptyl)-phenyl]-5-oxo-pyrrolidin-2-ylmethoxymethyl}-thiophene-2-carboxylic acid (from slower eluting diastereomer);

5-(3-{(S)-1-[4-(1-Hydroxy-heptyl)-phenyl]-5-oxo-pyrrolidin-2-yl}-propyl)-thiophene-2-carboxylic acid;

5-(3-{(S)-1-[4-(1-Hydroxy-heptyl)-phenyl]-5-oxo-pyrrolidin-2-yl}-propyl)-thiophene-2-carboxylic acid methyl ester (faster eluting diastereomer);

5-(3-{(S)-1-[4-(1-hydroxy-heptyl)-phenyl]-5-oxo-pyrrolidin-2-yl}-propyl)-thiophene-2-carboxylic acid methyl ester (slower eluting diastereomer);

5-(3-{(S)-1-[4-(1-Hydroxy-heptyl)-phenyl]-5-oxo-pyrrolidin-2-yl}-propyl)-thiophene-2-carboxylic acid (from faster eluting diastereomer);

5-(3-{(S)-1-[4-(1-Hydroxy-heptyl)-phenyl]-5-oxo-pyrrolidin-2-yl}-propyl)-thiophene-2-carboxylic acid (from slower eluting diastereomer);

5-(3-{(S)-1-[4-(1-Hydroxy-heptyl)-phenyl]-5-oxo-pyrrolidin-2-yl}-propyl)-thiophene-2-carboxylic acid isopropyl ester (from faster eluting diastereomer);

5-(3-{(S)-1-[4-(1-Hydroxy-heptyl)-phenyl]-5-oxo-pyrrolidin-2-yl}-propyl)-thiophene-2-carboxylic acid isopropyl ester (from slower eluting diastereomer); and 4-{(R)-1-[4-(1-Hydroxy-hexyl)-phenyl]-5-oxo-pyrrolidin-2-ylmethoxy}-benzoic acid. Another embodiment is a compound of comprising

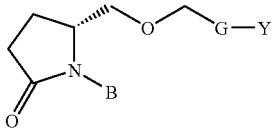

or a pharmaceutically acceptable salt, prodrug, or a metabolite thereof;
wherein
Y is an organic acid functional group, or an amide or ester thereof comprising up to 12 carbon atoms; or Y is hydroxymethyl or an ether thereof comprising up to 12 carbon atoms; or Y is a tetrazolyl functional group;
G is 1,3-interaryl or interheteroaryl, or —(CH$_2$)$_3$—; and
B is aryl or heteroaryl.

Another embodiment is a compound of comprising

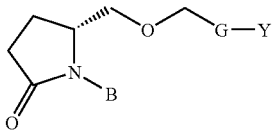

or a pharmaceutically acceptable salt, prodrug, or a metabolite thereof;
wherein
Y is an organic acid functional group, or an amide or ester thereof comprising up to 12 carbon atoms; or Y is hydroxymethyl or an ether thereof comprising up to 12 carbon atoms; or Y is a tetrazolyl functional group;
G is 1,3-interaryl or interheteroaryl, or —(CH$_2$)$_3$—; and
B is phenyl.

Another embodiment is a compound of comprising

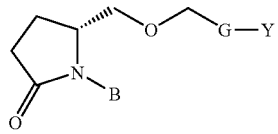

or a pharmaceutically acceptable salt, prodrug, or a metabolite thereof;
wherein
Y is an organic acid functional group, or an amide or ester thereof comprising up to 12 carbon atoms; or Y is hydroxymethyl or an ether thereof comprising up to 12 carbon atoms; or Y is a tetrazolyl functional group;
G is 1,3-interaryl or interheteroaryl, or —(CH$_2$)$_3$—; and
B is hydroxyalkylphenyl.

Another embodiment is a compound comprising

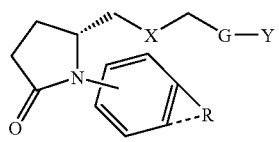

or a pharmaceutically acceptable salt, prodrug, or a metabolite thereof;
wherein a dashed line indicates the presence or absence of a bond;
Y is an organic acid functional group, or an amide or ester thereof comprising up to 12 carbon atoms; or Y is hydroxymethyl or an ether thereof comprising up to 12 carbon atoms; or Y is a tetrazolyl functional group;
R is hydrocarbyl or hydroxyhydrocarbyl having from 1 to 12 carbon atoms;
X is CH$_2$, O, or S; and
G is 1,3-interaryl or interheteroaryl, or —(CH$_2$)$_3$—.

Another embodiment is a compound comprising an N-aryl or N-heteroaryl gamma lactam which is effective at reducing intraocular pressure in a mammal.

Embodiments contemplated for each compound disclosed herein are use of the compound in the manufacture of a medicament for the treatment of glaucoma or ocular hypertension.

Embodiments contemplated for each compound disclosed herein are use of the compound in the manufacture of a medicament for the treatment of inflammatory bowel disease.

Embodiments contemplated for each compound disclosed herein are methods comprising administering an effective amount of the compound to a mammal for the treatment of glaucoma or ocular hypertension.

Embodiments contemplated for each compound disclosed herein are methods comprising administering an effective amount of the compound to a mammal for the treatment of inflammatory bowel disease.

Embodiments contemplated for each compound disclosed herein are compositions comprising the compound, wherein said compositions are ophthalmically acceptable liquids.

EXAMPLE 1

5-[(R)-1-(4-tert-Butyl-phenyl)-5-oxo-pyrrolidin-2-ylmethoxy]-pentanoic acid (4)

Step 1. Arylation of 1 to give 2

A solution of amide 1 (3.30 g, 14.4 mmol) in 1,4-dioxane (25 mL) was added to a mixture of 4,5-bis(triphenylphosphino)-9,9-dimethylxanthene (xantphos, 600 mg, 1.04 mmol), $Pd_2(dba)_3$ (317 mg, 0.35 mmol) and $Cs_2CO_3$ (6.46 g, 19.8 mmol). 1-Bromo-4-tert-butylbenzene (2.40 mL, 13.8 mmol) was added and the reaction mixture was purged with nitrogen. The mixture was heated at reflux for 19 h, then cooled to rt. The reaction mixture was then filtered through celite, washing with $CH_2Cl_2$, and the filtrate was concentrated in vacuo. Purification of the residue by flash column chromatography on silica gel (10%→20% EtOAc/Hexane, gradient) afforded 3.53 g (71%) of the desired product 2.

Step 2. Deprotection of 2 to give 3

HF-pyridine (5 mL) was added to a solution of silyl ether 2 (3.53 g, 9.76 mmol) in MeCN (20 mL) in a plastic bottle. The reaction was stirred at rt for 5 h, then was quenched with saturated aqueous $NaHCO_3$ (250 mL). The mixture was extracted with EtOAc (3×100 mL). The combined extracts were washed with brine (150 mL) then dried ($Na_2SO_4$), filtered and concentrated in vacuo to yield 2.14 g (89%) of the desired product 3.

Step 3. Alkylation of 3 to give the Ester of 4

Sodium hydride (11 mg, 0.46 mmol) was added to a solution of alcohol 3 (100 mg, 0.40 mmol) in THF (3 mL) at 0° C. under nitrogen. After 1 h at 0° C., methyl 5-bromovalerate (67 μL, 0.47 mmol) was added and the reaction was allowed to warm to rt. After 3 h, tlc analysis showed mostly starting alcohol remaining and another portion of bromide (67 μL, 0.47 mmol) was added. After 22 h total reaction time, the reaction was quenched with 1 N HCl and extracted with EtOAc (3×25 mL). Combined extracts were dried ($Na_2SO_4$), filtered and concentrated in vacuo. Purification of the residue by flash column chromatography on silica gel (40% EtOAc/Hexane→EtOAc, gradient) afforded 19 mg (13%) of the desired ester.

Step 4. Saponification to Give 4

Aqueous lithium hydroxide (1 N, 0.5 mL) was added to a solution of ester from step 3 above (12.3 mg, 0.034 mmol) in THF (0.7 mL). After 2.5 h at rt, the reaction was acidified with 0.25 M HCl (5 mL) then extracted with $CH_2Cl_2$ (3×7 mL). Combined extracts were dried ($Na_2SO_4$), filtered and concentrated in vacuo to afford 10.2 mg (86%) of the title compound (4).

EXAMPLE 2

3-[(R)-1-(4-tert-Butyl-phenyl)-5-oxo-pyrrolidin-2-ylmethoxymethyl]-benzoic acid (5)

Step 1. Alkylation of 3 to Give the Ester of 5

Potassium hydride (23.4 mg, 0.58 mmol) and 18-crown-6 (167 mg, 0.63 mmol) were added sequentially to a solution of alcohol 3 (130 mg, 0.53 mmol) in THF (3 mL) at 0° C. After 1 h at 0° C., a solution of methyl 3-(chloromethyl)benzoate (prepared from the corresponding acid chloride, pyridine and methanol: see *J. Org. Chem.* 1988, 53, 2548-2552; 116 mg, 0.63 mmol) in THF (1.5 mL) was added via cannula and the reaction was allowed to warm to rt. After 22.5 h, the reaction was quenched with 0.1 N HCl (10 mL) and extracted with EtOAc (3×15 mL). Combined extracts were washed with saturated aqueous $NaHCO_3$ (15 mL) and brine (15 mL) then dried ($Na_2SO_4$), filtered and concentrated in vacuo. Purification of the residue by flash column chromatography on silica gel (30%→50% EtOAc/Hexane, gradient) afforded 66 mg (32%) of the desired ester.

Step 2. Saponification to Give 5

Aqueous lithium hydroxide (1 N, 0.4 mL) was added to a solution of ester from step 1 above (33.5 mg, 0.085 mmol) in THF (0.75 mL). After 3.5 h at rt, the reaction was acidified with 0.25 M HCl (5 mL) then extracted with $CH_2Cl_2$ (3×10 mL). Combined extracts were dried ($Na_2SO_4$), filtered and concentrated in vacuo. Purification of the residue by flash column chromatography on silica gel (2% MeOH/$CH_2Cl_2$), followed by preparative thin layer chromatography (10% MeOH/$CH_2Cl_2$) afforded 6.6 mg (20%) of the title compound (5).

EXAMPLE 3

5-[(R)-1-(4-tert-Butyl-phenyl)-5-oxo-pyrrolidin-2-ylmethoxymethyl]-furan-2-carboxylic acid (6)

Step 1. Alkylation of 3 to Give the Ester of 6

Potassium hydride (27 mg, 0.67 mmol) and 18-crown-6 (193 mg, 0.73 mmol) were added sequentially to a solution of alcohol 3 (150 mg, 0.61 mmol) in THF (4 mL) at 0° C. After 1 h at 0° C., a solution of ethyl 5-chloromethylfuran-2-carboxylate (commercially available from Aldrich Chemical Company, 138 mg, 0.73 mmol) in THF (1 mL) was added via cannula and the reaction was allowed to warm to rt. After 18.5 h, the reaction was quenched with 0.25 N HCl (10 mL) and extracted with EtOAc (3×15 mL). Combined extracts were washed with brine (20 mL) then dried ($Na_2SO_4$), filtered and concentrated in vacuo. Purification of the residue by flash column chromatography on silica gel (20%→50% EtOAc/Hexane, gradient) afforded 78 mg (32%) of the desired ester.

Step 2. Saponification to Give 6

Aqueous lithium hydroxide (1 N, 0.5 mL) was added to a solution of ester from step 1 above (66.7 mg, 0.17 mmol) in THF (0.5 mL). After 3 h at rt, the reaction was acidified with 1 N HCl (2 mL) then extracted with $CH_2Cl_2$ (3×10 mL). Combined extracts were dried ($Na_2SO_4$), filtered and concentrated in vacuo to afford 54.4 mg (88%) of the title compound (6).

EXAMPLE 4

5-[(R)-1-(4-tert-Butyl-phenyl)-5-oxo-pyrrolidin-2-ylmethoxymethyl]-thiophene-2-carboxylic acid (7)

Step 1. Alkylation of 3 to Give the Ester of 7

Potassium hydride (25.2 mg, 0.63 mmol) and 18-crown-6 (181 mg, 0.68 mmol) were added sequentially to a solution of alcohol 3 (140 mg, 0.57 mmol) in THF (4 mL) at 0° C. After 1.5 h at 0° C., a solution of methyl 5-chloromethylthiophene-2-carboxylate (prepared according to the procedures described in WO2004/037808; 130 mg, 0.68 mmol) in THF (1.5 mL) was added via cannula and the reaction was allowed to warm to rt. After 20 h, the reaction was quenched with 0.25 N HCl (15 mL) and extracted with EtOAc (3×20 mL). Combined extracts were washed with brine (30 mL) then dried ($Na_2SO_4$), filtered and concentrated in vacuo. Purification of the residue by flash column chromatography on silica gel (20%→50% EtOAc/Hexane, gradient) afforded 40.7 mg (18%) of the desired ester.

Step 2. Saponification to Give 7

Aqueous lithium hydroxide (1 N, 0.4 mL) was added to a solution of ester from step 1 above (37 mg, 0.092 mmol) in THF (0.75 mL). After 18 h at rt, the reaction was acidified with 1 N HCl (7 mL) then extracted with $CH_2Cl_2$ (3×10 mL). Combined extracts were dried ($Na_2SO_4$), filtered and concentrated in vacuo to afford 22.3 mg (62%) of the title compound (7).

EXAMPLE 5

7-[(S)-1-(4-tert-Butyl-phenyl)-5-oxo-pyrrolidin-2-yl]-heptanoic acid (10)

Step 1. Oxidation of 3 to give Aldehyde 8

Molecular sieves (4 Å, 300 mg), 4-methylmorpholine N-oxide (427 mg, 3.64 mmol) and tetrapropylammonium perruthenate (250 mg, 0.71 mmol) were added sequentially to a solution of alcohol 3 (600 mg, 2.43 mmol) in $CH_2Cl_2$ (15 mL) at rt. After 23 h, the reaction mixture was filtered through celite, washing with $CH_2Cl_2$ (10 mL). The filtrate was concentrated in vacuo. Purification of the residue by flash column chromatography on silica gel ($CH_2Cl_2 \rightarrow 10\%$ EtOAc/$CH_2Cl_2$, gradient) afforded 92 mg (15%) of the desired aldehyde 8.

Step 2. Wittig Reaction of 8 to Give 9

Potassium bis(trimethylsilyl)amide (0.5 M in PhMe, 1.92 mL, 0.96 mmol) was added to a solution of aldehyde 8 (86 mg, 0.35 mmol) in THF (2 mL) at rt. After 15 min at rt, the reaction mixture was cooled to −55° C. for 10 min before a solution of 5-carboxypentyltriphenylphosphonium bromide (207 mg, 0.45 mmol) was added via cannula. After 10 min at −55° C., the reaction was allowed to warm to rt. After 18 h at rt, the reaction was quenched with saturated aqueous $NH_4Cl$ (15 mL) and extracted with EtOAc (3×15 mL). Combined extracts were washed with brine (20 mL), dried ($Na_2SO_4$), filtered and concentrated in vacuo. Purification of the residue by preparative thin layer chromatography (5% MeOH/$CH_2Cl_2$) afforded 10.5 mg (9%) of desired alkene 9.

Step 3. Hydrogenation of 9 to Give 10

Palladium on carbon (10 wt. %, 2 mg) was added to a solution of alkene 9 (5.8 mg, 0.017 mmol) in MeOH (1 mL). A hydrogen atmosphere was established by evacuating and refilling with hydrogen (3×) and the reaction mixture was stirred under a balloon of hydrogen for 18 h. The reaction mixture was filtered through celite, washing with MeOH, and the filtrate was concentrated in vacuo to afford 4.1 mg (70%) of the title compound (10).

EXAMPLE 6

5-{(R)-1-[4-(1-Hydroxy-hexyl)-phenyl]-5-oxo-pyrrolidin-2-ylmethoxymethyl}-furan-2-carboxylic acid (17)

Step 1. Arylation of 1 to Give 12

A solution of amide 1 (2.89 g, 12.60 mmol) in 1,4-dioxane (20 mL) followed by a solution of 1-(4-methoxybenzyloxymethyl)-4-bromobenzene (11: for synthesis, see Allergan docket #17693; 3.88 g, 12.63 mmol) were added sequentially to a mixture of xantphos (877 mg, 1.52 mmol), $Pd_2(dba)_3$ (463 mg, 0.51 mmol) and $Cs_2CO_3$ (3.2 g, 9.82 mmol) via cannula. The reaction mixture was purged with nitrogen and then heated at reflux for 22 h. The reaction mixture was allowed to cool to rt then filtered through celite, washing with $CH_2Cl_2$, and the filtrate was concentrated in vacuo. Purification of the residue by flash column chromatography on silica gel (5%→25% EtOAc/Hexane, gradient) afforded 1.70 g (30%) of desired product 12.

Step 2. Deprotection of 12 to Give 13

HF-pyridine (5 mL) was added to a solution of silyl ether 12 (1.38 g, 3.03 mmol) in MeCN (15 mL) in a plastic bottle at 0° C. The reaction was stirred at 0° C. for 3 h, then was quenched with saturated aqueous $NaHCO_3$ (250 mL). The mixture was extracted with EtOAc (3×100 mL). The combined extracts were washed with brine (100 mL) then dried ($Na_2SO_4$), filtered and concentrated in vacuo. Purification of the residue by flash column chromatography on silica gel (1%→3% MeOH/$CH_2Cl_2$, gradient) afforded 464 mg (45%) of desired alcohol 13.

Step 3. Alkylation of Alcohol 13 to Give 14

Potassium hydride (44 mg, 1.10 mmol) and 18-crown-6 (365 mg, 1.38 mmol) were added sequentially to a solution of alcohol 13 (315 mg, 0.92 mmol) in THF (4 mL) at 0° C. After 1 h at 0° C., ethyl 5-chloromethylfuran-2-carboxylate (0.28 mL, 1.82 mmol) was added and the reaction was allowed to warm to rt. After 22 h, the reaction was quenched with 0.5 N HCl (20 mL) and extracted with EtOAc (3×25 mL). Combined extracts were washed with brine (50 mL) then dried ($Na_2SO_4$), filtered and concentrated in vacuo. Purification of the residue by flash column chromatography on silica gel (20% EtOAc/Hexane→EtOAc, gradient) afforded 148 mg (32%) of desired product 14.

Step 4. Oxidative Deprotection of 14 to Give 15 and 16

2,3-Dichloro-5,6-dicyano-1,4-benzoquinone (DDQ, 82 mg, 0.36 mmol) was added to a mixture of 14 (143 mg, 0.29 mmol) in $CH_2Cl_2$ (4 mL) and water (0.2 mL). After 3 h, tlc indicated that starting material remained and another portion of DDQ (82 mg, 0.36 mmol) was added. After a further 1.25 h, the reaction was quenched with saturated aqueous $NaHCO_3$ (20 mL). The mixture was extracted with EtOAc (3×20 mL). The combined extracts were washed with brine (20 mL) then dried ($Na_2SO_4$), filtered and concentrated in vacuo. Purification of the residue by flash column chromatography on silica gel ($CH_2Cl_2 \rightarrow 3\%$ MeOH/$CH_2Cl_2$, gradient) afforded 38 mg (35%) of the desired alcohol 15 and 61 mg of impure aldehyde 16. Aldehyde 16 was further purified by preparative thin layer chromatography (5% MeOH/$CH_2Cl_2$) to afford 48.7 mg (45%) of aldehyde 16.

Step 5. Oxidation of 15 to Give 16

Molecular sieves (4 Å, 3 mg), 4-methylmorpholine N-oxide (12.6 mg, 0.11 mmol) and tetrapropylammonium perruthenate (2.5 mg, 0.007 mmol) were added sequentially to a solution of alcohol 15 (26.8 mg, 0.072 mmol) in $CH_2Cl_2$ (1.5 mL) at rt. After 20 min, the reaction mixture was filtered through celite, washing with $CH_2Cl_2$ (5 mL). The filtrate was concentrated in vacuo. Purification of the residue by preparative thin layer chromatography (5% MeOH/$CH_2Cl_2$) afforded 9.6 mg (36%) of the desired aldehyde 16.

Step 6. Grignard Reaction with 16 to Give the Ester of 17

Pentyl magnesium bromide (2.0 M in $Et_2O$, 32 µL, 0.064 mmol) was added to a solution of aldehyde 16 (21.7 mg, 0.058 mmol) in THF (0.4 mL) at −40° C. under nitrogen. After 25 min, the reaction was quenched with saturated aqueous $NH_4Cl$ and extracted with $CH_2Cl_2$ (3×7 mL). Combined extracts were dried ($Na_2SO_4$), filtered and concentrated in vacuo. Purification of the residue by preparative thin layer chromatography (5% MeOH/$CH_2Cl_2$) afforded 10.6 mg (41%) of the desired ester.

Step 7. Saponification to Give 17

Aqueous lithium hydroxide (1 N, 0.1 mL) was added to a solution of ester from step 6 above (8.8 mg, 0.02 mmol) in THF (0.2 mL). After 1 h at rt, the reaction was acidified with 0.5 N HCl (1 mL) then extracted with $CH_2Cl_2$ (3×7 mL).

Combined extracts were dried (Na₂SO₄), filtered and concentrated in vacuo to afford 8.2 mg (99%) of the title compound (17).

EXAMPLE 7

5-{(R)-1-[4-(1-Hydroxy-2-methyl-propyl)-phenyl]-5-oxo-pyrrolidin-2-ylmethoxymethyl}-furan-2-carboxylic acid (18)

Step 1. Grignard Reaction with 16 to Give the Ester of 18

Isopropyl magnesium chloride (2.0 M in THF, 31 μL, 0.062 mmol) was added to a solution of aldehyde 16 (20.5 mg, 0.055 mmol) in THF (0.4 mL) at −40° C. under nitrogen. After 35 min, the reaction was quenched with saturated aqueous NH₄Cl and extracted with CH₂Cl₂ (3×7 mL). Combined extracts were dried (Na₂SO₄), filtered and concentrated in vacuo. Purification of the residue by preparative thin layer chromatography (5% MeOH/CH₂Cl₂) afforded 5 mg (22%) of the desired ester.

Step 2. Saponification to Give 18

Aqueous lithium hydroxide (1 N, 0.05 mL) was added to a solution of the ester from step 1 above (3.1 mg, 0.007 mmol) in THF (0.15 mL). After 1 h at rt, the reaction was acidified with 0.2 N HCl (1 mL) then extracted with CH₂Cl₂ (3×7 mL). Combined extracts were dried (Na₂SO₄), filtered and concentrated in vacuo to afford 2.5 mg (86%) of the title compound (18).

EXAMPLE 8

5-{(R)-1-[4-(1-Hydroxy-2-phenyl-ethyl)-phenyl]-5-oxo-pyrrolidin-2-ylmethoxymethyl}-furan-2-carboxylic acid (19)

Step 1. Grignard Reaction with 16 to Give the Ester of 19

Benzyl magnesium chloride (2.0 M in THF, 14 μL, 0.028 mmol) was added to a solution of aldehyde 16 (9.6 mg, 0.026 mmol) in THF (0.3 mL) at −40° C. under nitrogen. After 45 min, the reaction was warmed to 0° C. After 25 min at 0° C., the reaction was quenched with saturated aqueous NH₄Cl and extracted with CH₂Cl₂ (3×7 mL). Combined extracts were dried (Na₂SO₄), filtered and concentrated in vacuo. Purification of the residue by preparative thin layer chromatography (7% MeOH/CH₂Cl₂) afforded 3.3 mg (28%) of the desired ester.

Step 2. Saponification to Give 19

Aqueous lithium hydroxide (1 N, 0.05 mL) was added to a solution of the ester from step 1 above (2.4 mg, 0.005 mmol) in THF (0.15 mL). After 2.5 h at rt, the reaction was acidified with 0.2 N HCl (1 mL) then extracted with CH₂Cl₂ (3×7 mL). Combined extracts were dried (Na₂SO₄), filtered and concentrated in vacuo to afford 2.2 mg (98%) of the title compound (19)

EXAMPLE 9

5-{(R)-1-[4-(1-Hydroxy-hexyl)-phenyl]-5-oxo-pyrrolidin-2-ylmethoxymethyl}-thiophene-2-carboxylic acid (23)

Step 1. Alkylation of 13 to Give 20

Potassium hydride (55.5 mg, 1.38 mmol) and 18-crown-6 (456 mg, 1.73 mmol) were added sequentially to a solution of alcohol 13 (394 mg, 1.15 mmol) in THF (5 mL) at 0° C. After 1 h at 0° C., a solution of methyl 5-chloromethylthiophene-2-carboxylate (439 mg, 2.30 mmol) in THF (2 mL) was added via cannula and the reaction was allowed to warm to rt. After 19 h, tlc analysis showed starting material remained. Another portion of KH (20 mg, 0.50 mmol) was added and the reaction was heated at 50° C. After 2 h at 50° C., the reaction was cooled and quenched with 0.5 N HCl (20 mL) and extracted with EtOAc (3×25 mL). Combined extracts were washed with brine (50 mL) then dried (Na₂SO₄), filtered and concentrated in vacuo. Purification of the residue by flash column chromatography on silica gel (15% EtOAc/Hexane→EtOAc, gradient) afforded 108 mg (19%) of desired product 20.

Step 2. Oxidative Deprotection of 20 to Give 21 and 22

DDQ (91 mg, 0.40 mmol) was added to a mixture of 20 (98 mg, 0.20 mmol) in CH₂Cl₂ (3 mL) and water (0.15 mL). After 4.5 h, the reaction was quenched with saturated aqueous NaHCO₃ (15 mL) and extracted with EtOAc (3×25 mL). Combined extracts were washed with brine (40 mL) then dried (Na₂SO₄), filtered and concentrated in vacuo. Purification of the residue by preparative thin layer chromatography (5% MeOH/CH₂Cl₂) afforded 14.4 mg (19%) of alcohol 21 and 16.2 mg (22%) of aldehyde 22.

Step 3. Grignard Reaction with 22 to Give the Ester of 23

Pentyl magnesium bromide (2.0 M in Et₂O, 22 μL, 0.044 mmol) was added to a solution of aldehyde 22 (11 mg, 0.029 mmol) in THF (0.2 mL) at −40° C. under nitrogen. After 1.5 h, the reaction was quenched with saturated aqueous NH₄Cl and extracted with CH₂Cl₂ (3×7 mL). Combined extracts were dried (Na₂SO₄), filtered and concentrated in vacuo. Purification of the residue by preparative thin layer chromatography (5% MeOH/CH₂Cl₂) afforded 4.8 mg (37%) of the desired ester.

Step 4. Saponification to Give 23

Rabbit liver esterase (134 units/mg, 1 mg) was added to a solution of the ester from step 3 above (3.6 mg, 0.008 mmol) in MeCN (0.1 mL) and pH 7.2 buffer (2.5 mL). After 16.5 h at rt, the reaction was diluted with MeCN (7 mL) and concentrated in vacuo. The residue was suspended in CH₂Cl₂ and filtered through a cotton plug. The filtrate was concentrated in vacuo to afford 2.0 mg (57%) of the title compound (23).

EXAMPLE 10

5-{(R)-1-[4-(1-Hydroxy-hexyl)-phenyl]-5-oxo-pyrrolidin-2-ylmethoxymethyl}-thiophene-2-carboxylic acid isopropyl ester (28)

Step 1. Arylation of 1 to Give 24

A solution of amide 1 (3.37 g, 14.7 mmol) in 1,4-dioxane (30 mL) was added to a mixture of Pd₂(dba)₃ (540 mg, 0.59 mmol), xantphos (1.02 g, 1.76 mmol) and Cs₂CO₃ (5.74 g, 17.6 mmol). A solution of 1-(1-(4-methoxybenzyloxyhexyl)-4-bromobenzene (preparation 1, 4.99 g, 13.22 mmol) in 1,4-dioxane (30 mL) was added via cannula, followed by an additional 40 mL of 1,4-dioxane. The reaction mixture was purged with nitrogen then heated at reflux overnight. After 20 h, the reaction was cooled to rt and filtered through celite, washing with CH₂Cl₂. The filtrate was concentrated in vacuo and the residue was purified by flash column chromatography on silica gel (5%→30% EtOAc/Hexane, gradient) to afford 5.79 g (83%) of the desired product 24.

Step 2. Deprotection of 24 to Give 25

HF-pyridine (7 mL) was added to a solution of silyl ether 24 (4.05 g, 7.72 mmol) in MeCN (40 mL) in a plastic bottle at 0° C. The reaction was stirred at 0° C. for 1 h, then was quenched with saturated aqueous NaHCO₃ (300 mL). The mixture was extracted with EtOAc (3×150 mL). The combined extracts were washed with brine (200 mL) then dried (Na₂SO₄), filtered and concentrated in vacuo. Purification of the residue by flash column chromatography on silica (CH$_2$Cl$_2$→3% MeOH/CH$_2$Cl$_2$, gradient) afforded 2.3 g (72%) of the desired alcohol 25.

Step 3. Alkylation of 25 to Give 26

Potassium hydride (155 mg, 3.86 mmol) was added to a solution of alcohol 25 (1.22 g, 2.97 mmol) in THF (7 mL) at 0° C. After 15 min at 0° C., 18-crown-6 (1.02 g, 3.86 mmol) was added. After 45 min longer at 0° C., a solution of isopropyl 5-chloromethylthiophene-2-carboxylate (preparation 2, 650 mg, 2.97 mmol) in THF (5 mL) was added via cannula. Potassium iodide (50 mg, 0.30 mmol) was added and the reaction was allowed to warm to rt. After 20 h, the reaction was quenched with 0.5 N HCl (70 mL) and extracted with EtOAc (3×100 mL). Combined extracts were washed with brine (100 mL) then dried (Na$_2$SO$_4$), filtered and concentrated in vacuo. Purification of the residue by flash column chromatography on silica gel (20% EtOAc/Hexane→EtOAc, gradient) afforded 296 mg (17%) of desired product 26 along with 747 mg (61%) of recovered starting alcohol 25.

Step 4. Oxidative Deprotection of 26 to Give 27 and 28

DDQ (93 mg, 0.41 mmol) was added to a solution of 26 (220 mg, 0.37 mmol) in CH$_2$Cl$_2$ (4 mL) and water (0.2 mL) at 0° C. under nitrogen. After 35 min, the reaction was quenched with saturated aqueous NaHCO$_3$ (30 mL) and extracted with EtOAc (3×30 mL). Combined extracts were washed with brine (50 mL) then dried (Na$_2$SO$_4$), filtered and concentrated in vacuo. Purification of the residue by flash column chromatography on silica gel (20%→70% EtOAc/Hexane, gradient) afforded 13 mg (7%) of ketone 27 and 108 mg (62%) of the title compound (28).

EXAMPLE 11

3-{(R)-1-[4-(1-Hydroxy-hexyl)-phenyl]-5-oxo-pyrrolidin-2-ylmethoxymethyl}-benzoic acid (31)

Step 1. Alkylation of 13 to Give 29

Potassium hydride (16 mg, 0.39 mmol) was added to a solution of alcohol 13 (112 mg, 0.33 mmol) in THF (1.0 mL) at 0° C. After 1 h at 0° C., 18-crown-6 (114 mg, 0.43 mmol), potassium iodide (5 mg, 0.03 mmol) and a solution of methyl 3-chloromethylbenzoate (121 mg, 0.66 mmol) in THF (0.5 mL) were added sequentially. The reaction was allowed to warm to rt. After 19 h, the reaction was quenched with 0.1 N HCl (10 mL) and extracted with EtOAc (3×10 mL). Combined extracts were washed with brine (15 mL) then dried (Na$_2$SO$_4$), filtered and concentrated in vacuo. Purification of the residue by flash column chromatography on silica gel (20% EtOAc/Hexane→EtOAc, gradient) afforded 23 mg (14%) of desired product 29.

Step 2. Oxidative Deprotection of 29 to Give 30

DDQ (23 mg, 0.10 mmol) was added to a mixture of 29 (23 mg, 0.047 mmol) in CH$_2$Cl$_2$ and water (20:1, 0.25 mL). After 3.75 h, the reaction was quenched with saturated aqueous NaHCO$_3$ (10 mL) and extracted with EtOAc (3×7 mL). Combined extracts were washed with brine (10 mL) then dried (Na$_2$SO$_4$), filtered and concentrated in vacuo. Purification of the residue by preparative thin layer chromatography (80% EtOAc/Hex) afforded 13 mg (58%) of aldehyde 30.

Step 3. Grignard Reaction with 30 to Give the Ester of 31

Pentyl magnesium bromide (2.0 M in Et$_2$O, 50 µL, 0.10 mmol) was added to a solution of aldehyde 30 (12.4 mg, 0.034 mmol) in THF (0.1 mL) at −40° C. under nitrogen. After 1 h, the reaction was quenched with saturated aqueous NH$_4$Cl (7 mL) and extracted with CH$_2$Cl$_2$ (3×7 mL). Combined extracts were dried (Na$_2$SO$_4$), filtered and concentrated in vacuo. Purification of the residue by preparative thin layer chromatography (5% MeOH/CH$_2$Cl$_2$) afforded 8.6 mg (58%) of the desired ester.

Step 4. Saponification to Give 31

Rabbit liver esterase (134 units/mg, 1 mg) was added to a solution of the ester from step 3 above (7.4 mg, 0.017 mmol) in MeCN (0.1 mL) and pH 7.2 buffer (2.5 mL). After 18 h at rt, the reaction was diluted with MeCN (7 mL) and concentrated in vacuo. Purification of the residue by preparative thin layer chromatography (5% MeOH/CH$_2$Cl$_2$) afforded 1.5 mg (21%) of the title compound (31).

EXAMPLE 12

5-{(R)-1-[4-(1-Hydroxy-pentyl)-phenyl]-5-oxo-pyrrolidin-2-ylmethoxymethyl}-thiophene-2-carboxylic acid (32)

Step 1. Grignard Reaction with 22 to Give the Ester of 32 n-Butyl magnesium chloride (2.0 M in THF, 41 µL, 0.082 mmol) was added to a solution of aldehyde 22 (20.2 mg, 0.054 mmol) in THF (0.1 mL) at −40° C. under nitrogen. After 1 h, the reaction was quenched with saturated aqueous NH$_4$Cl (10 mL) and extracted with CH$_2$Cl$_2$ (3×7 mL). Combined extracts were dried (Na$_2$SO$_4$), filtered and concentrated in vacuo. Purification of the residue by preparative thin layer chromatography (5% MeOH/CH$_2$Cl$_2$) afforded 12.3 mg (53%) of the desired ester.

Step 2. Saponification to Give 32

Rabbit liver esterase (134 units/mg, 1 mg) was added to a solution of the ester from step 1 above (11.2 mg, 0.026 mmol) in MeCN (0.1 mL) and pH 7.2 buffer (3.0 mL). After 19 h at rt, the reaction was diluted with MeCN (10 mL) and concentrated in vacuo. The residue was suspended in 5% MeOH/CH$_2$Cl$_2$ and filtered through a cotton plug. The filtrate was concentrated in vacuo to afford 10.7 mg (99%) of the title compound (32).

EXAMPLE 13

5-{(R)-1-[4-(1-Hydroxy-heptyl)-phenyl]-5-oxo-pyrrolidin-2-ylmethoxymethyl}-thiophene-2-carboxylic acid (33)

Step 1. Grignard Reaction with 22 to Give the Ester of 33 n-Hexyl magnesium bromide (2.0 M in Et$_2$O, 100 µL, 0.20 mmol) was added to a solution of aldehyde 22 (24.6 mg, 0.054 mmol) in THF (0.12 mL) at −40° C. under nitrogen. After 1.5 h, the reaction was quenched with saturated aqueous NH$_4$Cl (10 mL) and extracted with CH$_2$Cl$_2$ (3×7 mL). Combined extracts were dried (Na$_2$SO$_4$), filtered and concentrated in vacuo. Purification of the residue by preparative thin layer chromatography (5% MeOH/CH$_2$Cl$_2$) afforded 16.3 mg (54%) of the desired ester.

Step 2. Saponification to Give 33

Rabbit liver esterase (134 units/mg, 1 mg) was added to a solution of the ester from step 1 above (13 mg, 0.028 mmol) in MeCN (0.1 mL) and pH 7.2 buffer (3.0 mL). After 18 h at rt, the reaction was diluted with MeCN (10 mL) and concentrated in vacuo. The residue was suspended in 5% MeOH/CH$_2$Cl$_2$ and filtered through a cotton plug. The filtrate was concentrated in vacuo to afford 11 mg (87%) of the title compound (33).

EXAMPLE 14

5-{(R)-1-[4-(1-Hydroxy-butyl)-phenyl]-5-oxo-pyrrolidin-2-ylmethoxymethyl}-thiophene-2-carboxylic acid (34)

Step 1. Grignard Reaction with 22 to Give the Ester of 34 n-Propyl magnesium chloride (2.0 M in $Et_2O$, 92 µL, 0.18 mmol) was added to a solution of aldehyde 22 (22.9 mg, 0.061 mmol) in THF (0.12 mL) at 40° C. under nitrogen. After 1.75 h, the reaction was quenched with saturated aqueous $NH_4Cl$ (10 mL) and extracted with $CH_2Cl_2$ (3×7 mL). Combined extracts were dried ($Na_2SO_4$), filtered and concentrated in vacuo. Purification of the residue by preparative thin layer chromatography (5% $MeOH/CH_2Cl_2$) afforded 13 mg (51%) of the desired ester.

Step 2. Saponification to Give 34

Rabbit liver esterase (134 units/mg, 1 mg) was added to a solution of the ester from step 1 above (10.8 mg, 0.026 mmol) in MeCN (0.1 mL) and pH 7.2 buffer (3.0 mL). After 17 h at rt, the reaction was diluted with MeCN (10 mL) and concentrated in vacuo. The residue was suspended in 5% $MeOH/CH_2Cl_2$ and filtered through a cotton plug. The filtrate was concentrated in vacuo to afford 10.4 mg (99%) of the title compound (34).

EXAMPLE 15

5-{(R)-1-[4-(1-Hydroxy-propyl)-phenyl]-5-oxo-pyrrolidin-2-ylmethoxymethyl}-thiophene-2-carboxylic acid (35)

Step 1. Grignard Reaction with 22 to Give the Ester of 35

Ethyl magnesium chloride (2.0 M in $Et_2O$, 24 µL, 0.048 mmol) was added to a solution of aldehyde 22 (5.8 mg, 0.016 mmol) in THF (0.1 mL) at −40° C. under nitrogen. After 1.25 h, the reaction was quenched with saturated aqueous $NH_4Cl$ (5 mL) and extracted with $CH_2Cl_2$ (3×5 mL). Combined extracts were dried ($Na_2SO_4$), filtered and concentrated in vacuo. Purification of the residue by preparative thin layer chromatography (5% $MeOH/CH_2Cl_2$) afforded 2.5 mg (40%) of the desired ester.

Step 2. Saponification to Give 35

Rabbit liver esterase (134 units/mg, 1 mg) was added to a solution of the ester from step 1 above (2.8 mg, 0.007 mmol) in MeCN (0.1 mL) and pH 7.2 buffer (2.5 mL). After 17 h at rt, the reaction was diluted with MeCN (10 mL) and concentrated in vacuo. The residue was suspended in 5% $MeOH/CH_2Cl_2$ and filtered through a cotton plug. The filtrate was concentrated in vacuo to afford 2.7 mg (99%) of the title compound (35).

EXAMPLE 16

5-((E and Z)-3-{(R)-1-[4-(1-Hydroxy-hexyl)-phenyl]-5-oxo-pyrrolidin-2-yl}-alkyl)-thiophene-2-carboxylic acid (41)

Step 1. Oxidation of 25 to Give Aldehyde 36

Dess-Martin periodinane (1.63 g, 3.83 mmol) was added to a solution of alcohol 25 (1.43 g, 3.48 mmol) in $CH_2Cl_2$ (12 mL) at rt under nitrogen. After 1 h at rt the reaction was quenched with saturated aqueous $NaHCO_3$ and saturated aqueous $NaHSO_3$ (1:1, 100 mL). The mixture was extracted with $CH_2Cl_2$ (3×150 mL). The combined extracts were dried ($Na_2SO_4$), filtered and concentrated in vacuo. Purification of the residue by flash column chromatography on silica (2% $MeOH/CH_2Cl_2$) afforded 915 mg (64%) of the desired aldehyde 36.

Step 2. Methylenation of 36 to Give Alkene 37

The Tebbe reagent (0.5 M in THF, 4.86 mL, 2.43 mmol) was added to a solution of aldehyde 36 (677 mg, 1.65 mmol) in THF (11 mL) at −40° C. under nitrogen. After 1 h at −40° C. the reaction was quenched by addition of aqueous 2 N NaOH (1.65 mL) and stirred vigorously overnight with the addition of THF (15 mL). The mixture was filtered through celite, washing with excess EtOAc. The filtrate was concentrated in vacuo. Purification of the residue by flash column chromatography on silica (30%→50% EtOAc/Hex) afforded 254 mg (38%) of the desired alkene 37.

Step 3. Metathesis Reaction of 37 to Give Alkene 38

Benzylidene[1,3-bis(2,4,6-trimethylphenyl)-2-imidazolidinylidene]dichloro(tricyclohexylphosphine)-ruthenium (Grubbs' catalyst, 2nd generation, 48 mg, 0.057 mmol) was added to a solution of alkene 37 (230 mg, 0.56 mmol) and methyl 5-allylthiophene-2-carboxylate (preparation 3, 206 mg, 1.13 mmol) in $CH_2Cl_2$ (3.0 mL). The reaction mixture was heated at reflux for 4 h. The reaction mixture was cooled to rt and more catalyst (48 mg, 0.057 mmol) and methyl 5-allylthiophene-2-carboxylate (100 mg, 0.55 mmol) were added. The mixture was heated for 18 h longer at reflux then cooled and concentrated in vacuo. Purification of the residue by flash column chromatography on silica (5%→50% EtOAc/Hex, gradient) afforded 100 mg (32%) of the desired alkene 38 along with 130 mg (57%) of the starting alkene 37.

Step 4. Oxidative Deprotection of 38 to Give 39 and 40

DDQ (58 mg, 0.26 mmol) was added to a mixture of 38 (130 mg, 0.23 mmol) in $CH_2Cl_2$ (3.1 mL) and water (0.16 mL) at 0° C. under nitrogen. After 45 min, the reaction was quenched with saturated aqueous $NaHCO_3$ (40 mL). The mixture was extracted with EtOAc (3×30 mL). The combined extracts were washed with brine (25 mL) then dried ($Na_2SO_4$), filtered and concentrated in vacuo. Purification of the residue by flash column chromatography on silica (50%→75% EtOAc/Hex, gradient) afforded 28 mg of an inseparable mixture of starting material 38 and ketone 39, and 63 mg (62%) of the desired alcohol 40.

Step 5. Saponification of 40 to Give 41

Rabbit liver esterase (134 units/mg, 1 mg) was added to a solution of ester 40 (3.7 mg, 0.008 mmol) in MeCN (0.2 mL) and pH 7.2 buffer (2.5 mL). After 15.5 h at rt, the reaction was diluted with MeCN (8 mL) and concentrated in vacuo. The residue was suspended in 10% $MeOH/CH_2Cl_2$ and filtered through a cotton plug. The filtrate was concentrated in vacuo to afford 3.0 mg (84%) of the title compound (41).

EXAMPLE 17

5-(3-{(S)-1-[4-(1-Hydroxy-hexyl)-phenyl]-5-oxo-pyrrolidin-2-yl}-propyl)-thiophene-2-carboxylic acid (43)

Step 1. Hydrogenation of 40 to Give Ester 42

Palladium on carbon (10 wt. %, 15 mg) was added to a solution of alkene 40 (63 mg, 0.14 mmol) in methanol (3.0 mL). A hydrogen atmosphere was established by evacuating and refilling with hydrogen (3×) and the reaction mixture was stirred under a balloon of hydrogen. After 3 h at rt, the reaction mixture was filtered through celite, washing with MeOH, and the filtrate was concentrated in vacuo to afford 63 mg crude product. $^1H$ NMR analysis showed starting material remaining so the crude material was resubmitted to the conditions above. After 20 h at rt, the reaction mixture was filtered through celite, washing with MeOH, and the filtrate was concentrated in vacuo to afford 60 mg (95%) of the desired ester 42.

Step 2. Saponification of 42 to Give 43.

Aqueous 1 N lithium hydroxide (0.19 mL, 0.19 mmol) was added to a solution of ester 42 (17 mg, 0.038 mmol) in THF (0.38 mL). After 20 h at rt, $H_2O$ (1.0 mL) was added and the mixture was acidified with 1 N aqueous HCl (1.0 mL) and extracted with EtOAc (3×10 mL). The combined extracts were washed with brine (10 mL) then dried ($Na_2SO_4$), filtered and concentrated in vacuo. Purification of the residue by flash column chromatography on silica (EtOAc→25% MeOH/EtOAc, gradient) afforded 14.4 mg (87%) of the title compound (43).

EXAMPLE 18

5-(3-{(S)-1-[4-(1-Hydroxy-hexyl)-phenyl]-5-oxo-pyrrolidin-2-yl}-propyl)-thiophene-2-carboxylic acid isopropyl ester (44)

DBU (5.2 µL, 0.035 mmol) was added to a solution of acid 43 (7.5 mg, 0.017 mmol) in acetone (0.1 mL) at rt under nitrogen. After 10 min, 2-iodopropane (35 µL, 0.35 mmol) was added. After 21 h at rt, the reaction was quenched with 0.01 N HCl (3 mL) and extracted with EtOAc (3×4 mL). The combined extracts were washed with brine (5 mL), dried ($Na_2SO_4$), filtered and concentrated in vacuo. Purification of the residue by flash column chromatography on silica ($CH_2Cl_2$→1% MeOH/$CH_2Cl_2$) afforded 4.6 mg (53%) of the title compound (44).

EXAMPLE 19

5-{3-[(S)-1-(4-Hexanoyl-phenyl)-5-oxo-pyrrolidin-2-yl]-propyl}-thiophene-2-carboxylic acid (46)

Step 1. Oxidation of 38/39 Afford 39

DDQ (5.5 mg, 0.024 mmol) was added to the mixture of ether 38 and ketone 39 from Example 16, step 4 (6.8 mg, 0.012 mmol) in $CH_2Cl_2$ and water (20:1, 0.25 mL) at rt under nitrogen. After 1.5 h, the reaction was quenched with saturated aqueous $NaHCO_3$ (5 mL). The mixture was extracted with EtOAc (3×5 mL). The combined extracts were washed with brine (5 mL) then dried ($Na_2SO_4$), filtered and concentrated in vacuo. Purification of the residue by preparative thin layer chromatography (60% EtOAc/Hex) afforded 1.5 mg (28%) of desired ketone 39.

Step 2. Hydrogenation of 39 to Give Ester 45

Palladium on carbon (10 wt. %, 1 mg) was added to a solution of alkene 39 (1.5 mg, 0.0034 mmol) in methanol (0.5 mL). A hydrogen atmosphere was established by evacuating and refilling with hydrogen (3×) and the reaction mixture was stirred under a balloon of hydrogen.

After 2 h at rt, the reaction mixture was filtered through celite, washing with MeOH, and the filtrate was concentrated in vacuo to afford 1.3 mg (86%) of desired ester 45.

Step 3. Saponification of 45 to Give 46

Rabbit liver esterase (134 units/mg, 1 mg) was added to a solution of ester 45 (1.3 mg, 0.0029 mmol) in MeCN (0.1 mL) and pH 7.2 buffer (2.5 mL). After 23 h at rt, the reaction was diluted with MeCN (10 mL) and concentrated in vacuo. The residue was suspended in 10% MeOH/$CH_2Cl_2$ and filtered through a cotton plug. The filtrate was concentrated in vacuo to afford 1.2 mg (95%) of the title compound (46).

EXAMPLE 20

5-[(R)-1-(4-Hexanoyl-phenyl)-5-oxo-pyrrolidin-2-ylmethoxymethyl]-thiophene-2-carboxylic acid (47)

Rabbit liver esterase (134 units/mg, 1 mg) was added to a solution of ester 27 (Example 10, step 4, 6.6 mg, 0.014 mmol) in MeCN (0.1 mL) and pH 7.2 buffer (2.5 mL). After 17 h at rt, the reaction was diluted with MeCN (8 mL) and concentrated in vacuo. Purification of the residue by preparative thin layer chromatography (4% MeOH/$CH_2Cl_2$) afforded 1 mg (17%) of the title compound (47).

EXAMPLES 21 and 22

5-{(R)-1-[4-(1-Hydroxy-hexyl)-phenyl]-5-oxo-pyrrolidin-2-ylmethoxymethyl}-thiophene-2-carboxylic acid isopropyl ester (faster eluting diastereomer 48) and 5-{(R)-1-[4-(1-Hydroxy-hexyl)-phenyl]-5-oxo-pyrrolidin-2-ylmethoxymethyl}-thiophene-2-carboxylic acid isopropyl ester (slower eluting diastereomer 49)

The two diastereomers of example 10 (28, ~100 mg) were separated on a Waters 600 HPLC instrument employing a Waters 2996 PDA detector and a Whatman Partisil® 10 M20/50 column, 22 mm×500 mm (Cat. No. 4232-220, Q.A. No. 3TA02D80). Using 60% EtOAc/Hex as the eluent and a flow rate of 15 mL/min, the first diastereomer (48, 32.8 mg total isolated) eluted at 55-60 min, and the second diastereomer (49, 52.6 mg total isolated) eluted at 61-70 min.

EXAMPLE 23

5-{(R)-1-[4-(1-Hydroxy-hexyl)-phenyl]-5-oxo-pyrrolidin-2-ylmethoxymethyl}-thiophene-2-carboxylic acid (50)

Aqueous 1 N lithium hydroxide (0.05 mL, 0.05 mmol) was added to a solution of faster eluting ester diastereomer 48 (2.7 mg, 0.0057 mmol) in THF (0.1 mL) and the mixture was heated at reflux overnight. After 17 h, the reaction was cooled to rt, acidified with 0.05 N aqueous HCl (5 mL) and extracted with $CH_2Cl_2$ (3×5 mL). The combined extracts were dried ($Na_2SO_4$), filtered and concentrated in vacuo to afford 2.5 mg (100%) of the title compound (50).

EXAMPLE 24

5-{(R)-1-[4-(1-Hydroxy-hexyl)-phenyl]-5-oxo-pyrrolidin-2-ylmethoxymethyl}-thiophene-2-carboxylic acid (51)

Aqueous 1 N lithium hydroxide (0.05 mL, 0.05 mmol) was added to a solution of slower eluting ester diastereomer 49 (2.8 mg, 0.0059 mmol) in THF (0.1 mL) and the mixture was heated at reflux overnight. After 23 h, the reaction was cooled to rt, acidified with 0.05 N aqueous HCl (5 mL) and extracted with $CH_2Cl_2$ (3×5 mL). The combined extracts were dried ($Na_2SO_4$), filtered and concentrated in vacuo to afford 1.7 mg (67%) of the title compound (51).

EXAMPLES 25 and 26

5-(3-{(S)-1-[4-(1-Hydroxy-hexyl)-phenyl]-5-oxo-pyrrolidin-2-yl}-propyl)-thiophene-2-carboxylic acid methyl ester (faster eluting diastereomer 52) and 5-(3-{(S)-1-[4-(1-hydroxy-hexyl)-phenyl]-5-oxo-pyrrolidin-2-yl}-propyl)-thiophene-2-carboxylic acid methyl ester (slower eluting diastereomer 53)

The two diastereomers from example 17, step 1 (42, ~43 mg) were separated on a Waters 600 HPLC instrument employing a Waters 2996 PDA detector and a Whatman Partisil® 10 M20/50 column, 22 mm×500 mm (Cat. No. 4232-220, Q.A. No. 3TA02D80). Using 55% EtOAc/Hex as the eluent and a flow rate of 15 mL/min, the first diastereomer (52, 16 mg) eluted at 69-75 min, and the second diastereomer (53, 19 mg) eluted at 80-88 min.

EXAMPLE 27

5-(3-{(S)-1-[4-(1-Hydroxy-hexyl)-phenyl]-5-oxo-pyrrolidin-2-yl}-propyl)-thiophene-2-carboxylic acid (54)

Rabbit liver esterase (134 units/mg, 2 mg) was added to a solution of faster eluting ester diastereomer 52 (16 mg, 0.036 mmol) in MeCN (0.2 mL) and pH 7.2 buffer (3.0 mL). After 18 h at rt, the reaction was diluted with MeCN (10 mL) and concentrated in vacuo. The residue was diluted with $CH_2Cl_2$ (5 mL), filtered through a plug of glass wool and concentrated in vacuo. Purification of the residue by preparative thin layer chromatography (EtOAc →25% MeOH/EtOAc, gradient) afforded 12 mg (77%) of the title compound (54).

EXAMPLE 28

5-(3-{(S)-1-[4-(1-Hydroxy-hexyl)-phenyl]-5-oxo-pyrrolidin-2-yl}-propyl)-thiophene-2-carboxylic acid (55)

Rabbit liver esterase (134 units/mg, 2 mg) was added to a solution of slower eluting ester diastereomer 53 (19 mg, 0.043 mmol) in MeCN (0.2 mL) and pH 7.2 buffer (3.0 mL). After 18 h at rt, the reaction was diluted with MeCN (10 mL) and concentrated in vacuo. The residue was diluted with $CH_2Cl_2$ (5 mL), filtered through a plug of glass wool and concentrated in vacuo. Purification of the residue by preparative thin layer chromatography (EtOAc →25% MeOH/EtOAc, gradient) afforded 10.5 mg (57%) of the title compound (55).

EXAMPLE 29

5-(3-{(S)-1-[4-(1-Hydroxy-hexyl)-phenyl]-5-oxo-pyrrolidin-2-yl}-propyl)-thiophene-2-carboxylic acid isopropyl ester (56, from 54 and 52)

DBU (4.2 µL, 0.028 mmol) and 2-iodopropane (19 µL, 0.19 mmol) were added to a solution of acid 54 (8 mg, 0.019 mmol) in acetone (0.15 mL) at rt under nitrogen. After 18 h at rt, the solvent was removed under a stream of nitrogen. The residue was diluted with EtOAc (10 mL) and washed with 0.1 N HCl (2×5 mL) and brine (5 mL) then dried ($Na_2SO_4$), filtered and concentrated in vacuo. Purification of the residue by flash column chromatography on silica ($CH_2Cl_2$→25% MeOH/$CH_2Cl_2$) afforded 1.9 mg (22%) of the title compound (56) and 4 mg (50%) recovered 54.

EXAMPLE 30

5-(3-{(S)-1-[4-(1-Hydroxy-hexyl)-phenyl]-5-oxo-pyrrolidin-2-yl}-propyl)-thiophene-2-carboxylic acid isopropyl ester (57, from 55 and 53)

DBU (4.7 µL, 0.031 mmol) and 2-iodopropane (21 µL, 0.21 mmol) were added to a solution of acid 55 (9 mg, 0.021 mmol) in acetone (0.2 mL) at rt under nitrogen. After 18 h at rt, the solvent was removed under a stream of nitrogen. The residue was diluted with EtOAc (10 mL) and washed with 0.1 N HCl (2×5 mL) and brine (5 mL) then dried ($Na_2SO_4$), filtered and concentrated in vacuo. Purification of the residue by flash column chromatography on silica ($CH_2Cl_2$→25% MeOH/$CH_2Cl_2$) afforded 2.0 mg (20%) of the title compound (57) and 6 mg (67%) recovered 55.

EXAMPLE 31

5-{(R)-1-[4-(1-Hydroxy-heptyl)-phenyl]-5-oxo-pyrrolidin-2-ylmethoxymethyl}-thiophene-2-carboxylic acid isopropyl ester (61)

Step 1. Arylation of 1 to Give 58

$Pd_2(dba)_3$ (550 mg, 0.60 mmol), xantphos (1.04 g, 180 mmol) and $Cs_2CO_3$ (5.87 g, 18.0 mmol) were added sequentially to a solution of amide 1 (3.45 g, 15.0 mmol) in 1,4-dioxane (100 mL). A solution of 1-(1-(4-methoxybenzyloxy-heptyl)-4-bromobenzene (preparation 4, 5.30 g, 13.54 mmol) in 1,4-dioxane (50 mL) was added via cannula. The reaction mixture was purged with nitrogen then heated at reflux overnight. After 17 h, the reaction was cooled to rt and filtered through celite, washing with $CH_2Cl_2$. The filtrate was concentrated in vacuo and the residue was purified by flash column chromatography on silica gel (5% →35% EtOAc/Hexane, gradient) to afford 5.26 g (72%) of the desired product 58.

Step 2. Deprotection of 58 to Give 59

HF-pyridine (8.8 mL) was added to a solution of silyl ether 58 (5.26 g, 9.74 mmol) in MeCN (50 mL) in a plastic bottle at 0° C. After 45 min at 0° C., the reaction was quenched with saturated aqueous $NaHCO_3$ (400 mL). The mixture was extracted with EtOAc (3×200 mL). The combined extracts were washed with brine (200 mL) then dried ($Na_2SO_4$), filtered and concentrated in vacuo. Purification of the residue by flash column chromatography on silica ($CH_2Cl_2$→5% MeOH/$CH_2Cl_2$, gradient) afforded 3.9 g (94%) of the desired alcohol 59 as a pale yellow solid.

Step 3. Alkylation of 59 to Give 60

A round bottom flask was charged with potassium hydride (30 wt % in oil, 138 mg, 1.03 mmol). The material was washed with hexanes (3×1 mL), then suspended in THF (1 mL). The mixture was cooled to 0° C. and a solution of alcohol 59 (339 mg, 0.80 mmol) in THF (1.5 mL) was added via cannula. After 1 h at 0° C., a solution of isopropyl 5-chloromethylthiophene-2-carboxylate (preparation 2, 174 mg, 0.80 mmol) in THF (1.5 mL) was added via cannula. Potassium iodide (14 mg, 0.08 mmol) was added and the reaction was allowed to warm to rt. After 18 h, the reaction was quenched with saturated aqueous $NH_4Cl$ (15 mL) and extracted with EtOAc (3×25 mL). Combined extracts were washed with brine (15 mL) then dried ($Na_2SO_4$), filtered and concentrated in vacuo. Purification of the residue by flash column chromatography on silica gel (20% →75% EtOAc/Hexane, gradient), followed by preparative thin layer chromatography (65% EtOAc/Hexane) afforded 65 mg (14%) of desired product 60.

Step 4. Oxidative Deprotection of 60 to Give 61

DDQ (26 mg, 0.12 mmol) was added to a solution of 60 (65 mg, 0.11 mmol) in $CH_2Cl_2$ (1.4 mL) and water (0.07 mL) at 0° C. under nitrogen. After 40 min, the reaction was quenched with saturated aqueous $NaHCO_3$ (20 mL) and extracted with EtOAc (3×20 mL). Combined extracts were washed with brine (15 mL) then dried ($Na_2SO_4$), filtered and concentrated in vacuo. Purification of the residue by flash column chromatography on silica gel (50%→75% EtOAc/Hexane, gradient), followed by preparative thin layer chromatography (60% EtOAc/Hexane) afforded 36 mg (69%) of the title compound (61).

EXAMPLES 32 and 33

5-{(R)-1-[4-(1-Hydroxy-heptyl)-phenyl]-5-oxo-pyrrolidin-2-ylmethoxymethyl}-thiophene-2-carboxylic acid isopropyl ester (faster eluting diastereomer 62) and 5-{(R)-1-[4-(1-hydroxy-heptyl)-phenyl]-5-oxo-pyrrolidin-2-ylmethoxymethyl}-thiophene-2-carboxylic acid isopropyl ester (slower eluting diastereomer 63)

The two diastereomers of example 31 (61, ~36 mg) were separated on a Waters 600 HPLC instrument employing a Waters 2996 PDA detector and a Whatman Partisil® 10 M20/50 column, 22 mm×500 mm (Cat. No. 4232-220, Q.A. No. 3TA02D80). Using 60% EtOAc/Hex as the eluent and a flow rate of 15 mL/min, the first diastereomer (62, 14.8 mg) eluted at 50-56.5 min, and the second diastereomer (63, 16.4 mg) eluted at 56.5-70 min.

EXAMPLE 34

5-{(R)-1-[4-(1-Hydroxy-heptyl)-phenyl]-5-oxo-pyrrolidin-2-ylmethoxymethyl}-thiophene-2-carboxylic acid (64)

Aqueous 1 N lithium hydroxide (0.05 mL, 0.05 mmol) was added to a solution of faster eluting ester diastereomer 62 (3.5 mg, 0.0072 mmol) in THF (0.1 mL) and the mixture was heated at reflux overnight. After 18 h, the reaction was cooled to rt, diluted with water (2 mL), acidified with 1.0 N aqueous HCl (1 mL) and extracted with EtOAc (3×5 mL). The combined extracts were washed with brine (5 mL), dried ($Na_2SO_4$), filtered and concentrated in vacuo to afford 3.0 mg (94%) of the title compound (64).

EXAMPLE 35

5-{(R)-1-[4-(1-Hydroxy-heptyl)-phenyl]-5-oxo-pyrrolidin-2-ylmethoxymethyl}-thiophene-2-carboxylic acid (65)

Aqueous 1 N lithium hydroxide (0.05 mL, 0.05 mmol) was added to a solution of slower eluting ester diastereomer 63 (3.5 mg, 0.0072 mmol) in THF (0.1 mL) and the mixture was heated at reflux overnight. After 18 h, the reaction was cooled to rt, diluted with water (2 mL), acidified with 1.0 N aqueous HCl (1 mL) and extracted with EtOAc (3×5 mL). The combined extracts were washed with brine (5 mL), dried ($Na_2SO_4$), filtered and concentrated in vacuo to afford 3.2 mg (99%) of the title compound (65).

EXAMPLE 36

5-(3-{(S)-1-[4-(1-Hydroxy-heptyl)-phenyl]-5-oxo-pyrrolidin-2-yl}-propyl)-thiophene-2-carboxylic acid (71)

Step 1. Oxidation of 59 to give aldehyde 66

1-(3-(Dimethylaminopropyl)-3-ethylcarbodiimide hydrochloride (EDCI, 1.43 g, 7.45 mmol) and DMSO (0.70 mL, 9.86 mmol) were added sequentially to a solution of alcohol 59 (1.06 g, 2.48 mmol) in benzene (25 mL) at rt under nitrogen. After 10 min at rt, pyridinium trifluoroacetate (527 mg, 2.73 mmol) was added. After 3 h at rt, the solution was decanted from the oily residue and the residue was washed with benzene (3×15 mL). The combined benzene phases were concentrated in vacuo. Purification of the residue by flash column chromatography on silica ($CH_2Cl_2$→3% MeOH/$CH_2Cl_2$, gradient) afforded 1.0 g (95%) of the desired aldehyde 66.

Step 2. Methylenation of 66 to Give Alkene 67

The Tebbe reagent (0.5 M in THF, 7.0 mL, 3.5 mmol) was added to a solution of aldehyde 66 (1.0 g, 2.36 mmol) in THF (16 mL) at −40° C. under nitrogen. After 1 h at −40° C. the reaction was quenched by addition of aqueous 2 N NaOH (5.25 mL) and stirred vigorously overnight with the addition of THF (20 mL). The mixture was filtered through celite, washing with excess EtOAc. The filtrate was concentrated in vacuo. Purification of the residue by flash column chromatography on silica (40% EtOAc/Hex) afforded 195 mg (20%) of the desired alkene 67.

Step 3. Metathesis Reaction of 67 to Give Alkene 68

Grubbs' second generation catalyst (38 mg, 0.045 mmol) was added to a solution of alkene 67 (190 mg, 0.45 mmol) and methyl 5-allylthiophene-2-carboxylate (preparation 3, 173 mg, 0.95 mmol) in $CH_2Cl_2$ (2.4 mL). The reaction mixture was heated at reflux for 2 h. The reaction mixture was cooled to rt and more catalyst (9 mg, 0.011 mmol) and methyl 5-allylthiophene-2-carboxylate (165 mg, 0.91 mmol) were added. The mixture was heated for 22 h longer at reflux then cooled and concentrated in vacuo. Purification of the residue by flash column chromatography on silica (2 times, first using 5% →50% EtOAc/Hex, gradient then second using $CH_2Cl_2$→3% MeOH/$CH_2Cl_2$, gradient) afforded 180 mg (69%) of the desired alkene 68.

Step 4. Oxidative Deprotection of 68 to Give 69

DDQ (78 mg, 0.34 mmol) was added to a mixture of 68 (180 mg, 0.31 mmol) in $CH_2Cl_2$ (4.1 mL) and water (0.21 mL) at 0° C. under nitrogen. After 45 min at 0° C., the reaction was quenched with saturated aqueous $NaHCO_3$ (50 mL). The mixture was extracted with EtOAc (3×50 mL). The combined extracts were washed with brine (50 mL) then dried ($Na_2SO_4$), filtered and concentrated in vacuo. Purification of the residue by flash column chromatography on silica (50% →66% EtOAc/Hex, gradient) afforded 50 mg (35%) of the desired alcohol 69.

Step 5. Hydrogenation of 69 to Give Ester 70

Palladium on carbon (10 wt. %, 12 mg) was added to a solution of alkene 69 (50 mg, 0.11 mmol) in methanol (2.3 mL). A hydrogen atmosphere was established by evacuating and refilling with hydrogen (3×) and the reaction mixture was stirred under a balloon of hydrogen. After 20 h at rt, the reaction mixture was filtered through celite, washing with MeOH, and the filtrate was concentrated in vacuo to afford 50 mg (99%) of the desired ester 70.

Step 6. Saponification of 70 to Give 71

Aqueous 1 N lithium hydroxide (0.19 mL, 0.19 mmol) was added to a solution of ester 70 (17 mg, 0.038 mmol) in THF (0.4 mL). After 18 h at rt, H$_2$O (1.0 mL) was added and the mixture was acidified with 1 N aqueous HCl (1.0 mL) and extracted with EtOAc (3×10 mL). The combined extracts were washed with brine (10 mL) then dried (Na$_2$SO$_4$), filtered and concentrated in vacuo. Purification of the residue by preparative thin layer chromatography (15% MeOH/CH$_2$Cl$_2$) afforded 5.6 mg (34%) of the title compound (71).

EXAMPLES 37 and 38

5-(3-{(S)-1-[4-(1-Hydroxy-heptyl)-phenyl]-5-oxo-pyrrolidin-2-yl}-propyl)-thiophene-2-carboxylic acid methyl ester (faster eluting diastereomer 72) and 5-(3-{(S)-1-[4-(1-hydroxy-heptyl)-phenyl]-5-oxo-pyrrolidin-2-yl}-propyl)-thiophene-2-carboxylic acid methyl ester (slower eluting diastereomer 73)

The two diastereomers from example 36, step 5 (70, ~34 mg) were separated on a Waters 600 HPLC instrument employing a Waters 2996 PDA detector and a Whatman Partisil® 10 M20/50 column, 22 mm×500 mm (Cat. No. 4232-220, Q.A. No. 3TA02D80). Using 55% EtOAc/Hex as the eluent and a flow rate of 15 mL/min, the first diastereomer (72, 10.7 mg) eluted at 78-87.5 min, and the second diastereomer (73, 7.0 mg) eluted at 91-101 min.

EXAMPLE 39

5-(3-{(S)-1-[4-(1-Hydroxy-heptyl)-phenyl]-5-oxo-pyrrolidin-2-yl}-propyl)-thiophene-2-carboxylic acid (74)

Aqueous 1 N lithium hydroxide (0.12 mL, 0.12 mmol) was added to a solution of faster eluting ester diastereomer 72 (10.7 mg, 0.023 mmol) in THF (0.3 mL). After 66 h at rt, H$_2$O (1.0 mL) was added and the mixture was acidified with 1 N aqueous HCl (1.0 mL) and extracted with EtOAc (3×10 mL). The combined extracts were washed with brine (5 mL) then dried (Na$_2$SO$_4$), filtered and concentrated in vacuo to afford 10 mg (96%) of the title compound (74).

EXAMPLE 40

5-(3-{(S)-1-[4-(1-Hydroxy-heptyl)-phenyl]-5-oxo-pyrrolidin-2-yl}-propyl)-thiophene-2-carboxylic acid (75)

Aqueous 1 N lithium hydroxide (0.08 mL, 0.08 mmol) was added to a solution of slower eluting ester diastereomer 73 (7.0 mg, 0.015 mmol) in THF (0.2 mL). After 66 h at rt, H$_2$O (1.0 mL) was added and the mixture was acidified with 1 N aqueous HCl (1.0 mL) and extracted with EtOAc (3×8 mL). The combined extracts were washed with brine (5 mL) then dried (Na$_2$SO$_4$), filtered and concentrated in vacuo to afford 6.5 mg (96%) of the title compound (75).

EXAMPLE 41

5-(3-{(S)-1-[4-(1-Hydroxy-heptyl)-phenyl]-5-oxo-pyrrolidin-2-yl}-propyl)-thiophene-2-carboxylic acid isopropyl ester (76, from 74 and 72)

DBU (4.0 µL, 0.027 mmol) and 2-iodopropane (36 µL, 0.36 mmol) were added to a solution of acid 74 (8 mg, 0.018 mmol) in acetone (0.2 mL) at rt under nitrogen. After 72 h at rt, the solvent was removed under a stream of nitrogen. The residue was diluted with EtOAc (10 mL) and washed with 0.5 N HCl (2×5 mL) and brine (5 mL) then dried (Na$_2$SO$_4$), filtered and concentrated in vacuo. Purification of the residue by flash column chromatography on silica (EtOAc →20% MeOH/EtOAc) afforded 7.3 mg (83%) of the title compound (76).

EXAMPLE 42

5-(3-{(S)-1-[4-(1-Hydroxy-heptyl)-phenyl]-5-oxo-pyrrolidin-2-yl}-propyl)-thiophene-2-carboxylic acid isopropyl ester (77, from 75 and 73)

DBU (2.5 µL, 0.017 mmol) and 2-iodopropane (22.5 µL, 0.225 mmol) were added to a solution of acid 75 (5 mg, 0.011 mmol) in acetone (0.11 mL) at rt under nitrogen. After 72 h at rt, the solvent was removed under a stream of nitrogen. The residue was diluted with EtOAc (10 mL) and washed with 0.5 N HCl (2×5 mL) and brine (5 mL) then dried (Na$_2$SO$_4$), filtered and concentrated in vacuo. Purification of the residue by flash column chromatography on silica (EtOAc→20% MeOH/EtOAc) afforded 3.2 mg (58%) of the title compound (77).

EXAMPLE 43

4-{(R)-1-[4-(1-Hydroxy-hexyl)-phenyl]-5-oxo-pyrrolidin-2-ylmethoxy}-benzoic acid (80)

Step 1. Mitsunobu Reaction of 25 and Methyl 4-Hydroxybenzoate to Give 78

Diisopropyl azodicarboxylate (DIAD, 194 µL, 1.0 mmol) was added to a solution of alcohol 25 (200 mg, 0.49 mmol), triphenylphosphine (191 mg, 0.73 mmol) and methyl 4-hydroxybenzoate (87 mg, 0.57 mmol) in CH$_2$Cl$_2$ (2.5 mL). After stirring 18 h at rt, the solvent was removed under a stream of nitrogen and the residue was suspended in EtOAc (75 mL). The mixture was washed with saturated aqueous NaHCO$_3$ (3×25 mL) and brine (25 mL) then the organic phase was dried (Na$_2$SO$_4$) filtered and concentrated in vacuo. Purification of the residue by flash column chromatography on silica gel (50% EtOAc/hexane→EtOAc, gradient) afforded 81 mg (31%) of the desired ether 78.

Step 2. Oxidative Deprotection of 78 to Give 79

DDQ (37 mg, 0.16 mmol) was added to a mixture of 78 (81 mg, 0.15 mmol) in CH$_2$Cl$_2$ (2.0 mL) and water (0.1 mL) at 0° C. under nitrogen. After 45 min at 0° C., the reaction was quenched with saturated aqueous NaHCO$_3$ (25 mL). The mixture was extracted with EtOAc (3×25 mL). The combined extracts were washed with brine (25 mL) then dried (Na$_2$SO$_4$), filtered and concentrated in vacuo. Purification of the residue by flash column chromatography on silica (85% EtOAc/Hex→EtOAc, gradient) afforded 31 mg (49%) of the desired alcohol 79.

Step 3. Saponification of 79 to Give 80

Aqueous 1 N lithium hydroxide (0.35 mL, 0.35 mmol) was added to a solution of ester 79 (30 mg, 0.071 mmol) in THF (0.7 mL). After 20 h at rt, water (2.0 mL) was added and the mixture was acidified with 1 N aqueous HCl (1.5 mL) and extracted with EtOAc (3×10 mL). The combined extracts were washed with brine (10 mL) then dried (Na$_2$SO$_4$), filtered and concentrated in vacuo. Purification of the residue by flash column chromatography on silica (EtOAc→10% MeOH/EtOAc, gradient) afforded 11.5 mg (38%) of starting ester 79 and 8.5 mg (29%) of the title compound (80).

Preparation 1

1-(1-(4-Methoxybenzyloxy-hexyl)-4-bromobenzene

Step 1. Pentyl Grignard Addition to 4-Bromobenzaldehyde n-Pentyl magnesium bromide (2.0 M in THF, 27 mL, 54 mmol) was added to a solution of 4-bromobenzaldehyde (5.0 g, 27 mmol) in THF (20 mL) at 0° C. under nitrogen. After 1 h, the reaction was quenched with 3 N HCl and extracted with $Et_2O$ (3×120 mL). Combined extracts were washed with brine (100 mL), dried ($Na_2SO_4$), filtered and concentrated in vacuo. Purification of the residue by flash column chromatography on silica gel (5% EtOAc/Hex) afforded 5.1 g (74%) of 1-(4-bromophenyl)-hexan-1-ol.

Step 2. Protection of the Alcohol as its MPM Ether

Sodium hydride (60% wt. in oil, 0.95 g, 23.8 mmol) was added to a solution of the alcohol from step 1 (5.11 g, 19.9 mmol) in THF and DMF (2:1, 20 mL) at 0° C. under nitrogen. After 1 h at 0° C., 4-methoxybenzyl chloride (3.23 mL, 23.8 mmol) and the reaction was allowed to warm to rt. The reaction was then heated at 80° C. After 17 h, the reaction was allowed to cool to rt, quenched with saturated aqueous $NH_4Cl$ (100 mL) and extracted with EtOAc (3×100 mL). The combined extracts were washed with brine (100 mL), dried ($Na_2SO_4$), filtered and concentrated in vacuo. Purification of the residue by flash column chromatography on silica gel (2% EtOAc/Hex) afforded 7.02 g (94%) of the title compound.

Preparation 2

Isopropyl 5-chloromethylthiophene-2-carboxylate

Step 1. Preparation of the Bis-Isopropyl Ester

DBU (31.3 mL, 209 mmol) and 2-iodopropane (20.9 mL, 209 mmol) were added to a solution of thiophene-2,5-dicarboxylic acid (6.0 g, 34.9 mmol) in acetone (60 mL) at rt under nitrogen. After 21 h at rt, the reaction was quenched with saturated aqueous $NaHCO_3$ (300 mL) and extracted with EtOAc (3×150 mL). The combined extracts were washed with brine (200 mL), dried ($Na_2SO_4$), filtered and concentrated in vacuo to afford 7.59 g (85%) of the diester.

Step 2. Reduction to the Hydroxymethyl Ester

Sodium borohydride (3.36 g, 88.8 mmol) was added to a solution of the diester (7.59 g, 29.6 mmol) in $CH_2Cl_2$/MeOH (1:1, 100 mL) at 0° C. under nitrogen. The ice bath was removed and the reaction was allowed to stir at rt overnight. After 20.5 h at rt the reaction was concentrated in vacuo then aqueous 0.5 N HCl (100 mL) was added. The mixture was extracted with $CH_2Cl_2$ (3×100 mL). The combined extracts were dried ($Na_2SO_4$), filtered and concentrated in vacuo. Purification of the residue by flash column chromatography on silica (5%→60% EtOAc/Hex, gradient) afforded 738 mg (12%) of the alcohol.

Step 3. Conversion of the Alcohol to the Chloride

Methanesulfonyl chloride (0.67 mL, 8.1 mmol) and triethylamine (1.7 mL, 12.2 mmol) were added sequentially and dropwise to a solution of the alcohol (696 mg, 3.48 mmol) in $CH_2Cl_2$ (4.0 mL) at 0° C. under nitrogen. The ice bath was removed and the reaction was allowed to stir overnight at rt. After 17 h, the reaction was quenched with saturated aqueous $NaHCO_3$ (30 mL) and extracted with $CH_2Cl_2$ (3×50 mL). The combined extracts were dried ($Na_2SO_4$), filtered and concentrated in vacuo. Purification of the residue by flash column chromatography on silica (5% EtOAc/Hex) afforded 664 mg (87%) of the title compound.

Preparation 3

Methyl 5-allylthiophene-2-carboxylate

Step 1. Preparation of the Methyl Ester

Acetyl chloride (6.9 mL, 96.6 mmol) was added to a solution of 5-bromo-2-thiophenecarboxylic acid (4.0 g, 19.3 mmol) in methanol (30 mL) at rt. After 17 h at rt, the reaction was heated at reflux for 1.5 h to drive it to completion. The reaction was then cooled to rt and concentrated in vacuo to remove methanol. Saturated aqueous $NH_4Cl$ (120 mL) was added and the mixture was extracted with $CH_2Cl_2$ (3×100 mL). The combined extracts were dried ($Na_2SO_4$), filtered and concentrated in vacuo to afford 3.57 g (84%) of the desired methyl ester as an off white solid.

Step 2. Allylation of the Bromothiophene

Isopropyl magnesium chloride (2.0 M in $Et_2O$, 8.9 mL, 17.8 mmol) was added to a solution of the bromide from step 1 (3.56 g, 16.1 mmol) in THF (10 mL) at −40° C. under nitrogen. The reaction mixture was stirred at 40° C. for 1 h, then copper (I) cyanide (144 mg, 1.61 mmol) and allyl bromide (3.0 mL, 35.4 mmol) were added sequentially. The reaction mixture was stirred at 40° C. for 1 h then was quenched with saturated aqueous $NH_4Cl$ (100 mL) and extracted with EtOAc (3×100 mL). The combined extracts were washed with brine (100 mL), dried ($Na_2SO_4$), filtered and concentrated in vacuo. Purification of the residue by flash column chromatography on silica gel (5% EtOAc/Hex) afforded 2.45 g (83%) of the title compound as a pale yellow oil that solidified on standing.

Preparation 4

1-(1-(4-Methoxybenzyloxy-heptyl)-4-bromobenzene

Step 1. Hexyl Grignard Addition to 4-Bromobenzaldehyde n-Hexyl magnesium bromide (2.0 M in $Et_2O$, 27 mL, 54 mmol) was added to a solution of 4-bromobenzaldehyde (5.0 g, 27 mmol) in THF (20 mL) at 0° C. under nitrogen. After 1.5 h at 0° C., the reaction was quenched slowly with 3 N HCl (20 mL) and concentrated in vacuo. The residue was diluted with water (30 mL) and extracted with $Et_2O$ (3×150 mL). Combined extracts were dried ($Na_2SO_4$), filtered and concentrated in vacuo. Purification of the residue by flash column chromatography on silica gel (5%→10% EtOAc/Hex) afforded 5.6 g (76%) of 1-(4-bromophenyl)-heptan-1-ol.

Step 2. Protection of the Alcohol as its MPM Ether

Sodium hydride (60% wt. in oil, 0.991 g, 24.8 mmol) was added to a solution of the alcohol from step 1 (5.6 g, 20.6 mmol) in THF and DMF (2:1, 30 mL) at 0° C. under nitrogen. After 5 min at 0° C., the reaction was allowed to warm to rt and 4-methoxybenzyl chloride (3.4 mL, 25.0 mmol) was added. The reaction was then heated at 80° C. After 18 h at 80° C., the reaction was allowed to cool to rt, quenched with saturated aqueous $NH_4Cl$ (50 mL) and concentrated in vacuo. The remainder was extracted with EtOAc (3×100 mL). The combined extracts were washed with water (2×100 mL) and brine (75 mL), then dried ($Na_2SO_4$), filtered and concentrated in vacuo. Purification of the residue by flash column chromatography on silica gel (2% EtOAc/Hex) afforded 7.5 g (93%) of the title compound.

| Example# | Structure | EP2 data | | | | EP4 data | |
|---|---|---|---|---|---|---|---|
| | | flipr EC50 | cAMP EC50 | Ki | Ki pH 6.0 | flipr EC50 | KI |
| 1 | 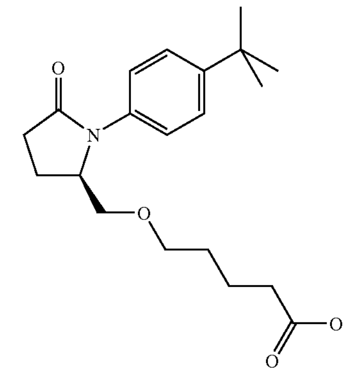 | >10000 | | NA | | >10000 | >10000 |
| 2 | 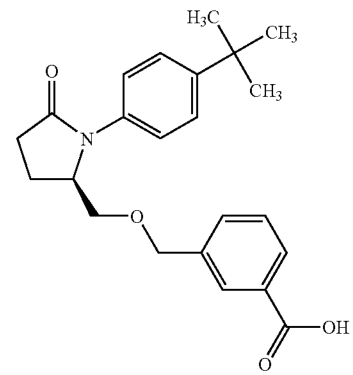 | >10000 | | NA | | >10000 | >10000 |
| 3 | 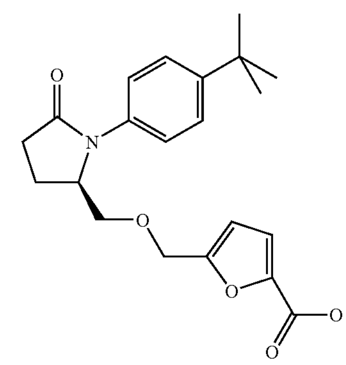 | 442 | 28 | 4000 | 189 | >10000 | >10000 |
| 4 | 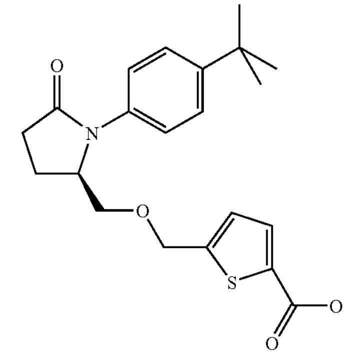 | 1343 | 51 | 501 | 27 | >10000 | >10000 |

-continued
| | | | | | | |
|---|---|---|---|---|---|---|
| 5 | 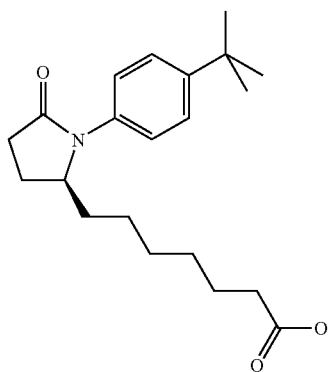 | 4121 | 548 | >10000 | >10000 | >10000 |
| 6 | 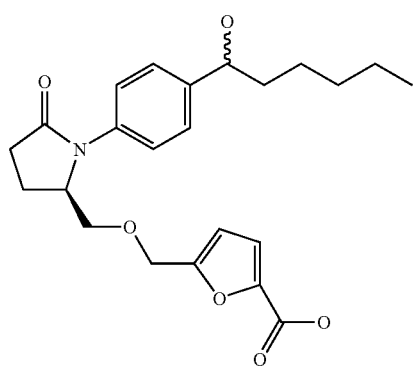 | 388 | 26 | 2028 | NA | >10000 |
| 7 | 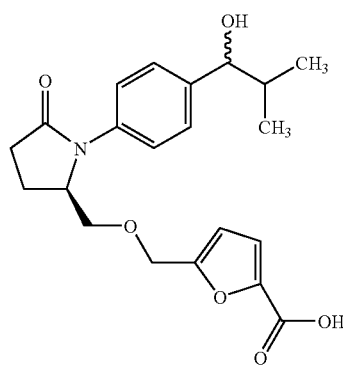 | 7669 | 1218 | >10000 | NA | >10000 |
| 8 | 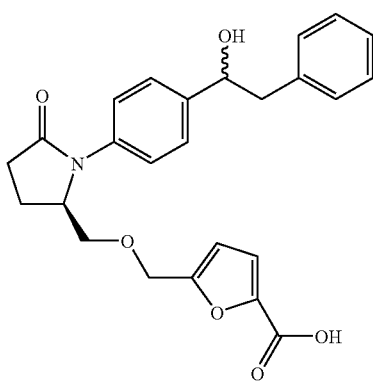 | 1228 | 148 | 2293 | NA | >10000 |

| | | | | | | |
|---|---|---|---|---|---|---|
| 9 | 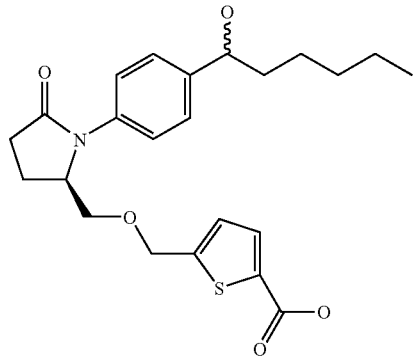 | 8 | 3 | 115 | >10000 | >10000 |
| 11 | 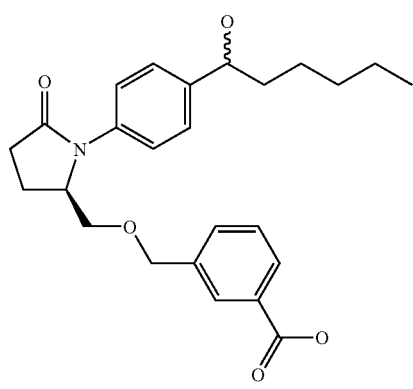 | >10000 | 517 | NA | NA | >10000 |
| 12 | 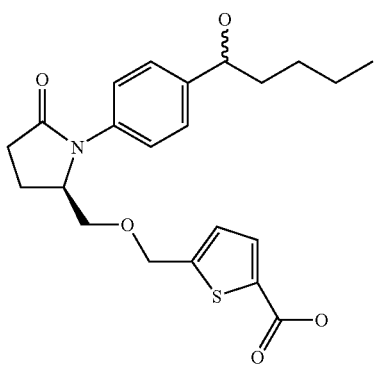 | 212 | 8 | 387 | NA | >10000 |
| 13 | 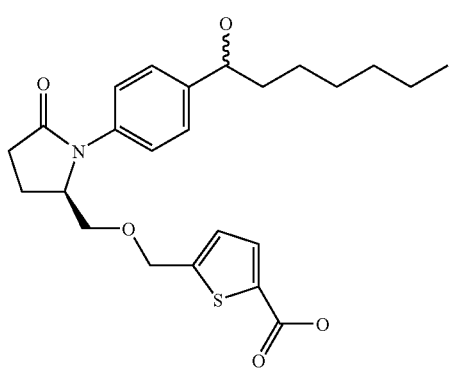 | 20 | 1.5 | 190 | NA | >10000 |

| | | | | | | |
|---|---|---|---|---|---|---|
| 14 | 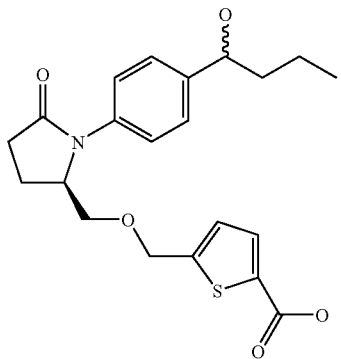 | 426 | 27 | 1639 | NA | >10000 |
| 15 | 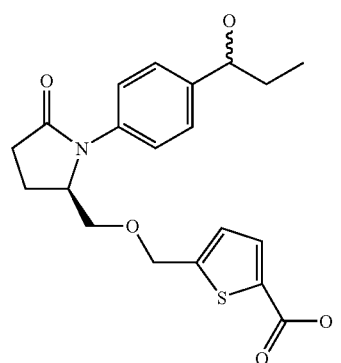 | 1812 | 312 | 5731 | >10000 | >10000 |
| 16 | 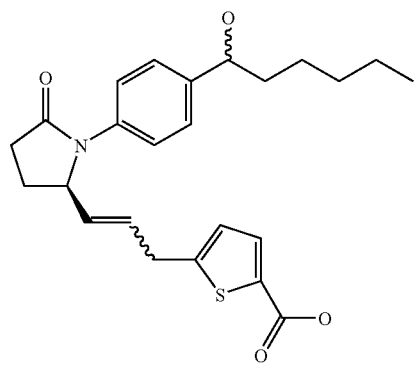 | 226 | 15 | 1382 | NA | >10000 |
| 17 | 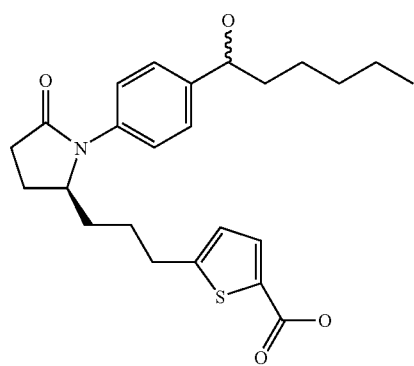 | 5 | 0.55 | 23 | NA | >10000 |

| | | | | | | |
|---|---|---|---|---|---|---|
| 19 | 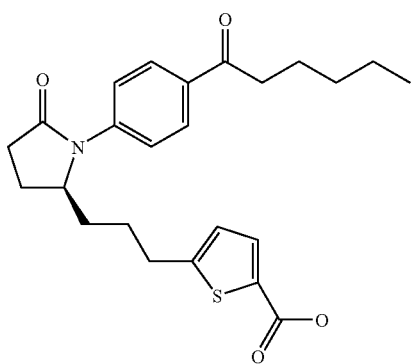 | 16 | 1.6 | 31 | >10000 | >10000 |
| 20 | 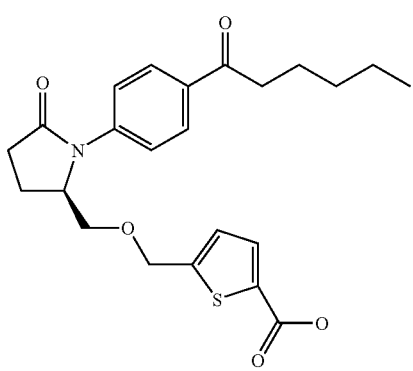 | 215 | 8 | 163 | NA | >10000 |
| 23 | 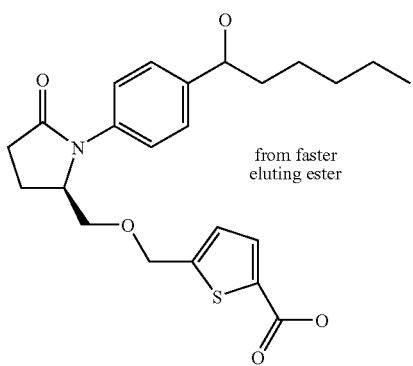 from faster eluting ester | 62 | 5 | 345 | >10000 | >10000 |
| 24 | 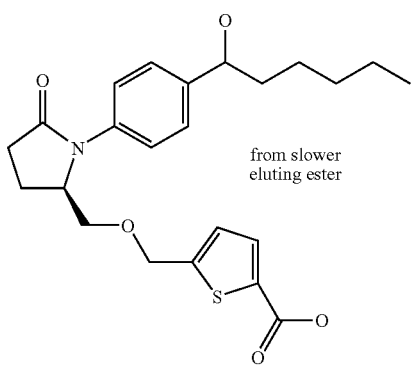 from slower eluting ester | 15 | 1.5 | 116 | >10000 | 6032 |

| | | | | | | |
|---|---|---|---|---|---|---|
| 27 | 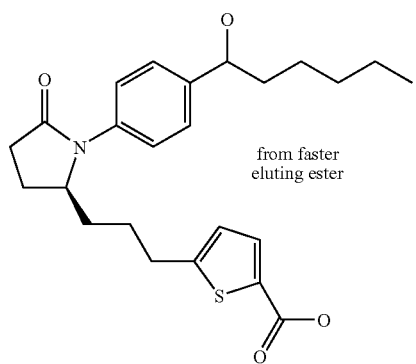 from faster eluting ester | 6 | 0.19 | 21 | >10000 | >10000 |
| 28 | 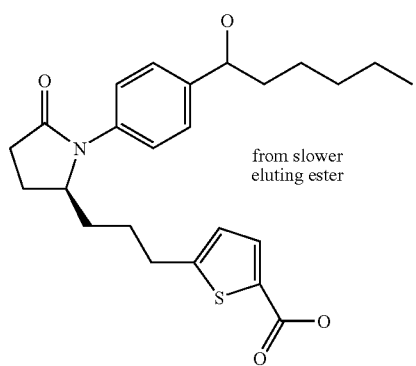 from slower eluting ester | 1.6 | 0.15 | 15 | >10000 | 4849 |
| 34 | 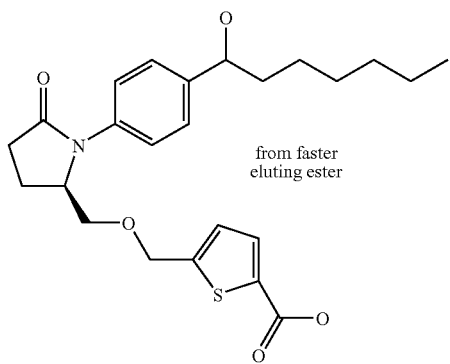 from faster eluting ester | 134 | 7 | 229 | NA | 3842 |
| 35 | 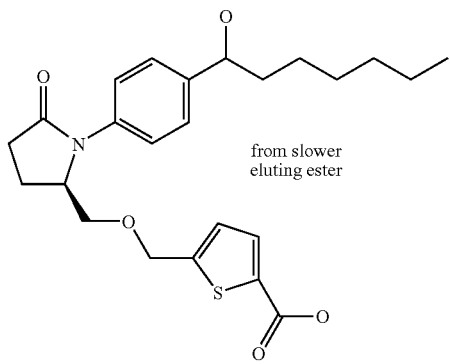 from slower eluting ester | 49 | 4 | 201 | NA | 3288 |

| | | | | | |
|---|---|---|---|---|---|
| 36 | 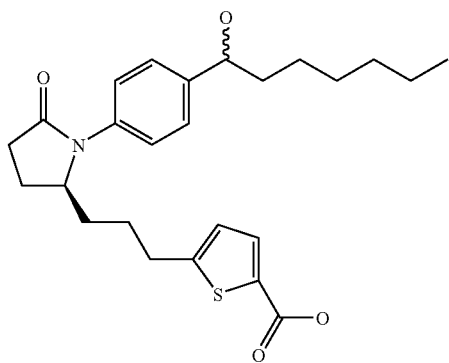 | 30 | 0.9 | 10 | >10000 |
| 39 | 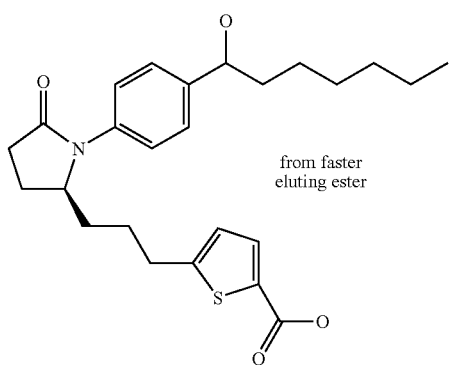<br>from faster eluting ester | 16 | 1.4 | 12 | NA |
| 40 | 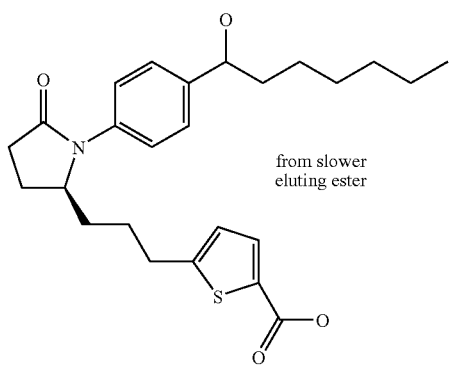<br>from slower eluting ester | 5 | 0.6 | 8 | NA |
| 43 | 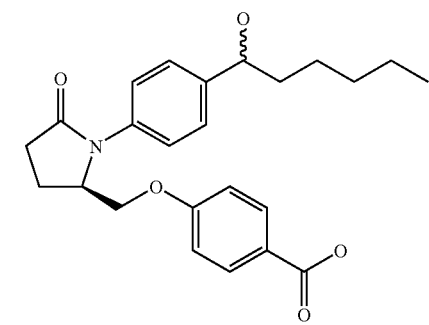 | 7284 | NA | 22726 | NA | 8752 |

-continued
| Example# | Structure | Other Receptors (EC50 in nM) | | | | | |
|---|---|---|---|---|---|---|---|
| | | hFP | hEP1 | hEP3A | hTP | hIP | hDP |
| 1 | 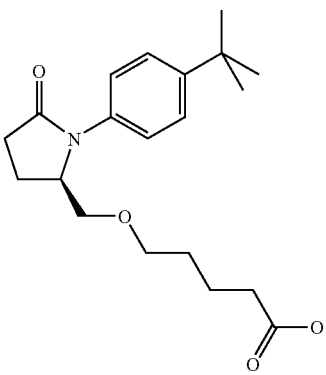 | | | | | | |
| 2 | 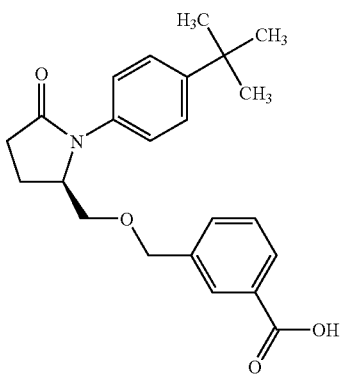 | | | | | | |
| 3 | 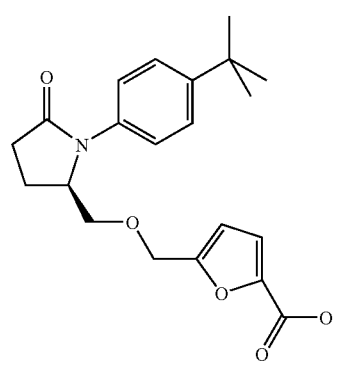 | NA | NA | >10000 | NA | NA | 1921 |
| 4 | 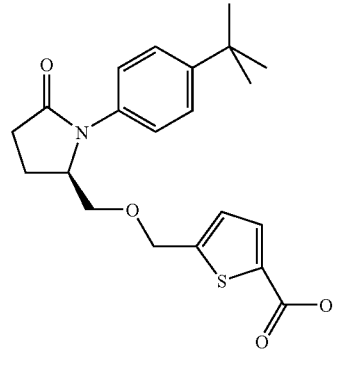 | NA | >10000 | 19234 | >10000 | NA | 2323 |

| | | | | | | |
|---|---|---|---|---|---|---|
| 5 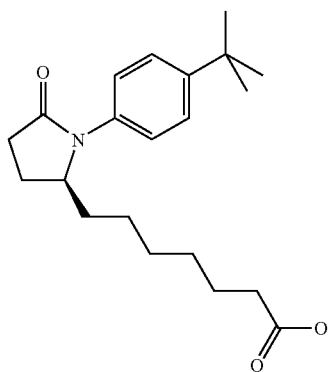 | NA | >10000 | 19544 | NA | NA | >10000 |
| 6 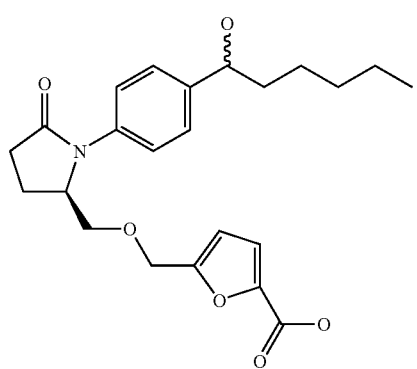 | NA | NA | 1927 | NA | NA | NA |
| 7 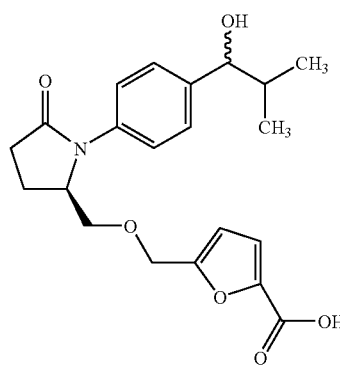 | NA | NA | NA | NA | NA | NA |
| 8 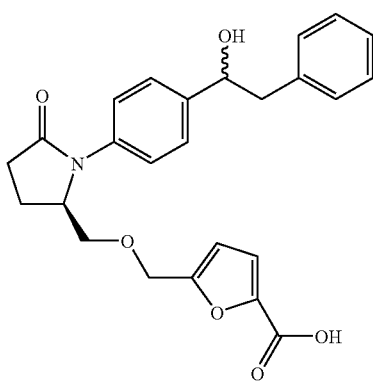 | NA | NA | NA | NA | NA | NA |

-continued
| | | | | | | | |
|---|---|---|---|---|---|---|---|
| 9 | 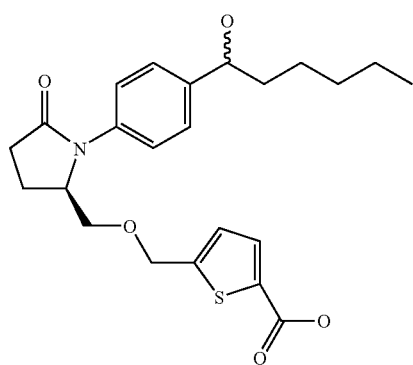 | NA | NA | 403 | NA | NA | 3233 |
| 11 | 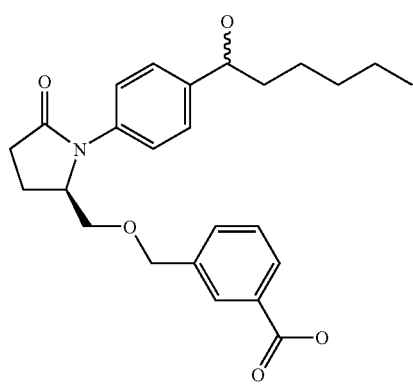 | NA | NA | NA | NA | NA | NA |
| 12 | 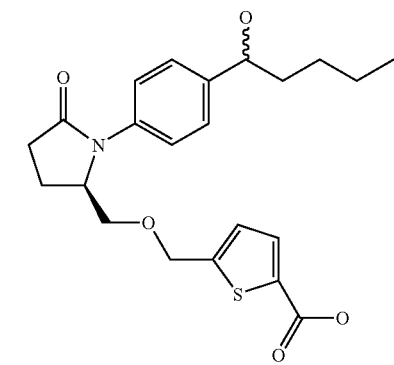 | NA | NA | NA | NA | NA | NA |
| 13 | 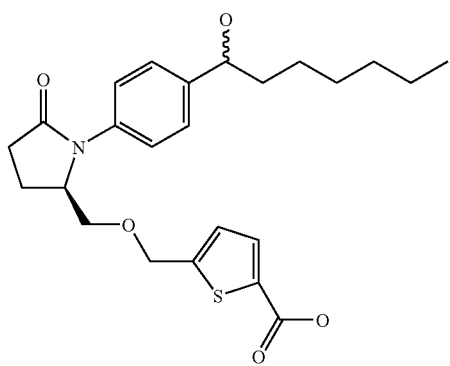 | NA | NA | 519 | NA | NA | 5763 |

| 14 | 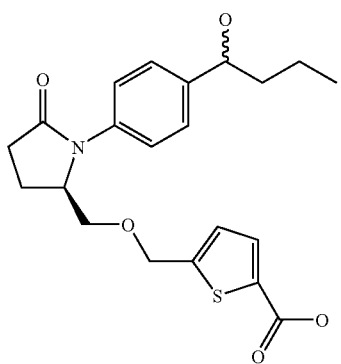 | NA | NA | NA | NA | NA | NA |
| 15 | 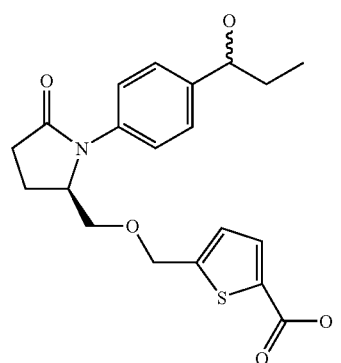 | NA | NA | NA | NA | NA | 7560 |
| 16 | 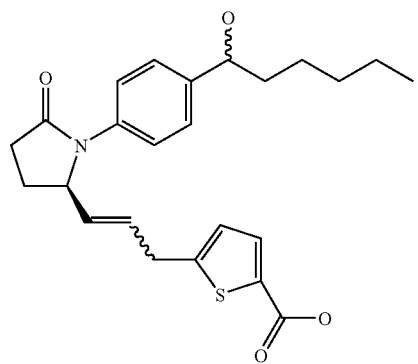 | NA | NA | 1411 | NA | NA | NA |
| 17 | 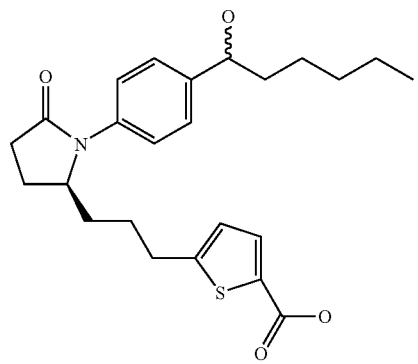 | NA | NA | 155 | NA | NA | 1234 |

| | | | | | | | |
|---|---|---|---|---|---|---|---|
| 19 | 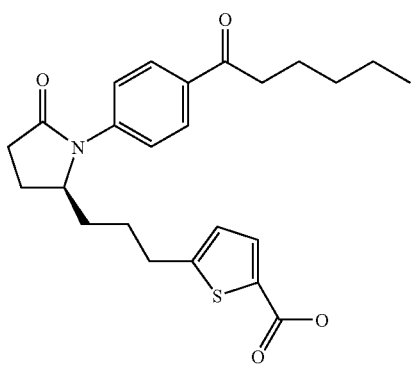 | NA | NA | 2345 | NA | NA | 7695 |
| 20 | 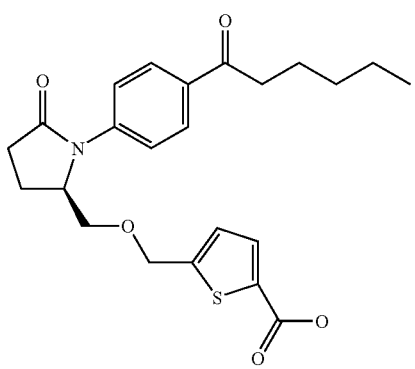 | NA | NA | NA | NA | NA | NA |
| 23 | 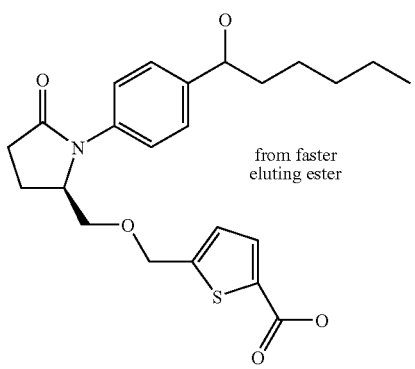  from faster eluting ester | NA | NA | 153 | NA | NA | 7749 |
| 24 | 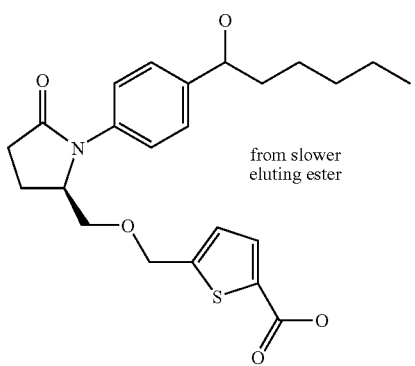  from slower eluting ester | NA | NA | 1205 | NA | NA | 6800 |

| | | | | | | | |
|---|---|---|---|---|---|---|---|
| 27 | 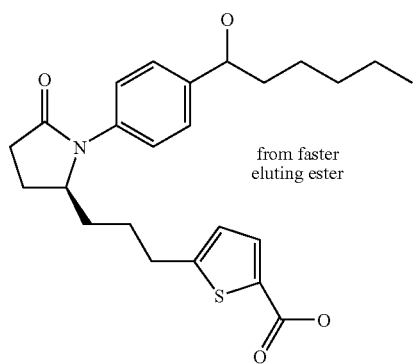from faster eluting ester | NA | NA | 12 | NA | NA | 812 |
| 28 | 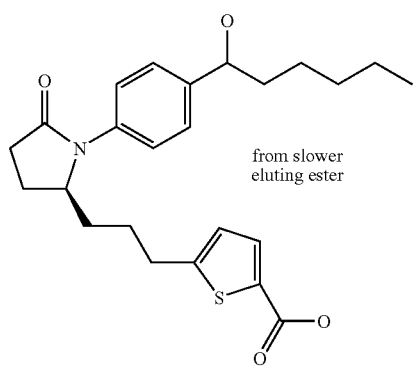from slower eluting ester | NA | NA | 156 | NA | NA | 296 |
| 34 | 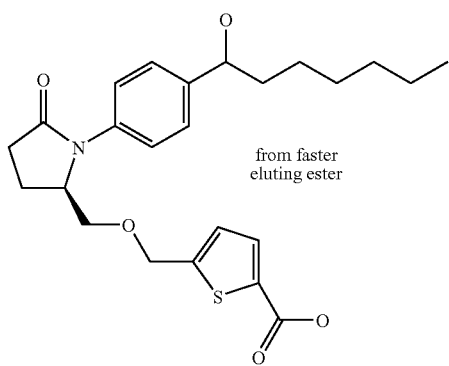from faster eluting ester | NA | NA | 71 | NA | NA | 6829 |
| 35 | 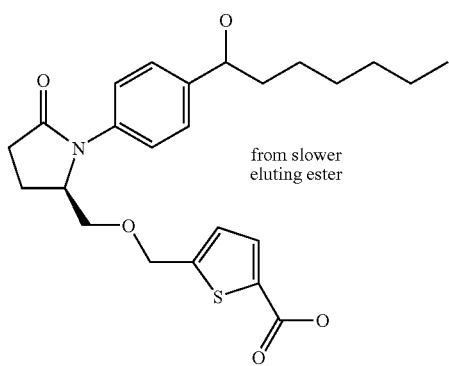from slower eluting ester | NA | NA | 621 | NA | NA | NA |

| # | Structure | | | | | | |
|---|---|---|---|---|---|---|---|
| 36 | 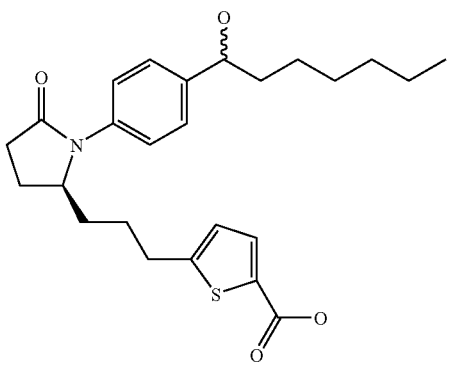 | NA | NA | 47 | NA | NA | 105 |
| 39 | 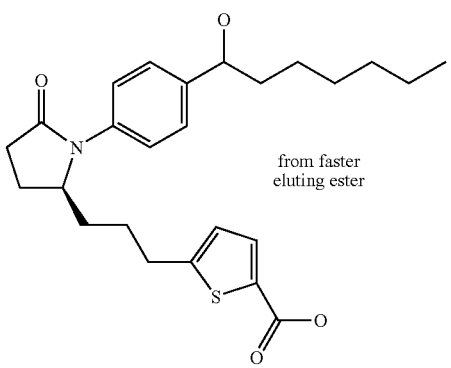<br>from faster eluting ester | NA | 6952 | 7 | NA | NA | 37 |
| 40 | 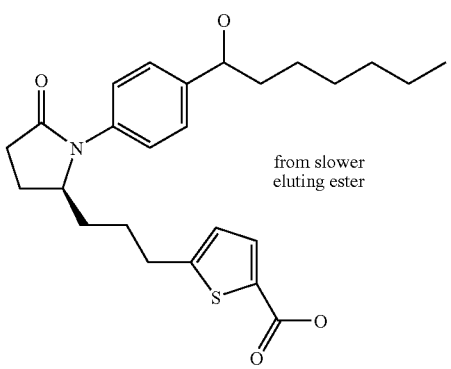<br>from slower eluting ester | NA | NA | 33 | NA | >10000 | 106 |
| 43 | 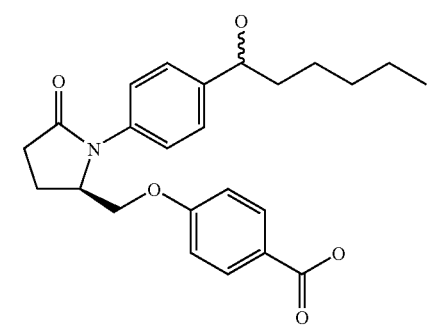 | NA | NA | NA | NA | NA | NA |

Biological Assay Methods

Binding Data
Ki

Competition binding experiments were performed in a medium containing Hank's balanced salt solution, Hepes 20 mM, pH 7.3, membranes (~60 μg protein) or 2×10$^5$ cells from HEK 293 cells stably expressing human EP2 receptors, [$^3$H] PGE2 (10 nM) and various concentrations of test compounds in a total volume of 300 μl. Reaction mixtures were incubated at 23° C. for 60 min, and were filtered over Whatman GF/B filters under vacuum. Filters were washed three times with 5 ml ice-cold buffer containing 50 mM Tris/HCl (pH 7.3). Non-specific binding was estimated in the presence of excess unlabeled PGE2 (10 μM). Binding data fitted to the binding model for a single class of binding sites, using nonlinear regression analysis. $IC_{50}$ values thus obtained were converted to Ki using the equation of $Ki=(IC_{50}/(1+[L]/K_D)$ where [L] represents PGE2 concentration (10 nM) and $K_D$ the dissociation constant for [$^3$H]PGE2 at human EP2 receptors (40 nM).

Radioligand Binding

Cells Stably Expressing $EP_1$, $EP_2$, $EP_4$ and FP Receptors

HEK-293 cells stably expressing the human or feline FP receptor, or $EP_1$, $EP_2$, or $EP_4$ receptors were washed with TME buffer, scraped from the bottom of the flasks, and homogenized for 30 sec using a Brinkman PT 10/35 polytron. TME buffer was added to achieve a final 40 ml volume in the centrifuge tubes (the composition of TME is 100 mM TRIS base, 20 mM $MgCl_2$, 2M EDTA; 10N HCl is added to achieve a pH of 7.4).

The cell homogenate was centrifuged at 19000 r.p.m. for 20 min at 4° C. using a Beckman Ti-60 rotor. The resultant pellet was resuspended in TME buffer to give a final 1 mg/ml protein concentration, as determined by Biorad assay. Radioligand binding competition assays vs. [$^3$H-]17 phenyl $PGF_{2\alpha}$, (5 nM) were performed in a 100 µvolume for 60 min. Binding reactions were started by adding plasma membrane fraction. The reaction was terminated by the addition of 4 ml ice-cold TRIS-HCl buffer and rapid filtration through glass fiber GF/B filters using a Brandel cell harvester. The filters were washed 3 times with ice-cold buffer and oven dried for one hour.

[$^3$H-] $PGE_2$ (specific activity 180 Ci mmol) was used as the radioligand for EP receptors. [$^3$H] 17-phenyl $PGF_{2\alpha}$ was employed for FP receptor binding studies. Binding studies employing $EP_1$, $EP_2$, $EP_4$ and FP receptors were performed in duplicate in at least three separate experiments. A 200 µl assay volume was used. Incubations were for 60 min at 25° C. and were terminated by the addition of 4 ml of ice-cold 50 mM TRIS-HCl, followed by rapid filtration through Whatman GF/B filters and three additional 4 ml washes in a cell harvester (Brandel). Competition studies were performed using a final concentration of 5 nM [$^3$H]-$PGE_2$, or 5 nM [$^3$H] 17-phenyl $PGF_{2\alpha}$ and non-specific binding determined with $10^{-5}$M of unlabeled $PGE_2$, or 17-phenyl $PGF_{2\alpha}$, according to receptor subtype studied.

Methods for FLIPR™ Studies (a) Cell Culture

HEK-293(EBNA) cells, stably expressing one type or subtype of recombinant human prostaglandin receptors (prostaglandin receptors expressed: hDP/Gqs5; $hEP_1$; $hEP_2$/Gqs5; $hEP_{3A}$/Gqi5; $hEP_4$/Gqs5; hFP; hIP; hTP), were cultured in 100 mm culture dishes in high-glucose DMEM medium containing 10% fetal bovine serum, 2 mM 1-glutamine, 250 µg/ml geneticin (G418) and 200 µg/ml hygromycin B as selection markers, and 100 units/ml penicillin G, 100 µg/ml streptomycin and 0.25 µg/ml amphotericin B.

(b) Calcium Signal Studies on the FLIPR™

Cells were seeded at a density of $5\times10^4$ cells per well in Biocoat® Poly-D-lysine-coated black-wall, clear-bottom 96-well plates (Becton-Dickinson) and allowed to attach overnight in an incubator at 37° C. Cells were then washed two times with HBSS-HEPES buffer (Hanks Balanced Salt Solution without bicarbonate and phenol red, 20 mM HEPES, pH 7.4) using a Denley Cellwash plate washer (Labsystems). After 45 minutes of dye-loading in the dark, using the calcium-sensitive dye Fluo-4 AM at a final concentration of 2 µM, plates were washed four times with HBSS-HEPES buffer to remove excess dye leaving 100 µl in each well. Plates were re-equilibrated to 37° C. for a few minutes.

Cells were excited with an Argon laser at 488 nm, and emission was measured through a 510-570 nm bandwidth emission filter (FLIPR™, Molecular Devices, Sunnyvale, Calif.). Drug solution was added in a 50 µl volume to each well to give the desired final concentration. The peak increase in fluorescence intensity was recorded for each well. On each plate, four wells each served as negative (HBSS-HEPES buffer) and positive controls (standard agonists: BW245C (hDP); $PGE_2$ ($hEP_1$; $hEP_2$/Gqs5; $hEP_{3A}$/Gqi5; $hEP_4$/Gqs5); $PGF_{2\alpha}$ (hFP); carbacyclin (hIP); U-46619 (hTP), depending on receptor). The peak fluorescence change in each drug-containing well was then expressed relative to the controls.

Compounds were tested in a high-throughput (HTS) or concentration-response (CoRe) format. In the HTS format, forty-four compounds per plate were examined in duplicates at a concentration of $10^{-5}$ M. To generate concentration-response curves, four compounds per plate were tested in duplicates in a concentration range between $10^{-5}$ and $10^{-11}$ M. The duplicate values were averaged. In either, HTS or CoRe format each compound was tested on at least 3 separate plates using cells from different passages to give an $n\geq3$.

Intraocular Pressure (IOP)

Intraocular pressure studies in dogs involve pneumatonometry performed on conscious Beagle dogs of both sexes (10-15 kg). The animals remain conscious throughout the study and are gently restrained by hand. Drugs are administered topically to one eye as a 25 µL volume drop, the other eye receives 25 µL vehicle (0.1% polysorbate 80:10 mM TRIS) as a control. Proparacaine (0.1%) is used for corneal anesthesia during tonometry. Intraocular pressure is determined just before drug administration and at 2, 4 and 6 hr thereafter on each day of the 5 day study. Drug is administered immediately after the first IOP reading.

The results of the binding and activity studies, presented in Table 1 below, demonstrate that the compounds disclosed herein are selective prostaglandin $EP_2$ agonists, and are thus useful for the treatment of glaucoma, ocular hypertension, inflammatory bowel disease, and the other diseases or conditions disclosed herein.

The foregoing description details specific methods and compositions that can be employed to practice the present invention, and represents the best mode contemplated. However, it is apparent for one of ordinary skill in the art that further compounds with the desired pharmacological properties can be prepared in an analogous manner, and that the disclosed compounds can also be obtained from different starting compounds via different chemical reactions. Similarly, different pharmaceutical compositions may be prepared and used with substantially the same result. Thus, however detailed the foregoing may appear in text, it should not be construed as limiting the overall scope hereof, rather, the ambit of the present invention is to be governed only by the lawful construction of the appended claims.

What is claimed is:

1. A compound of the structure

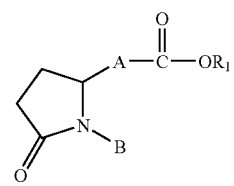

wherein

A is $-(CH_2)_6-$, cis $-CH_2CH=CH-(CH_2)_3-$, or $-CH_2C\equiv C-(CH_2)_3-$, wherein 1 or 2 carbon atoms may be substituted with S or O; or A is —(CH$_2$)$_m$—Ar—(CH$_2$)$_o$— wherein Ar is interarylene or heterointerarylene, the sum of m and o is from 1 to 4, and wherein one CH$_2$ may be substituted with S or O;

R$_1$ is C$_1$ to C$_6$ alkyl; and

B is optionally substituted aryl or optionally substituted heteroaryl.

2. The compound of claim 1 wherein B is phenyl.
3. The compound of claim 2 wherein B is alkylphenyl.
4. The compound of claim 2 wherein B is p-t-butylphenyl.
5. The compound of claim 2 wherein B is hydroxyalkylphenyl.
6. The compound of claim 1 wherein R$_1$ is C$_3$ alkyl.
7. The compound of claim 1 of the structure:

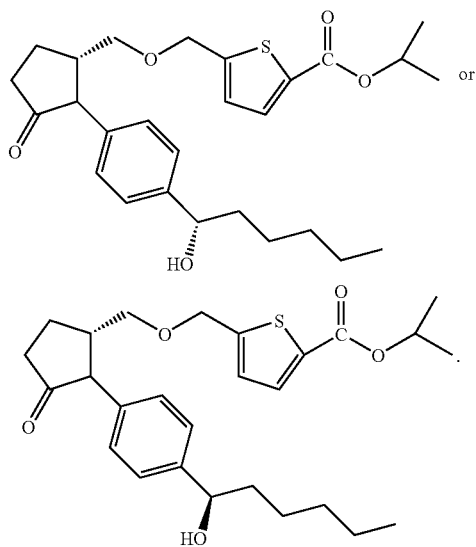

or

8. The compound of claim 1 of the structure:

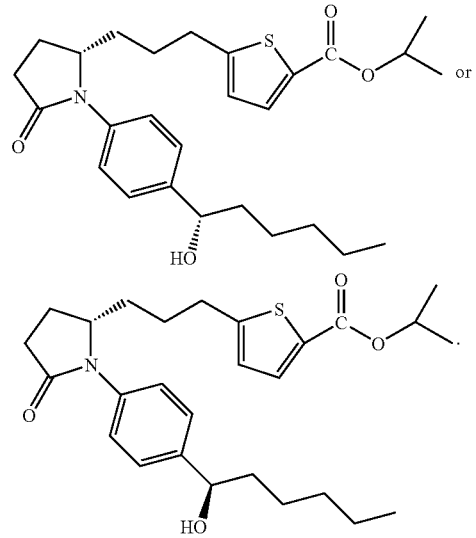

9. The compound of claim 1 of the structure

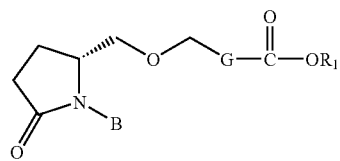

wherein

G is 1,3-interaryl or interheteroaryl, or —(CH$_2$)$_3$—;

R$_1$ is C$_1$ to C$_6$ alkyl; and

B is optionally substituted aryl or optionally substituted heteroaryl.

10. The compound of claim 9 wherein B is phenyl.
11. The compound of claim 10 wherein B is alkylphenyl.
12. The compound of claim 10 wherein B is p-t-butylphenyl.
13. The compound of claim 10 wherein B is hydroxyalkylphenyl.
14. The compound of claim 9 wherein R$_1$ is C$_3$ alkyl.
15. The compound of claim 1 of the structure

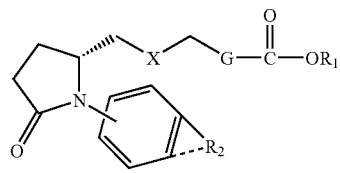

wherein a dashed line indicates the presence or absence of a bond;

R$_1$ is C$_1$ to C$_6$ alkyl;

R$_2$ is C$_1$ to C$_{12}$ hydrocarbyl or C$_1$ to C$_{12}$ hydroxyhydrocarbyl;

X is CH$_2$, O, or S; and

G is 1,3-interaryl or interheteroaryl, or —(CH$_2$)$_3$—.

16. The compound of claim 15, wherein R$_1$ is C$_3$ alkyl.
17. The compound of claim 15 wherein R$_1$ is isopropyl.
18. A method for treating glaucoma or ocular hypertension comprising administering to an eye of a subject in need thereof a therapeutically effective amount of a compound of the structure

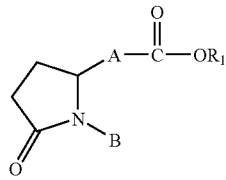

wherein

A is —(CH$_2$)$_6$—, cis —CH$_2$CH═CH—(CH$_2$)$_3$—, or —CH$_2$C≡C—(CH$_2$)$_3$—, wherein 1 or 2 carbon atoms may be substituted with S or O; or A is —(CH$_2$)$_m$—Ar—(CH$_2$)$_o$— wherein Ar is interarylene or heterointerarylene, the sum of m and o is from 1 to 4, and wherein one CH$_2$ may be substituted with S or O;

R$_1$ is C$_1$ to C$_6$ alkyl; and

B is optionally substituted aryl or optionally substituted heteroaryl.

19. A method for treating inflammatory bowel disease comprising administering to a subject in need thereof a therapeutically effective amount of a compound of the structure

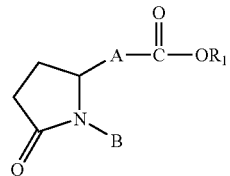

wherein

A is —$(CH_2)_6$—, cis —$CH_2CH=CH—(CH_2)_3$—, or —$CH_2C\equiv C—(CH_2)_3$—, wherein 1 or 2 carbon atoms may be substituted with S or O; or A is —$(CH_2)_m$—Ar—$(CH_2)_o$— wherein Ar is interarylene or heterointerarylene, the sum of m and o is from 1 to 4, and wherein one $CH_2$ may be substituted with S or O;

$R_1$ is $C_1$ to $C_6$ alkyl; and

B is optionally substituted aryl or optionally substituted heteroaryl.

20. A composition comprising a therapeutically effective amount of a compound, wherein said composition is ophthalmically acceptable, said compound of the structure

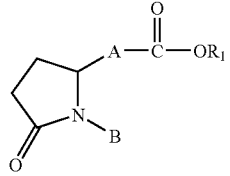

wherein

A is —$(CH_2)_6$—, cis —$CH_2CH=CH—(CH_2)_3$—, or —$CH_2C\equiv C—(CH_2)_3$—, wherein 1 or 2 carbon atoms may be substituted with S or O; or A is —$(CH_2)_m$—Ar—$(CH_2)_o$— wherein Ar is interarylene or heterointerarylene, the sum of m and o is from 1 to 4, and wherein one $CH_2$ may be substituted with S or O;

$R_1$ is $C_1$ to $C_6$ alkyl; and

B is optionally substituted aryl or optionally substituted heteroaryl.

* * * * *

UNITED STATES PATENT AND TRADEMARK OFFICE
CERTIFICATE OF CORRECTION

| | |
|---|---|
| PATENT NO. | : 7,973,071 B2 |
| APPLICATION NO. | : 12/323077 |
| DATED | : July 5, 2011 |
| INVENTOR(S) | : David W. Old et al. |

It is certified that error appears in the above-identified patent and that said Letters Patent is hereby corrected as shown below:

In the Specification

In column 1, line 10, after "which" delete "This".

In column 1, line 42, delete "pupilary" and insert -- pupillary --, therefor.

In column 2, line 29, delete "Chrohn's" and insert -- Crohn's --, therefor.

In column 2, line 30, delete "varialoforme" and insert -- varioliform --, therefor.

In column 2, line 35, delete "crythematosus" and insert -- erythematosus --, therefor.

In column 2, line 36, delete "Sjgren's" and insert -- Sjogren's --, therefor.

In column 2, line 40, delete "neohropathy" and insert -- nephropathy --, therefor.

In column 2, line 42-43, delete "Alzheimers" and insert -- Alzheimer's --, therefor.

In column 2, line 51, delete "periodonritis" and insert -- periodontitis --, therefor.

In column 3, line 26, delete "—CH$_2$)$_6$—" and insert -- —(CH$_2$)$_6$— --, therefor.

In column 3, line 65, after "esters" insert -- . --.

In column 6, line 53-54, delete "substitutents" and insert -- substituents --, therefor.

In column 8, line 48, delete "imidizololyl" and insert -- imidazolyl --, therefor.

In column 9, line 47, delete "substitutent" and insert -- substituent --, therefor.

In column 24, line 16, delete "distcarate" and insert -- distearate --, therefor.

In column 25, line 32, delete "thiossulfate" and insert -- thiosulfate --, therefor.

In column 25, line 67, delete "metiparanolol" and insert -- metipranolol --, therefor.

In column 26, line 18, delete "pilocarbine" and insert -- pilocarpine --, therefor.

In column 26, line 21, delete "chlolinesterase" and insert -- cholinesterase --, therefor.

In column 26, line 26, delete "dextrophan, detromethorphan" and insert -- dextrorphan, dextromethorphan --, therefor.

In column 26, line 31, delete "nifedimpine" and insert -- nifedipine --, therefor.

Signed and Sealed this
Thirtieth Day of June, 2015

Michelle K. Lee
*Director of the United States Patent and Trademark Office*

In column 27, line 18-19, delete "glucouronide" and insert -- glucuronide --, therefor.

In column 27, line 26, delete "chondroiton" and insert -- chondroitin --, therefor.

In column 41, line 53, after "(19)" insert -- . --.

In column 85, line 19, delete "PGF2α," and insert -- PGF2α --, therefor.

In column 85, line 20, delete "1001μvolume" and insert -- 100μl volume --, therefor.

In column 86, line 48, delete "hereof," and insert -- hereof; --, therefor.

In the Claims

In column 87, lines 19-40, in claim 7, delete

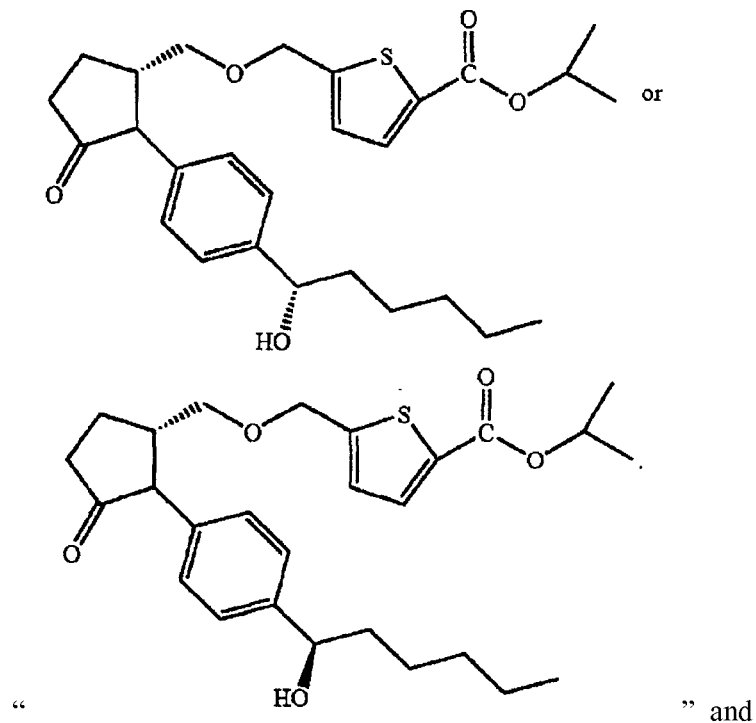

" and

CERTIFICATE OF CORRECTION (continued)
U.S. Pat. No. 7,973,071 B2

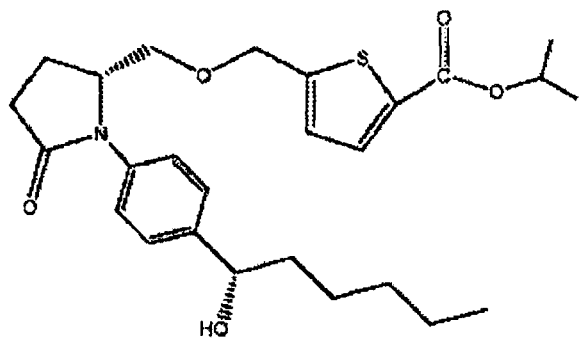

or insert -- 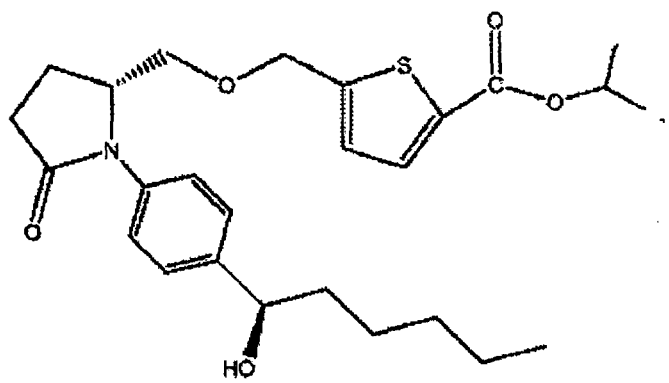 --, therefor.